US012578328B2

(12) United States Patent
Manda et al.

(10) Patent No.: US 12,578,328 B2
(45) Date of Patent: Mar. 17, 2026

(54) HIGH THROUGHPUT STOCHASTIC BIO-MOLECULAR SENSOR

(71) Applicant: Massachusetts Institute of Technology, Cambridge, MA (US)

(72) Inventors: Swathi Manda, Cambridge, MA (US); Ashwin Gopinath, Boston, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 7 days.

(21) Appl. No.: 18/476,272

(22) Filed: Sep. 27, 2023

(65) Prior Publication Data

US 2024/0118269 A1     Apr. 11, 2024

Related U.S. Application Data

(60) Provisional application No. 63/377,355, filed on Sep. 28, 2022.

(51) Int. Cl.
| | |
|---|---|
| *G01N 33/53* | (2006.01) |
| *G01N 27/447* | (2006.01) |
| *G01N 33/543* | (2006.01) |

(52) U.S. Cl.
CPC ..... *G01N 33/5308* (2013.01); *G01N 27/4473* (2013.01); *G01N 33/5438* (2013.01)

(58) Field of Classification Search
CPC ........... G01N 33/5308; G01N 27/4473; G01N 33/5438; G01N 30/6095; G01N 30/88; G01N 2030/8827
See application file for complete search history.

(56) References Cited

U.S. PATENT DOCUMENTS

| | | | |
|---|---|---|---|
| 2019/0032120 A1 | 1/2019 | Walter et al. | |
| 2019/0062814 A1 | 2/2019 | Aksimentiev et al. | |
| 2019/0170631 A1 | 6/2019 | Shachar et al. | |
| 2019/0309350 A1 * | 10/2019 | Howorka ............ | C12Q 1/6825 |
| 2020/0176082 A1 | 6/2020 | Massingham | |
| 2023/0175055 A1 * | 6/2023 | Otto ..................... | C12Q 1/6869 |
| | | | 435/6.1 |

FOREIGN PATENT DOCUMENTS

| | | | | |
|---|---|---|---|---|
| ES | 2887726 T3 * | 12/2021 | ........... | C12Q 1/6804 |

OTHER PUBLICATIONS

Hemmatian et al., "Electronic control of H+ current in a bioprotonic device with Gramicidin A and Alamethicin," 2016, Nature Communications, vol. 7, pp. 1-8 (Year: 2016).*

(Continued)

*Primary Examiner* — Luan V Van
*Assistant Examiner* — Kaylee Tseng
(74) *Attorney, Agent, or Firm* — McDonnell Boehnen Hulbert & Berghoff LLP

(57) ABSTRACT

What is described herein is a device for sensing a target, comprising a planar array of unique stochastic sensors, wherein each sensor is weakly cross-reactive with a unique determinant on the target; a means for capturing electrical signals from each sensor and the temporal duration of each signal; and a means for analyzing the cumulative signals from the array of stochastic sensors, and optionally further comprising a computer system for processing an algorithm for identifying the target based on the electrical signals from the sensors of the device.

13 Claims, 43 Drawing Sheets

Specification includes a Sequence Listing.

(56)                    References Cited

OTHER PUBLICATIONS

Li et al., "DNA-assembled bimetallic plasmonic nanosensors,"
2014, Light: Science & Applications, vol. 3, pp. 1-4 (Year: 2014).*
Hemmatian et al., "Electronic control of H+ current in a bioprotinic
device with Gramicidin A and Alamethicin" Nature Communica-
tions, 12981 (2016).
International Search Report and Written Opinion for PCT/US
23/75292 mailed Apr. 8, 2024.

* cited by examiner

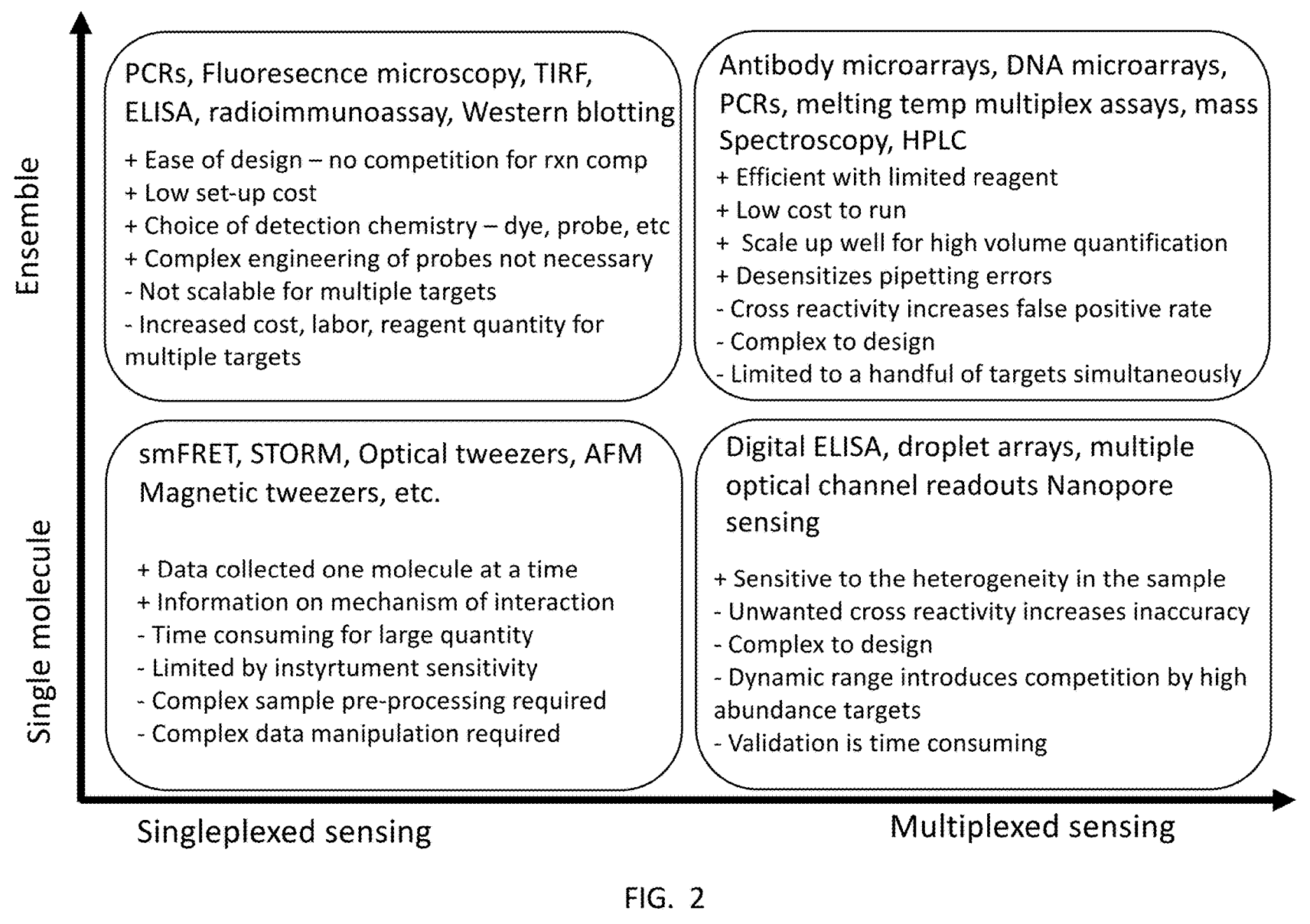

PCRs, Fluoresecnce microscopy, TIRF, ELISA, radioimmunoassay, Western blotting

+ Ease of design – no competition for rxn comp
+ Low set-up cost
+ Choice of detection chemistry – dye, probe, etc
+ Complex engineering of probes not necessary
- Not scalable for multiple targets
- Increased cost, labor, reagent quantity for multiple targets Antibody microarrays, DNA microarrays, PCRs, melting temp multiplex assays, mass Spectroscopy, HPLC + Efficient with limited reagent
+ Low cost to run
+ Scale up well for high volume quantification
+ Desensitizes pipetting errors
- Cross reactivity increases false positive rate
- Complex to design
- Limited to a handful of targets simultaneously smFRET, STORM, Optical tweezers, AFM Magnetic tweezers, etc.

+ Data collected one molecule at a time
+ Information on mechanism of interaction
- Time consuming for large quantity
- Limited by instyrtument sensitivity
- Complex sample pre-processing required
- Complex data manipulation required Digital ELISA, droplet arrays, multiple optical channel readouts Nanopore sensing + Sensitive to the heterogeneity in the sample
- Unwanted cross reactivity increases inaccuracy
- Complex to design
- Dynamic range introduces competition by high abundance targets
- Validation is time consuming Singleplexed sensing Multiplexed sensing Ensemble Single molecule

FIG. 2

Sequential targets for sensor calibration
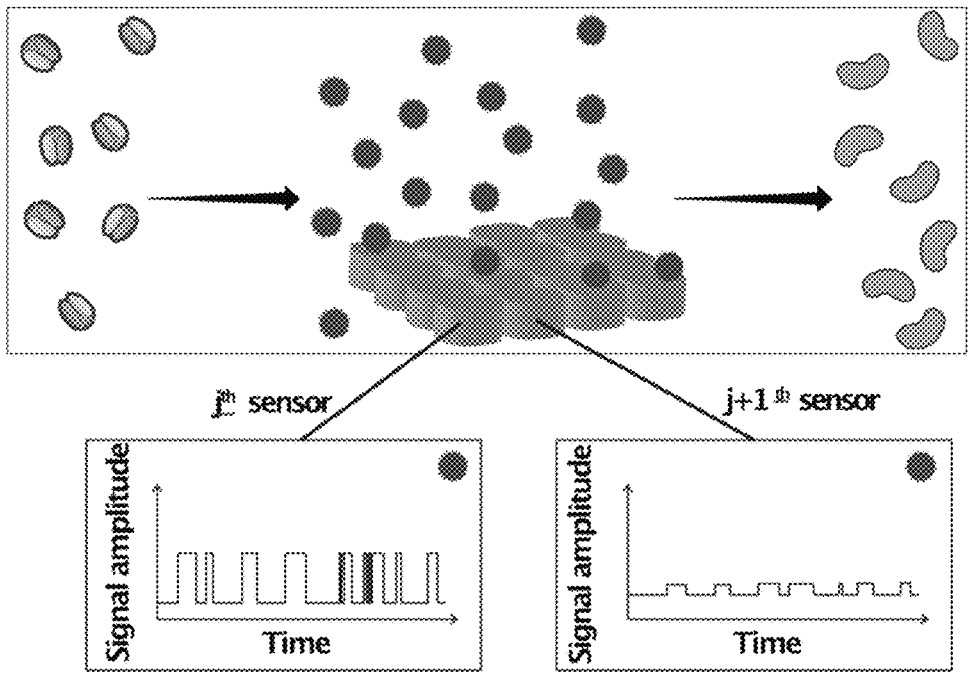
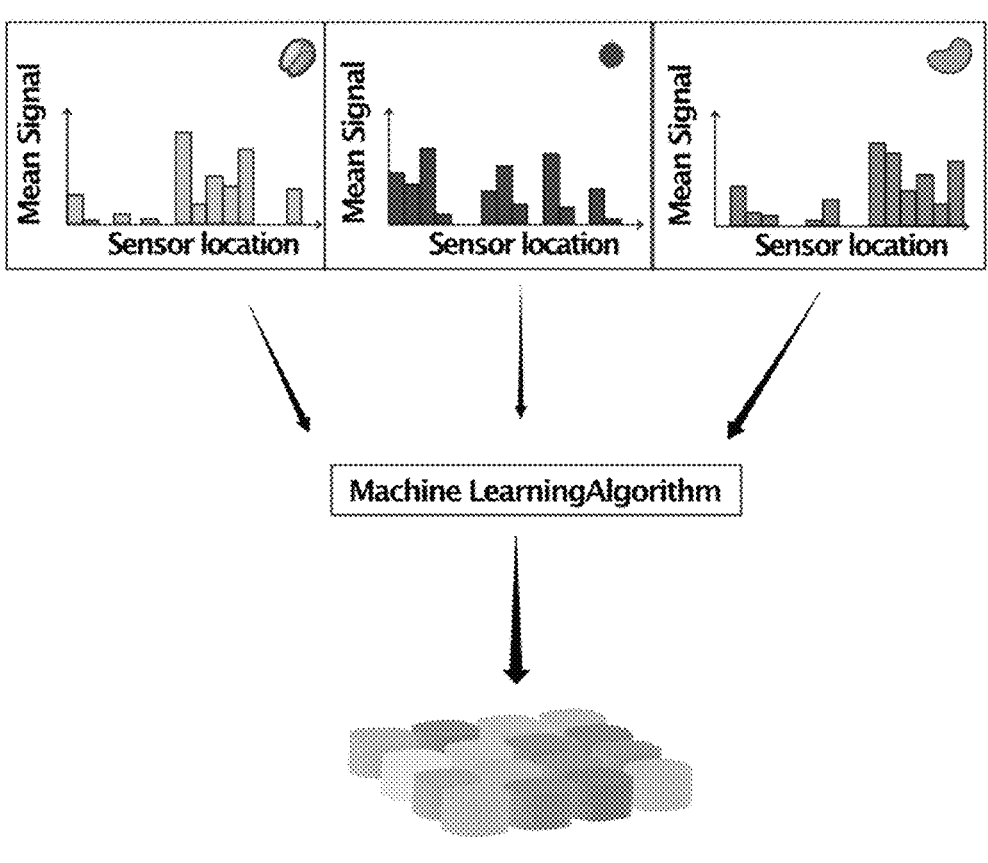
FIG. 3A

Multi-target mixture for sensor calibration

[III] Target classification accuracy

[II] Observed signal (i)
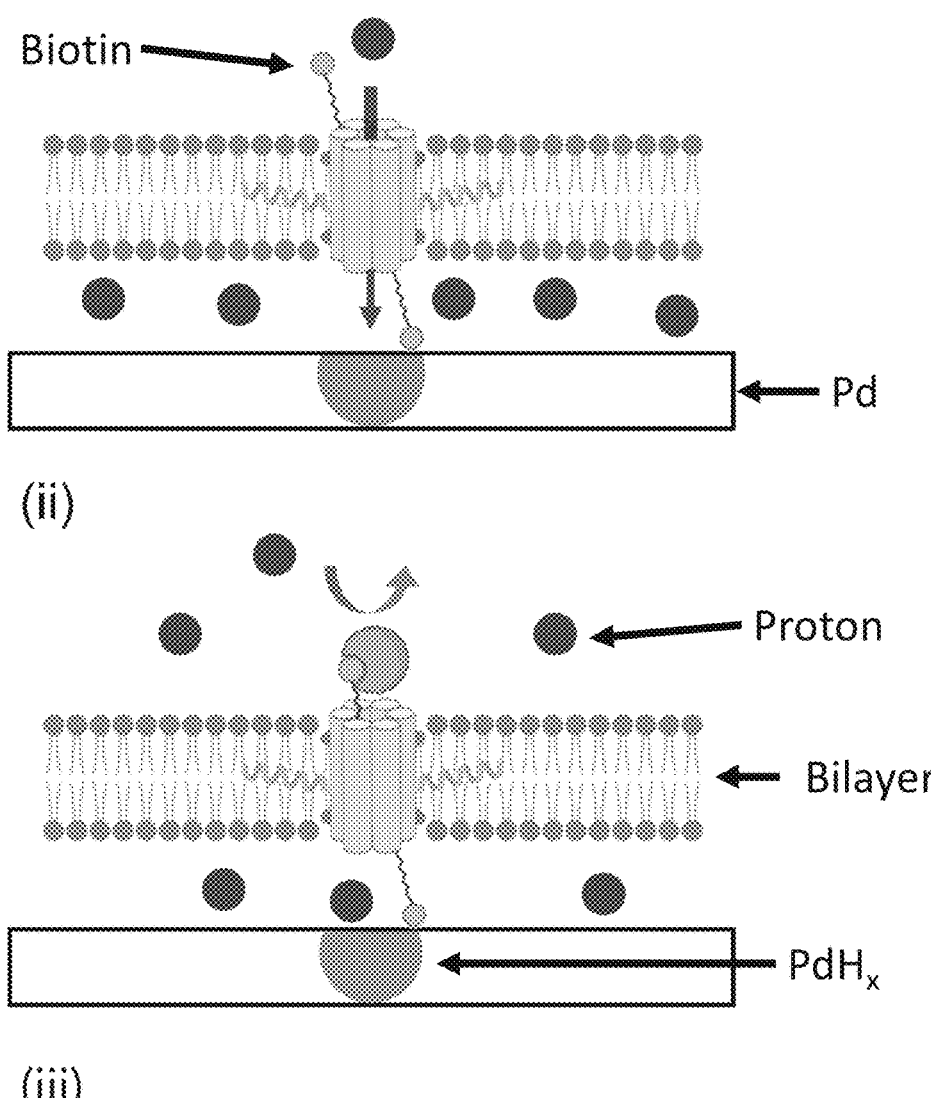
(ii)
(iii)
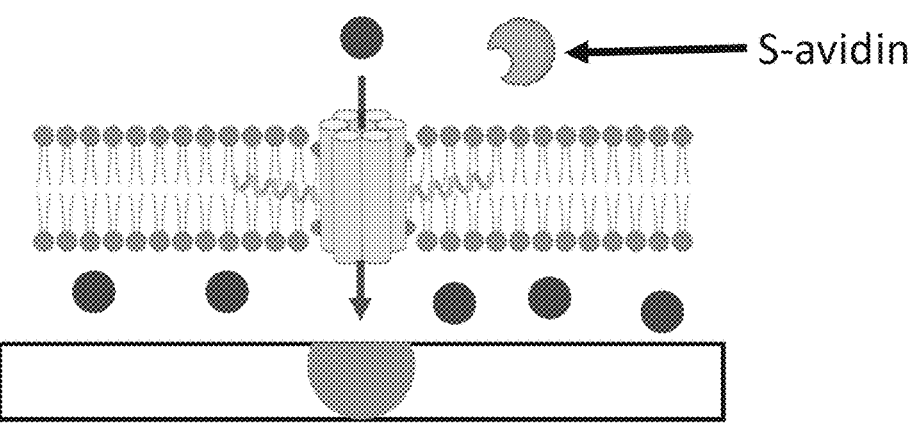
FIG. 10A (i)
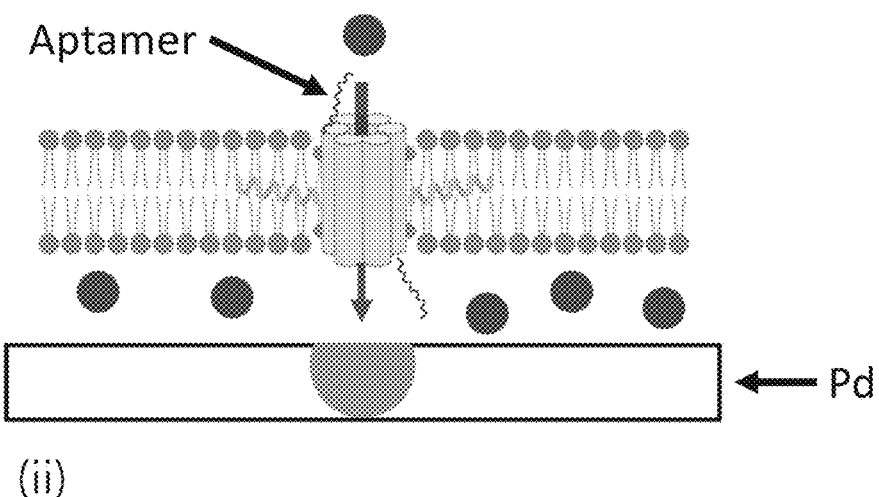
(ii)
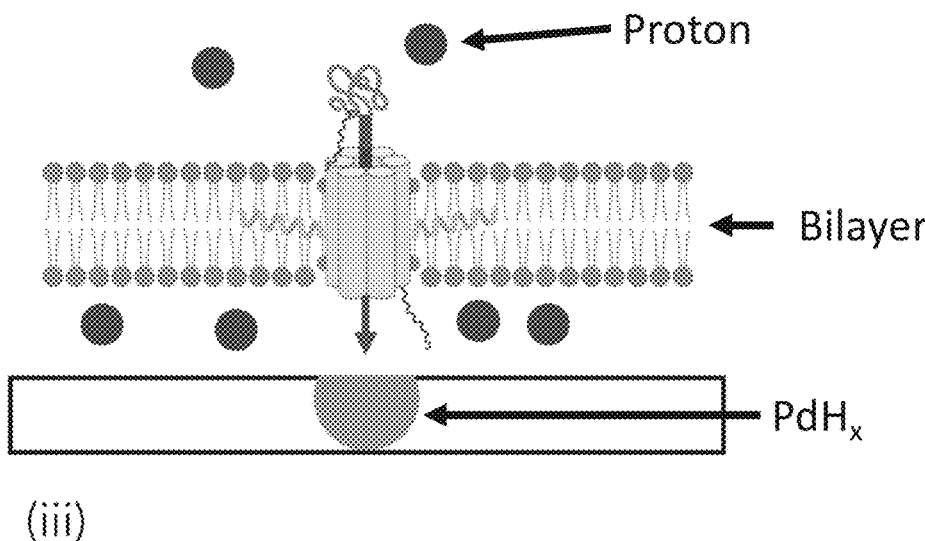
(iii)
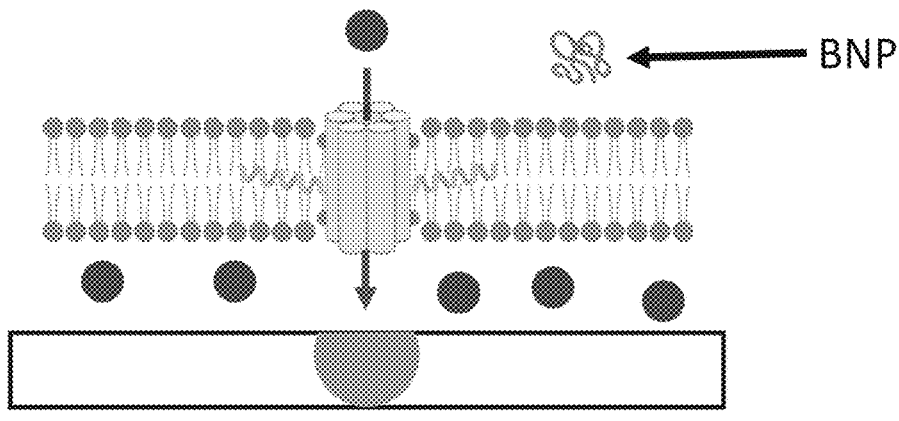
FIG. 10C 5' ●━━━━▶ 3' with TEG Cholesterol at 3' end
5' ■━━━━▶ 3'

6HB-2C-2B/S-avidin (ii)

6HB-2C-2B (i)

25 μm

25 μm

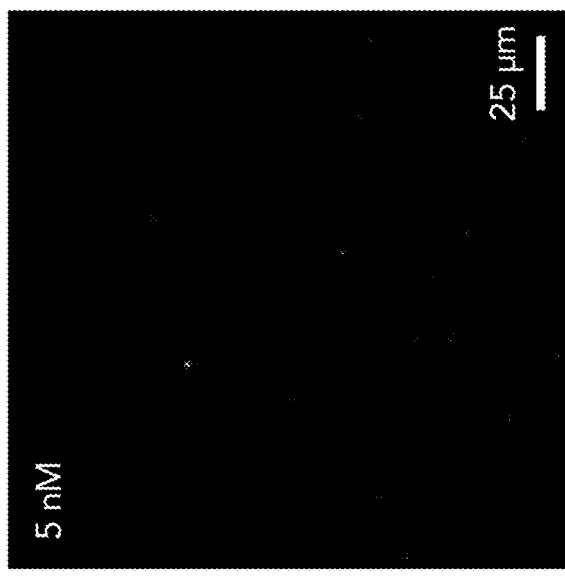
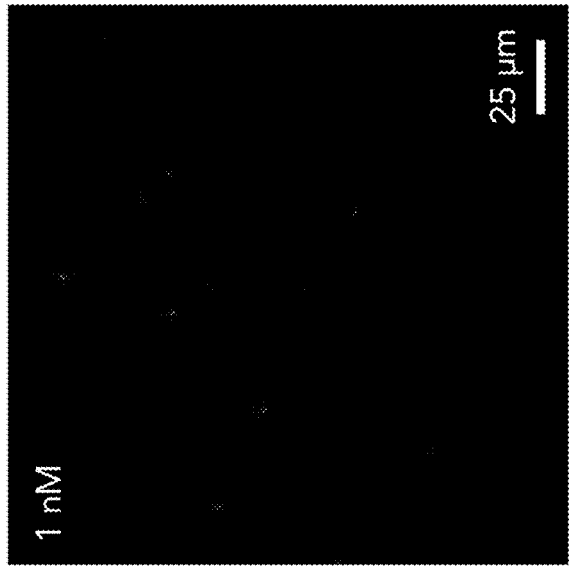
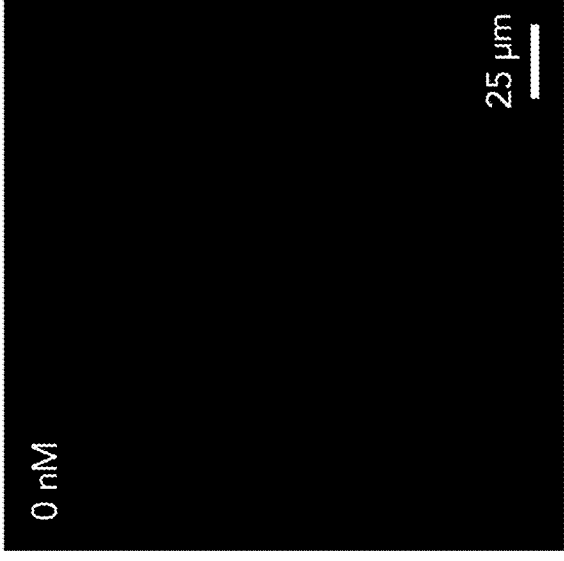
FIG. 19A

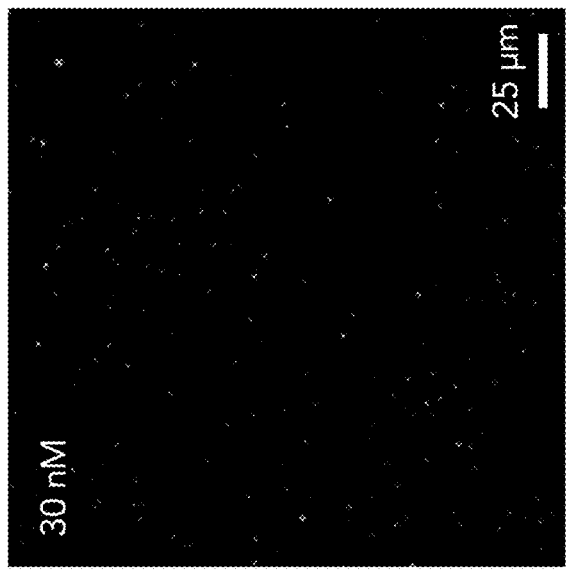
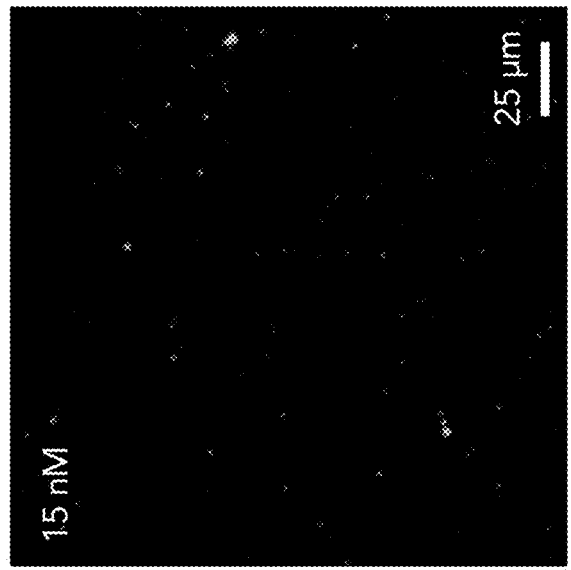
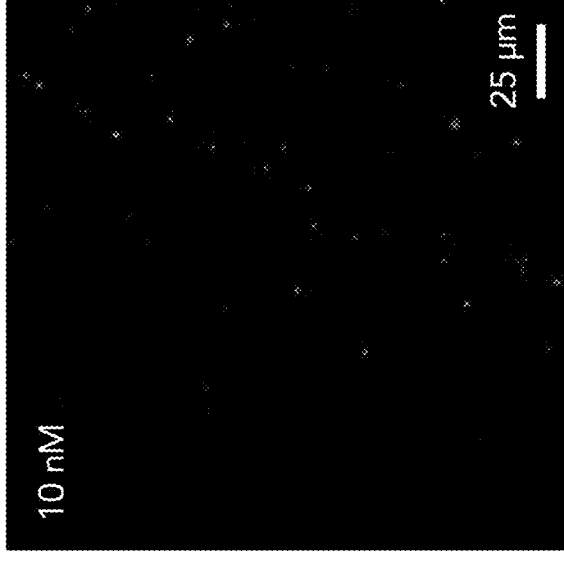
FIG. 19B

HIGH THROUGHPUT STOCHASTIC BIO-MOLECULAR SENSOR

CROSS REFERENCE TO RELATED APPLICATIONS

This application claims the benefit of U.S. Provisional Patent Application No. 63/377,355, filed Sep. 28, 2022, which is incorporated by reference herein in its entirety.

STATEMENT REGARDING FEDERALLY SPONSORED RESEARCH OR DEVELOPMENT

This invention was made with government support under grant number 2027165 awarded by National Science Foundation. The government has certain rights in this invention.

REFERENCE TO AN ELECTRONIC SEQUENCE LISTING

The contents of the electronic sequence listing (23-1027-US__MIT24610__WO_ST26_Sequence_Listing.xml; Size: 32,230 bytes; and Date of Creation: Sep. 27, 2023) is herein incorporated by reference in its entirety.

BACKGROUND

Single molecule measurements have the potential to make a significant impact in protein identification and quantitative analysis. However, sensing and quantifying the rich variety of proteins and their isoforms on a wide dynamic range is a significant challenge given the large variability of abundance of proteins in, e.g., biological samples. For example, in a typical serum sample, protein concentrations can range from about 1 µM (e.g., albumin and immunoglobulin) to 0.1 fM (e.g., cytokines), or even lower for some proteins, e.g., mutant proteins with low expression. Despite their potential, single molecule measurements have not become pervasive for protein and small molecules due to some fundamental challenges. First, the sensitivity of measurement of a rare marker using single molecule techniques is masked by the presence of other highly abundant markers due to stochastic readout noise. Increased sensitivity through additional sample preparation and filtration steps comes at the cost of speed and scalability. Second, it is currently impractical to measure ultra-low concentrated samples in reasonable time, due to presence of the concentration barrier and sensor crowding effects. Third, current technologies rely on highly selective sensors with strong binding affinities, thereby restricting the sensors to respond to only one marker, even when exposed to complex mixtures like bio-fluids. This attribute inherently hinders multiplexing as it constrains the sensing space to availability of highly selective sensors. Thus, there is a need for a technology that overcomes these limitations, facilitates sensitive, selective, high throughput molecule sensing, and has the potential to detect and quantify proteins over a high dynamic range, including down to sub femtomolar concentrations of protein markers directly from bio-fluid samples in real-time.

SUMMARY

This Summary introduces a selection of concepts in simplified form that are described further below in the Detailed Description. This Summary neither identifies key or essential features, nor limits the scope, of the claimed subject matter.

In one aspect, the disclosure provides a device for sensing one or more targets in a sample, the device including (i) an array of two or more stochastic sensors, in which each sensor interacts weakly with a determinant on the target; (ii) a means for capturing electrical signals from each sensor and the temporal duration and frequency of each signal; and (iii) a means for analyzing the cumulative signals from the array of stochastic sensors.

In another aspect, the disclosure provides a device for sensing one or more targets in a sample, including (i) a bioprotonic conducting material forming a planar array of protodes on a non-conducting substrate; (ii) a plurality of DNA origami tethered DNA nanopores immobilized to the planar array of protodes, in which the outer surface of the DNA nanopore includes one or more hydrophobic moieties; (iii) an insulating membrane that defines a space inferior to the membrane and a space superior to the membrane, in which a DNA nanopore spans the membrane and provides an ionic pathway between the bioprotonic conducting material inferior to the membrane and bulk solution; (iv) a power supply in electrical contact with each protode to provide an electric potential difference across the membrane; and (v) a detector to detect changes in electrical signal through the nanopore over time as each nanopore interacts with one or more targets, in which the electrical signal changes can comprise changes in signal magnitude, signal duration and frequency of signal changes.

In another aspect, the disclosure provides a method for identifying a target signature of and quantifying the abundance of one or more targets in a sample, including (i) introducing a sample into the space superior to the membrane of two or more DNA nanopores immobilized to the planar array of protodes in the device of claim 7; (ii) applying an electric field across the membranes; (iii) monitoring changes in signal magnitude, signal duration and frequency of signal change across each sensor in the membrane to define one or more target signatures; and (iv) determining a presence and abundance of a target in the sample as a function of the one or more target signatures.

In another aspect, the disclosure provides a method for fabricating a stochastic sensing device for sensing one or more targets in a sample, including (i) depositing a bioprotonic conducting material onto a non-conducting material arranged to form one or more protode contact areas; (ii) electrically isolating each protode contact area; (iii) introducing DNA origami to the protode contact areas for self-assembly onto the bioprotonic conducting material, in which the DNA origami include one or more anchoring linkers; (iv) introducing DNA nanopores to the protode contact areas, in which (a) the DNA nanopores include one or more nanopore anchoring linkers complementary to the anchoring linkers on the DNA origami, (b) one or more hydrophobic moieties on an outer surface of the DNA nanopores, and (c) one or more target binding moieties opposite the nanopore anchoring linkers; where the nanopore anchoring linkers bind to the anchoring linkers on the DNA origami thereby immobilizing the nanopores on the DNA origami; and where the target binding moieties interact weakly with one or more determinants on the target; (v) forming a membrane within the electrically isolated protode contact area and surrounding the DNA nanopore, defining a space inferior to the membrane and a space superior to the membrane, such that one ionic pathway exists between the bioprotonic conducting material and the space superior to the membrane, through the nanopore; where each protode contact area contains on average one immobilized DNA nanopore; and where the stochastic sensing device can detect changes in signal magnitude, signal duration and frequency of signal change across the membrane upon exposure to one or more targets in a sample. In some embodiments, the target binding moieties include aptamers such as DNA, RNA, XNA, peptides, or combinations thereof.

BRIEF DESCRIPTION OF THE DRAWINGS

The accompanying drawings, which are included to provide a further understanding of the disclosure, are incorporated in and constitute a part of this specification, illustrate embodiments of the disclosure, and together with the detailed description serve to explain the principles of the disclosure. No attempt is made to show structural details of the disclosure in more detail than may be necessary for a fundamental understanding of the disclosure and various ways in which it may be practiced.

FIG. 2 shows a schematic showing broad classification of current bio-molecular quantification technologies along the axes of single-plexed versus multiplexed sensing and Single molecule vs. Ensemble measurements. Schematics of the representative technologies are shown for each class.

FIG. 3A and FIG. 3B illustrate calibration pathways for target quantification using randomly assembled planar array of unique, weakly cross-reactive stochastic sensors. Pathway in FIG. 3A on the left shows calibration via sequential target exposure. Signatures of each sensor for the set of targets are fed through a machine learning algorithm to classify the sensor identity. The pathway in FIG. 3B on the right shows sensor identity agnostic calibration for target quantification. Here, a mixture of targets is introduced simultaneously. Each sensor produces a mixed record which is an amalgamation of the individual sensor-target interactions. The mixed records are sensed and fed through a machine learning algorithm for an unsupervised clustering of sensor's baseline fingerprint against a set of targets.

FIG. 4A [I] shows the distribution of the log of dissociation coefficients for a single cross-reactive sensor that is interacting with eight different targets. These values are observed by sensor S1. FIG. 4A [II] shows the data as seen by the sensor broken down into contributions arising from each of the eight targets; FIG. 4B: illustrates that when two sensors, S1 and S2, are used, the target-sensor interactions can be mapped along two dimensions and they begin to spatially cluster together based on their mean and deviation. However, they are still not entirely classifiable; FIG. 4C [I] illustrates that when three sensors, S1, S2 and S3 are used, the eight targets can be mapped into three dimensions, and their interaction parameters cluster into tighter knit clusters that are better segregated spatially. FIG. 4C [II] shows a confusion matrix showing the test accuracy of classification using a k-neighbors learning algorithm to classify the identity of eight targets in interaction with three sensors.

FIG. 5A shows a small window of a dynamic time trace of a simulation with sensor coated single bead in an optical trap interacting with target molecules in the solution. The true on and off events are shown in red whereas the transducer readout from the single sensor is shown in blue. The simulation was generated using single bead SPASM. FIG. 5B and FIG. 5C show estimated $k_{off}$ and k on values using the algorithm.

FIG. 6A shows an illustration of the construction of a DNA origami, e.g., an anchoring DNA origami using staple strands and scaffold strands. FIG. 6B shows an illustration of a DNA nanopore sensor as described herein, including complementary anchoring linkers that bind to a DNA origami immobilized on an conductive surface, e.g., protode, hydrophobic moieties for insertion into a membrane and aptamers for interacting with one or more targets. The DNA nanopore is also shown in a schematic of an exemplary fully assembled sensor (electromoriogram). FIG. 6C shows an organized array of sensors on a non-conducting substrate, as well as a schematic showing a method of fabrication of the electromoriogram using electron beam lithography (EBL), nano-sphere lithography (NSL), reactive ion etching (ME), passivation and bead removal, followed by assembly of a working sensor.

FIG. 8A shows a schematic depiction of the bioprotonic device. FIG. 8B shows a schematic representation of a DNA nanopore comprising six-helix bundles and 2-cholesterol anchors. FIG. 8C shows a top view of DNA nanopores with positioned cholesterol anchors. FIG. 8D shows a lateral view of DNA nanopores with positioned base pairs. FIG. 8E shows a simulation of the average distance between the diametrically opposite strands across the length of the nanopore. "H1-H4" curve represents the distance between strands 1 and 4; the "H2-H5" curve represents for distance between strands 2 and 5 and the "H3-H6" curve represents the distance between strands 3 and 6. FIG. 8F shows an average distance heatmap for the pairs indicated in FIG. 8C and FIG. 8E. The H3-H6 pair demonstrate the greatest divergence as seen as the dark shading on the top and bottom of the graph (and graph of FIG. 8E).

FIG. 9A(1) shows a Pd contact with electrolyte solution; FIG. 9A(2) shows a Pd contact coated with SLBs; FIG. 9A(3) shows DNA nanopores with 2-cholesterol anchors (6HB-2C); FIG. 9A(4) shows DNA nanopores without cholesterol anchor (6HB); FIG. 9A(5) shows DNA nanopores with 1-cholesterol anchor (6HB-1C); FIG. 9A(6) shows DNA nanopores with 3-cholesterol anchors (6HB-3C). FIG. 9B shows a $I_{H+}$ versus time plot for V=−400 mV and V=0 mV. The "Pd (i)" trace represents Pd; the "SLB (ii)" trace represents SLB; and the "6HB-2C (iii)" trace represents 6HB-2C. At V=−400 mV, the $I_{H+}$=−125±11 nA with a bare Pd, which decreased to −7±1 nA with SLBs, indicating bilayers inhibit $H^+$ transfer from the bulk solution to the Pd/solution interface. An $I_{H+}$=−52±4 nA with 6HB-2C confirmed that the nanopore channels support the $H^+$ transport. Error bars are 1 s.d. (n=3). FIG. 9C shows a $I_{H+}$ versus time plot for different conditions of FIG. 8A under V=−400 mV and V=0 mV. The "6HB-2C (iii)" trace represents 6HB-2C (FIG. 8A(iii)); the "6HB (iv)" trace represents 6HB (FIG. 8A(iv)), the "6HB-1C (v)" trace represents 6HB-1C (FIG. 8A(v)); and the "6HB-3C (vi)" trace represents 6HB-3C (FIG. 8A(vi)). Under −400 mV, $I_{H+}$ was measured at −11±5 nA, −13±7 nA, and −12±4 nA for 6HB, 6HB-1C and 6HB-3C, respectively. Error bars are 1 s.d. (n=3). Only 6HB-2C provided a pathway to facilitate the flow of $H^+$ to the Pd/solution interface. For all measurements, the voltage was switched to 0 mV after about 600 s from the first instance of measurement, so that the H absorbed in Pd was oxidized to $H^+$ and released back into the solution, allowing the current measured to return to 0 nA.

FIG. 10A to FIG. 10D show schematics of bioprotonic devices with biotin-streptavidin and aptamer-peptide. FIG. 10A(i) shows 2-cholesterol handled DNA nanopores with biotin in the absence of streptavidin (6HB-2C-2B). The absence of streptavidin allowed the nanopore to facilitate $H^+$ transfer without inhibition; FIG. 10A(ii) shows 2-cholesterol-handled DNA nanopores with binding of biotin-streptavidin (6HB-2C-2B/S-avidin). $H^+$ transfer was inhibited by streptavidin blocking the pore channels; FIG. 10A (iii) shows 2-cholesterol-handled DNA nanopores without biotin in the presence of streptavidin (6HB-2C/S-avidin). The pores were not blocked by binding due to the lack of a streptavidin binding partner on the nanopore. FIG. 10B shows a $I_{H+}$ versus time plot for V=−400 mV. The "6HB-2C-2B (i)" trace represents 6HB-2C-2B (FIG. 10A(i)); the "6HB-2C-2B/S-avidin (ii)" trace represents 6HB-2C-2B/S-avidin (FIG. 10A(ii)); and the "6HB-2C/S-avidin (iii)" trace represents 6HB-2C/S-avidin (FIG. 10A(iii)). $I_{H+}$ was measured as −96±21 nA, −12±6 nA and −92±9 nA for 6HB-2C-2B, 6HB-2C-2B/S-avidin and 6HB-2C/S-avidin, respectively. Error bars are 1 s.d. (n=3). FIG. 10C(i) shows 2-cholesterol handled DNA nanopores with SELEX-based DNA aptamer in the absence of B-type natriuretic peptide (6HB-2C-2AP). The absence of the peptide allowed the nanopore to facilitate $H^+$ transfer without inhibition; FIG. 10C(ii) shows 2-cholesterol-handled DNA nanopores with binding of aptamer-peptide (6HB-2C-2AP/BNP). $H^+$ transfer was slightly inhibited by blocked pore channels; FIG. 10C(iii) shows 2-cholesterol-handled DNA nanopores without aptamer in the presence of peptide (6HB-2C/BNP). FIG. 10D shows a $I_{H+}$ versus time plot for V=−400 mV. The "6HB-2C-2AP (i)" trace represents 6HB-2C-2AP (FIG. 10C (i)); the "6HB-2C-2AP/BNP (ii)" trace represents 6HB-2C-2AP/BNP (FIG. 10C(ii)); and the "6HB-2C/BNP (iii)" trace represents 6HB-2C/BNP (FIG. 10C(iii)). $I_{H+}$ was measured to be −90±3 nA, −51±1 nA and −96±9 nA for 6HB-2C-2AP, 6HB-2C-2AP/BNP and 6HB-2C/BNP, respectively. Error bars are 1 s.d. (n=3).

FIG. 11A shows a plot of $I_{H+}$ versus the introduced 6HB-2C concentration ($C_n$) plot ($V_{H+}$= −400 mV) for 6HB-2C nanopores. $I_{H+}$ was measured as −15±8 nA, −25±3 nA, −44±1 nA, −52±4 nA, −92±15 nA, −111±9 nA and −110±3 nA for 0 nM, 5 nM, 10 nM, 15 nM, 30 nM, 45 nM and 100 nM of 6HB-2C, respectively. Error bars are 1 s.d. (n=10, 3, 3, 3, 6, 3 and 3 for 0 nM, 5 nM, 10 nM, 15 nM, 30 nM, 45 nM and 100 nM respectively). FIG. 11B shows a plot of the number of inserted 6HB-2C nanopores (N) versus the introduced 6HB-2C concentration ($C_n$). The value of the slope in the plot is 64. Error bars are 1 s.d. (n=3). FIG. 11C shows a plot of $I_{H+}$ versus the number of inserted 6HB-2C nanopores (N) under −400 mV. The value of the slope in the plot is $4 \times 10^{-11}$. Error bars are 1 s.d. (n=3). FIG. 11D shows a plot of $I_{H+}$ versus time during the 15 nM 6HB-2C insertion process under −400 mV.

FIG. 13A shows a sequence design with strand crossover details. Strands with a filled circle terminus indicate those oligos that have been modified at the 3′ end with Tri-ethylene Glycol (TEG)-cholesterol moieties. Strands with a filled square terminus indicate oligos without any modifications. Triangles indicate the 3′ end of DNA. FIG. 13B shows negatively stained TEM micrograph of the 6HB nanopores. Circles show the nanopores in a flat orientation.

FIG. 14A shows electrophoretic characterization (2% Agarose gel) of the nanopores with different number of cholesterol tags at the midsection of the nanopore barrel. Lane 1 and 2, DNA ladders; lane 3, fluorescent 6HB nanopores without cholesterol tags; lane 4, 6HB-3C fluorescent nanopores with three cholesterol tags; lane 5, 6HB-2C fluorescent nanopores with two cholesterol tags; lane 6, 6HB-1C fluorescent nanopores with one cholesterol tag. The position of the Kilobase pair length of dsDNA markers is indicated on the left of the gel. FIG. 14B shows electrophoretic characterization (2% Agarose gel) of migration patterns of biotin-modified nanopores in presence and absence of excess streptavidin. Lanes 1 and 2, DNA ladders; lane 3, 6HB-2B nanopores without cholesterol modifications; lane 4, 6HB-2C nanopores without biotin modifications; lane 5, 6HB-2B-2C modifications; lane 6, 6HB-2B modifications with excess streptavidin (1×:20×); lane 7, 6HB-2C modifications with excess streptavidin (1×: 20×); lane 8, 6HB-2C modifications with excess streptavidin (1×:20×).

FIG. 14C shows a dynamic light scattering trace of the volume-based size distribution of 6HB nanopores (left side line) without any cholesterol tags and 6HB-3C nanopores (right side line) containing three cholesterol tags as measured on a Zetasizer instrument. Average values of five repeated experiments are shown. FIG. 14D shows size correlograms for 6HB and 6HB-3C nanopores showing the raw correlation function versus delay time data in the form of G2($\tau$)−1. Both the samples show multiple scattering with intercepts less than 1 due to intensity-based size calculations including large scattering effects from multiple size populations and aggregates when present even in extremely low fractions. Average values of five repeated experiments are shown.

FIG. 15A shows an equivalent circuit schematic utilized to fit experimental data with the top figure representing the tested bioprotonic device, and the bottom figure representing the bioprotonic device with SLB. The electrolyte solution resistance, Rs, is in series with membrane capacitance, Cm, membrane resistance, Rm, double layer capacitance, Cdl, charge transfer resistance, Rct, adsorption resistance Rp, and adsorption capacitance. Fitting to the experimental data was performed using ZSimpWin, and the results are provided in Table 1. FIG. 15B shows a Nyquist plot illustrating the relationship between the real and imaginary part of the impedance for both bioprotonic devices and lipid bilayers. FIG. 15C shows a Bode plot depicting the magnitude and phase of impedance as a function of frequency ("Pd" represents Pd and "+SLB" represents SLB).

FIG. 16A shows fluorescence intensity recovery after photobleaching at t=pre, 0, and 20 min post-photobleaching (from left to right). FIG. 16B shows a determination of the effective bleaching spot. The Gaussian amplitude function was used to extract the effective bleaching spot radius. FIG. 16C shows the normalized fluorescence intensity of FRAP recovery curve. This experiment was independently repeated three times, and the results shown here are representative.

FIG. 17A shows a fluorescence image of DNA nanopores with 2-cholesterol and biotin in the absence of streptavidin (6HB-2C-2B), showing ~205 nanopores. FIG. 17B shows a fluorescence image of the same nanopores after binding with S-avidin (6HB-2C-2B/S-avidin), showing ~200 nanopores. Representative results from five independent experiments are presented.

FIG. 19A to FIG. 19B show fluorescence images of DNA nanopores at different concentrations. Representative results from five independent experiments are presented.

DESCRIPTION

Figure 1:
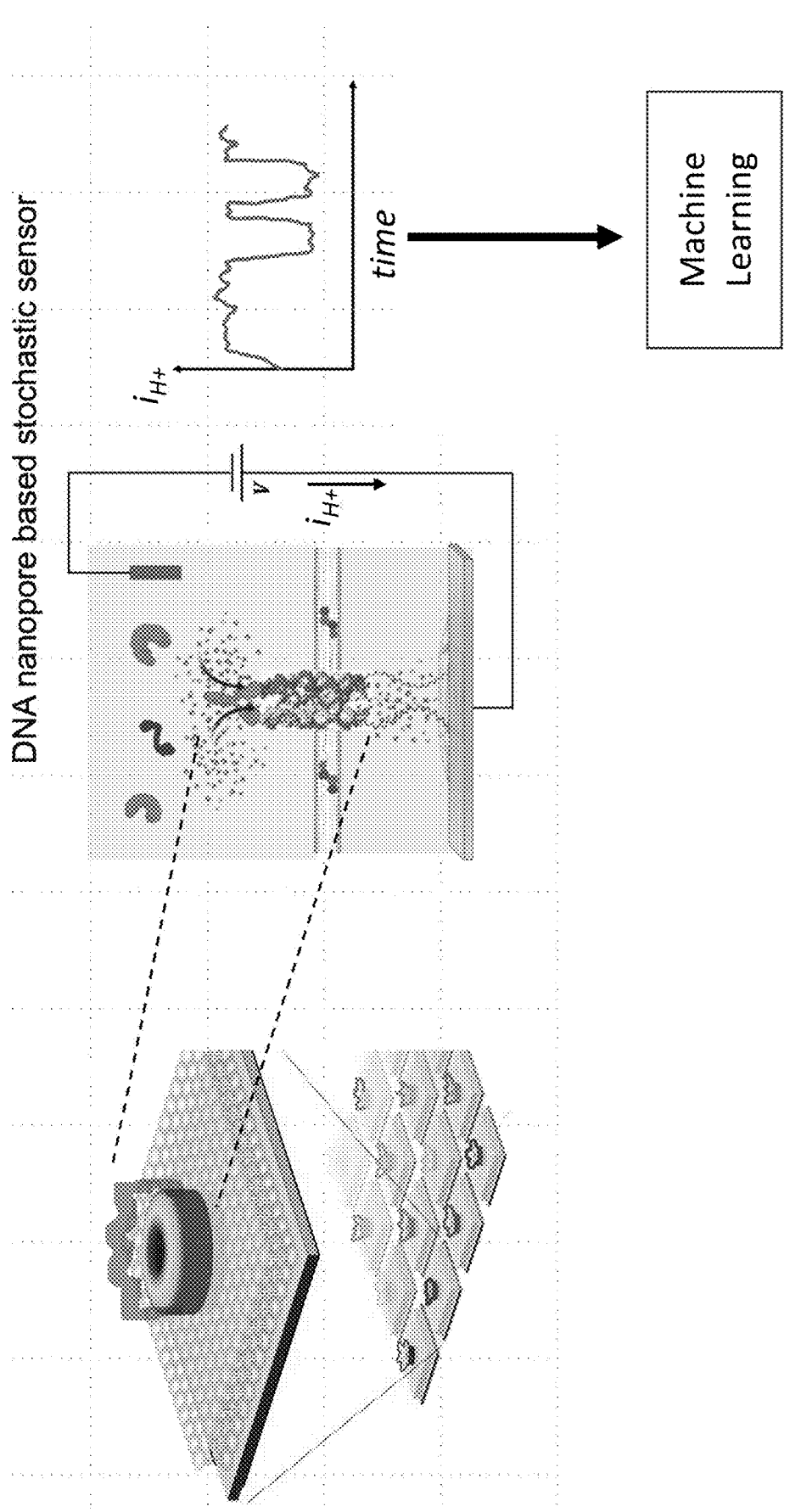
FIG. 1 shows a schematic of a design and set up of a planar array of unique, weakly binding stochastic sensors that are cross-reactive to targets in the solution are exposed to the sample (electromoriogram). The electrical signal from each sensor is captured temporally and analyzed collectively with all other sensors on the array to quantitatively measure the presence and abundance of molecules in the sample in real time. The ionic current signal can reveal the abundance of the biomolecule interacting with the sensor.

Disclosed herein are sensing devices ("electromoriograms", from Latin roots "electro" meaning electrical, "morio" meaning molecule, and "gram" meaning to record) that include an array of two or more stochastic sensors that interact weakly with a determinant(s) on one or more targets (e.g., biomolecules in a biological sample), resulting in changes in current flow across the sensors that are captured and analyzed to determine characteristics of the target(s), including determining a unique signature for a given target. Methods for identifying a target signature are provided, as well as methods for fabricating the sensing devices.

A number of terms are introduced below:

The term "stochastic sensor" refers to a sensor with a reasonably measurable sensor-target complex lifetime. In its simplest form, it is a single molecule sensor with an added dimension of time such that it can exist in one of two states, each with its unique signal, i.e., occupied by the target or unoccupied by the target. Unlike other single molecule electrochemical, colorimetric, spectrophotometric, and antibody-based sensors, a stochastic sensor can have a rapid and reversible response to the presence or absence of a target molecule making it feasible to monitor dynamic changes in binding events and target concentration.

The term "aptamer" refers to short sequences of artificial DNA, RNA, XNA, or peptide that bind a specific target molecule or family of target molecules. Aptamers can exhibit a large range of affinities, which affinities can be user selectable given most aptamers are generated via systematic evolution of ligands by exponential enrichment (SELEX), or in vitro selection or evolution. SELEX is a combinatorial chemistry technique in molecular biology for producing oligonucleotides of either single-stranded DNA or RNA that specifically bind to a target ligand or ligands. For peptide aptamers, numerous combinatorial peptide aptamer library technologies exist, including loop on frame scaffolds (e.g., Thioredoxin scaffolds, Combinatorial Library of Improved Peptide Aptamers (CLIPs), Adnectins or Monobodies, Anticalins, Avimers, Knottins, Fynomers, Kunitz Domains, and Atrimers) and scaffolds containing rigid combinatorial motifs (e.g., DARPins (Designed Ankyrin Repeat Proteins), Affibodies, Affilins, Armadillo Repeats (ArmRPs), and OBodies (oligonucleotide binding (OB)-fold anticodon recognition domain from *Pyrobaculum aerophilum*)). Peptide aptamer selection technologies generally comprise selection through extracellular display, such as the surface of cells, filamentous phages, or in vitro, and in vivo screening and selection represented by a number of in-cell protein complementation assays, including two-hybrid systems, in which the target and ligand are both produced and interact inside a living cell.

The terms "protode" and "bioprotonic conducting material" refers to a contact (colloquially "electrode") that is capable of both injecting and draining protons at the proton conductor interface. Most metal contacts in devices (e.g., Au, Pt) are good electronic conductors but poor proton conductors. To circumvent this obstacle, often ionic devices function using alternating current. To enable bioprotonic devices that function using direct current, a contact is needed that is capable of both injecting and draining protons (H⁺) at the proton conductor interface, but it is also able to conduct electrons for connecting to outside electronics. As an example, palladium forms proton conducting $PdH_x$ (palladium hydride) upon exposure to hydrogen or electrochemical loading of protons. When the electrode is immersed in an aqueous solution and a potential difference is applied between the $PdH_x$ electrode and an electrode in the solution the $PdH_x$ contact injects or sinks protons depending on the voltage and exact concentration of H in the electrodes. This electronic current is the result of the redox reaction of H⁺ and H at the Pd surface. For $PdH_x$, every proton exchanged with the proton conducting material results in an electron being exchanged with the external leads, and the measured electronic current, therefore, effectively monitors the H⁺ transport process in the proton conducting material. A bioprotonic conducting material, or protode, functionalized with an engineered DNA nanopore, itself bound to a membrane that separates the protode from the bulk solution and has not been previously described. Protodes can be combined with a reference electrode, e.g., Ag/AgCl, located on the opposite side of the membrane from a protode to complete an electrical circuit across the DNA nanopore and membrane such that when a voltage ($V_{H+}$) is applied between the protode contact and the Ag/AgCl reference electrode positioned on the opposite side of the membrane, a current of H⁺ between the protode contact and the solution is observed, depending on polarity. Such flow of H⁺ induces the electrochemical formation or dissolution of $PdH_x$ that results in a measurable current ($I_{H+}$) in the electronic circuit.

The terms "top", "bottom", "lower", "upper", "above", "below", "on", and the like, are used herein to describe the nanopore sensor device and/or the various components of the nanopore sensor device. It is to be understood that these directional terms are not meant to imply a specific orientation but are used to designate relative orientation between components. The use of directional terms should not be interpreted to limit the examples disclosed herein to any specific orientation(s).

The terms "first", "second", etc. also are not meant to imply a specific orientation or order, but rather are used to distinguish one component from another.

It is to be understood that the ranges provided herein include the stated range and any value or sub-range within the stated range, as if such values or sub ranges were explicitly recited. For example, a range from about 50 mM to about 500 mM should be interpreted to include not only the explicitly recited limits of from about 50 mM to about 500 mM, but also to include individual values, such as about 100 mM, about 335 mM, about 400.5 mM, about 490 mM, etc., and sub-ranges, such as from about 75 mM to about 475 mM, from about 200 mM to about 300 mM, etc.

Furthermore, when "about", "approximately" and/or "substantially" are/is utilized to describe a value, this is meant to encompass minor variations (up to +/−10%) from the stated value. Unless specifically stated to the contrary, for ranges specified using "about" language, the about applies to both ends of the recited range whether specified or not. For example, "between about 10 mM and 10 µM" is equivalent to "between about 10 mM and about 10 µM".

Recitation of ranges of values herein are merely intended to serve as a shorthand method of referring individually to each separate value falling within the range, unless otherwise indicated herein, and each separate value is incorporated into the specification as if it were individually recited. For example, if a size range is stated as 1 nm to 100 nm (or concentrations, degrees, mass amounts, and the like), it is intended that values such as 2 nm to 90 nm, 10 nm to 70 nm, 30 nm to 95 nm, 75 nm to 100 nm, or 2 nm to 27 nm, etc., are expressly enumerated in this specification. These are only examples of what is specifically intended, and all possible combinations of numerical values between and including the lowest value and the highest value enumerated are to be considered to be expressly stated in this disclosure.

As used herein, the terms "fluidically connecting", "fluid communication", "fluidically coupled", and the like refer to two spatial regions being connected together such that a liquid or gas may flow between the two spatial regions. For example, a fluid area or compartment above a membrane with one or more nanopores embedded therein may be fluidically connected to a fluid area or compartment below the membrane, such that at least a portion of an electrolyte solution may transit between the connected fluid areas or compartments. The two spatial regions may be in fluid communication through a nanopore, or through one or more valves, restrictors, or other fluidic components that are to control or regulate a transit of ions through a system.

As used herein, the term "membrane" refers to a non-permeable or semi-permeable barrier or other sheet that separates two liquid/gel chambers (e.g., one on each side of the membrane) which can contain the same compositions or different compositions therein. The permeability of the membrane to any given species depends upon the nature of the membrane. In some examples, the membrane may be non-permeable to ions, to electric current, and/or to fluids.

For example, a lipid membrane may be impermeable to ions (i.e., does not allow any ion transport therethrough), but may be at least partially permeable to water (e.g., water diffusivity ranges from about 40 pm/s to about 100 pm/s). Any membrane may be used in accordance with the present disclosure, so long as the membrane can include a transmembrane nanoscale opening (e.g., a DNA nanopore) and can maintain a potential difference across the membrane. The membrane may be a monolayer or a multilayer membrane. A multilayer membrane includes two or more layers, each of which is a non-permeable or semi-permeable material.

The membrane may be formed of materials of biological or non-biological origin. A material that is of biological origin refers to material derived from or isolated from a biological environment such as an organism or cell, or a synthetically manufactured version of a biologically available structure (e.g., a biomimetic material).

An example membrane that is made from the material of biological origin includes a lipid bilayer. Suitable lipid bilayers include, for example, a membrane of a cell, a membrane of an organelle, a liposome, a planar lipid bilayer, and a supported lipid bilayer. Another example membrane that is made from the material of biological origin includes a monolayer formed by a bolalipid. A lipid bilayer can be formed, for example, from two opposing layers of phospholipids, which are arranged such that their hydrophobic tail groups face towards each other to form a hydrophobic interior, whereas the hydrophilic head groups of the lipids face outwards towards the aqueous environment on each side of the bilayer. Lipid bilayers also can be formed, for example, by a method in which a lipid monolayer is carried on an aqueous solution/air interface past either side of an aperture which is perpendicular to that interface. The lipid is normally added to the surface of an aqueous electrolyte solution by first dissolving it in an organic solvent and then allowing a drop of the solvent to evaporate on the surface of the aqueous solution on either side of the aperture. Once the organic solvent has at least partially evaporated, the solution/air interfaces on either side of the aperture are physically moved up and down past the aperture until a bilayer is formed. Other suitable methods of bilayer formation include tip-dipping, painting bilayers, and patch-clamping of liposome bilayers. Any other methods for obtaining or generating lipid bilayers may also be used.

A material that is not of biological origin may also be used as the membrane. Some of these materials are solid state materials and can form a solid state membrane, and others of these materials can form a thin liquid film or membrane. The solid state membrane can be a monolayer, such as a coating or film on a supporting substrate (i.e., a solid support), or can be a free-standing element. The solid state membrane can also be a composite of multilayered materials in a sandwich configuration. Any material not of biological origin may be used, as long as the resulting membrane can include a transmembrane nanoscale opening (e.g., a DNA nanopore) and can maintain a potential difference across the membrane. The membranes may include organic materials, inorganic materials, or both. Examples of suitable solid state materials include, for example, microelectronic materials, insulating materials (e.g., silicon nitride ($Si_3N_4$), aluminum oxide ($Al_2O_3$), hafnium oxide ($HfM_2$), tantalum pentoxide ($Ta_2O_5$), silicon oxide ($SiO_2$), etc.), some organic and inorganic polymers (e.g., polyamide, plastics, such as polytetrafluoroethylene (PTFE), or elastomers, such as two-component addition-cure silicone rubber), and glasses. In addition, the solid state membrane can be made from a monolayer of graphene, which is an atomically thin sheet of carbon atoms densely packed into a two-dimensional honeycomb lattice, a multi-layer of graphene, or one or more layers of graphene mixed with one or more layers of other solid state materials. The solid state membrane can be made by any suitable method. As examples, the graphene membrane can be prepared through either chemical vapor deposition (CVD) or exfoliation from graphite. Examples of suitable thin liquid film materials that may be used include, dioleoylphosphatidyl-choline (DOPC), diblock copolymers, and triblock copolymers, such as amphiphilic PMOXA-PDMS-PMOXA ABA triblock copolymers.

As used herein, the term "nanopore", "DNA nanopore", and "pore" are intended to mean a nanoscale opening or hollow, water-filled structure comprising nucleic acids, discrete from and extending across a membrane that separates two volumes and can permit, e.g., ions, organic molecules, and electric current to cross from one side of the membrane to the other side of the membrane. For example, a membrane that inhibits the passage of ions or water soluble molecules can include a nanopore structure that extends across the membrane to permit the passage (through a nanoscale opening/channel extending through the nanopore structure) of the ions or water soluble molecules from one side of the membrane to the other side of the membrane. The diameter of the nanoscale opening/channel can vary along its length (i.e., from one side of the membrane to the other side of the membrane), but at any point is on the nanometer scale (or nanoscale; e.g., from about 1 nm to about 50 nm, or about 1 nm to about 20 nm, to about 1 nm to about 10 nm). Examples of the nanopore include, for example, biological nanopores. A DNA nanopore can include, for example, a DNA origami (e.g., nanoscale folding of DNA to create the nanopore) or a double stranded nucleic acid (dsDNA) construct wherein the ions flow axially.

DNA nanopores according to embodiments of the present invention include membrane-spanning nanostructures that are embedded within a membrane in a manner akin to an eyelet mounted in a planar sheet material. Substituent nucleic acid pieces of a DNA nanopore can assume one or more shapes that, when combined, form a nanopore. For example, helices or helical bundles can be arranged side-by-side in a circular pattern to form a nanopore, where each bundle extends through the entire thickness of the membrane. In another embodiment, substituent nucleic acid pieces of the DNA nanopore may be circular or polygonal, where, when stacked akin to a stack of donuts, form a nanopore that extends through the entire thickness of the membrane. In yet another embodiment, two DNA strand helices can come together to form a DNA duplex that extends through the thickness of the membrane and acts as a DNA nanopore that forms a nanoscale ionic pathway though lacking a distinct hollow channel.

As used herein, the term "diameter" is intended to mean a longest straight line inscribable in a cross-section of a nanoscale opening through a centroid of the cross-section of the nanoscale opening. It is to be understood that the nanoscale opening may or may not have a circular or substantially circular cross-section. Further, the cross-section may be regularly or irregularly shaped.

As used herein, a "nucleotide" includes a nitrogen containing heterocyclic base, a sugar, and one or more phosphate groups. Nucleotides are monomeric units of a nucleic acid sequence. Examples of nucleotides include, for example, ribonucleotides or deoxyribonucleotides. In ribonucleotides (RNA), the sugar is a ribose, and in deoxyribonucleotides (DNA), the sugar is a deoxyribose, i.e., a sugar lacking a hydroxyl group that is present at the 2' position in ribose. The nitrogen containing heterocyclic base can be a purine base or a pyrimidine base. Purine bases include adenine (A) and guanine (G), and modified derivatives or analogs thereof. Pyrimidine bases include cytosine (C), thymine (T), and uracil (U), and modified derivatives or analogs thereof. The C-1 atom of deoxyribose is bonded to N-1 of a pyrimidine or N-9 of a purine. The phosphate groups may be in the mono-, di-, or triphosphate form. These nucleotides are natural nucleotides, but it is to be further understood that non-natural nucleotides, modified nucleotides or analogs of the aforementioned nucleotides can also be used.

As used herein "nucleic acid" refers to a polymer of two or more nucleotides and can exist, in embodiments, as a single stranded moiety, as a double stranded duplex, and/or as a triplex.

As used herein, the term "signal" is intended to mean an indicator that represents information. Signals include an electrical signal, which refers to an indicator of an electrical quality that represents information. The indicator can be, for example, current, voltage, tunneling, resistance, potential, conductance, capacitance, frequency, or other changes in an electrical waveform. "Electrical signal" also refers to a series of data collected on, e.g., current, impedance/resistance, or voltage magnitude, frequency and persistence over time.

As used herein, the term "event" refers to the transient binding of a target molecule to, e.g., an aptamer on the nanopore and its associated measurement via an electrical signal, e.g., change in current through the nanopore over time. It can be defined by its current, change in current from baseline, frequency of change, and duration of change, and/or other characteristics of detection of the molecule in the nanopore.

As used herein, an "area" of an event refers to the absolute value of the duration of an event (i.e., the duration the current deviates from an open channel current signal) multiplied by the average change in current from the open channel over the duration of the event (i.e., pA*ms). Area of an event can also refer to the cumulative value of multiple events over a fixed time, which incorporates frequency of events over time in addition to event magnitude and duration.

The term "substrate" refers to a rigid, solid support that is insoluble in aqueous liquid and is incapable of passing a liquid absent an aperture, port, or other like liquid conduit. In the examples disclosed herein, the substrate may have wells or chambers defined therein. Examples of suitable substrates can include glass and modified or functionalized glass, plastics (including acrylics, polystyrene and copolymers of styrene and other materials, polypropylene, polyethylene, polybutylene, polyurethanes, polytetrafluoroethylene (PTFE) (such as TEFLON® from Chemours), cyclic olefins/cyclo-olefin polymers (COP)(such as ZEONOR® from Zeon), polyimides, etc.), nylon, ceramics, silica or silica-based materials, silicon and modified silicon, carbon, inorganic glasses, and the like.

A "power supply" or "stimulus source" refers to an electronic device that is to provide a stimulus that causes ionic current to flow through the nanopore. In one example, the stimulus source may be a current source or a voltage source coupled to protodes/electrodes for each nanopore and associated membrane.

As used herein, the terms "well", "cavity" and "chamber" are used synonymously, and refer to a discrete feature defined in the device that can contain generally one, or in some embodiments more than one, stochastic sensor, including a base protode/electrode, a DNA origami including one or more anchoring linkers attached to the protode/electrode, to which the DNA nanopore is bound, a membrane incorporating the DNA nanopore that can adhere to one or more sides of the well, and a liquid, e.g., a buffer. The area below the membrane, i.e., the "cis well", is a chamber that contains or is partially defined by a base or cis protode/electrode, and is also fluidically connected to one or more areas above the membrane, i.e., the "trans wells" through one or more respective nanopores. Examples of an array of the present device may have one cis well or multiple cis wells. Each "trans well" is a chamber that contains or is partially defined by its above-membrane "trans electrode" and is also fluidically connected to one or more cis wells through one or more DNA nanopores. In some embodiments, each trans well can be electrically isolated from each other trans well or, in other embodiments, a common above-membrane, trans well is connected to and shared by more than one below-membrane cis well, each of which cis wells can be electrically isolated from other cis wells. In certain embodiments, a common (shared) above-membrane, trans well is connected to two or more below-membrane cis wells in which at least two cis wells are not electrically isolated (i.e., they share a protode). In some embodiments, each trans well is connected to a stimulus source, and optionally to an amplifier (e.g., Axopatch 200B amplifiers) to amplify electrical signals passing through respective nanopores. In other embodiments, the trans wells are connected to a single stimulus source which individually addresses the trans wells via multiplexing. Further, it is to be understood that the cross-section of a well, taken parallel to a surface of a substrate at least partially defining the well can be curved, square, polygonal, hyperbolic, conical, angular, and the like.

The term "DNA origami" refers to folding of 'scaffold' DNA template molecules (also "scaffold strands") into target structures at the nanoscale level, by annealing templates with rationally designed 'staple' DNA strands ("staple strands") through hybridization. The sequences of the staple strands are designed such that they hybridize to particular defined portions of the scaffold strands and, in doing so, these two components cooperate to self-assemble and force the scaffold strands to assume a particular structural configuration, such as a brick, donut, triangle, cylinder, and the like. DNA origami most commonly utilizes single-stranded DNA (ss-DNA), but it also can be formed using double stranded DNA (ds-DNA) and through formation of triplex DNA through Watson-Crick and Hoogsteen pairing. Therefore, term "DNA origami", as used herein, refers to each type (ss-DNA, ds-DNA, triplex DNA) separately, any two types combined, or all three. DNA origami may also refer to any organized structure built from nucleic acids other than DNA, including RNA, LNA, PNA, BNA or a combination thereof. The nucleic acids in a DNA origami may be homogeneous or heterogeneous (i.e.: all DNA; a combination of DNA and RNA and/or LNA, etc.).

Additionally, DNA origami is typically high yield (>99%), offers geometric homogeneity of the product, thermal stability in aqueous conditions, and also enables the high precision positioning of biomolecules (e.g., antibodies, proteins, metabolites, or small molecules) on the origami, to as low as 3.4 Å resolution, and the use of lithographic immobilization techniques (e.g., standard CMOS compatible techniques) on DNA origami.

Traditionally, assays to measure small molecule abundance and for observing dynamic biological processes can be assigned to one of two different classes, (i) ensemble measurements versus single molecule measurements, and (ii) single-plexed detection versus multiplexed detection. The application of these tools to bio-molecular quantification is dictated by the capabilities, advantages and limitations based on where they fall within these spectra (FIG. 2). As described herein, each class has shortcomings and challenges, which have a remedy in the embodiments of the disclosure.

Ensemble Measurements

Most biochemical processes are a result of thermal activations that result from molecular collisions that are stochastic in nature. Following the time course of collisions of a single molecule provides insights on its kinetic behavior and the reaction process. For a bulk system comprised of many molecules, bulk measurements of the processes yield average properties of the system. For example, 1 ml of a solution at 1 µM concentration contains more than $10^{14}$ solute molecules. Consequently, when time properties are measured in bulk, they contain the asynchronous contributions of all molecules in the ensemble, and information about distributions in molecular properties is lost. This yields the average behavior of the system, which is not necessarily representative of the physical behavior of any single molecule in the ensemble. Nevertheless, ensemble measurements are tend to be easy to implement, and observing average property changes of a large population of molecules can reveal useful information about some phenomena, such as the rate of formation of product in a chemical reaction, thermal conductivity, or viscosity of the system.

Multiplexed Ensemble Measurements

For a simple binary, non-specific single molecule sensor (S) that can reversibly and weakly interact with a target (T) to switch between "on" (active state, bound) and "off" (inactive state, unbound). The binding affinity of a target molecule with the sensor is described by its corresponding equilibrium dissociation constant ($k_D$). For a sensor that is weakly receptive to a wide variety of markers with varying affinities, measuring the ($k_D$) values enables identification of the markers and therefore can be used to distinguish them.

$$S + T \underset{k_{off}}{\overset{k_{on}}{\rightleftharpoons}} S \cdot T \tag{0}$$

$$k_D = \frac{k_{off}}{k_{on}} = \frac{[S][T]}{[S \cdot T]}$$

Bulk Detection of One Variety of Target Molecules

For a detector pad that contains a number of identical single molecule sensors, if a target molecule of some unknown concentration ($C_x$) is introduced onto the detector pad, the signal detected from the pad (I) is a commutation of the signal from each of the individual sensors (i) in interaction with the target molecules. Therefore, the ensemble signal from the pad is an average of signal from all the sensors. The detector pad has limited resolution in signal due to presence of various sources of noise such as thermal fluctuations, non-specific interactions, and vibrations. Therefore, while each individual binding-unbinding event cannot be detected due to noise and averaging, the cumulative signal produced by a number of sensors is measurable. For a system in equilibrium, the detector measures the mean signal produced by the batch of sensors on the pad. The mean signal is in fact proportional to the total number of sensors on the pad and the probability of a sensor interacting with the target.

Number of sensors on the detector pad=n

Signal from each stochastic sensor=i

Probability of turning a sensor on=$P_{on}$

Concentration of a single variety of target in the sample= [T]

Mean signal=$\bar{I} \propto n*I*P_{on}$ $$\bar{I} \propto \frac{n*i*[T]}{k_D} \qquad (1)$$

By directly measuring the ensemble average signal for a given detector pad, we obtain a relation between the concentration of the target [T] and its $k_D$ with the sensor elements given by equation (1). If the identity of the target is unknown, i.e., $k_D$ is unknown, for dilute concentrations, it is possible to use multiple known concentrations of the target to reveal its unique signature, even when exact number of sensors on the pad, n, is unknown. For example, binding curves and fraction bound plots generated from titration experiments measure binding affinity values using this technique. However, if the identity of the target is known, i.e., if $k_D$ is known, but the concentration of the target in the sample i.e., [T] is unknown, then using the average bulk signal $\bar{I}$ measured in equilibrium, the relative concentration of the marker can be obtained with respect to a previously calibrated value. However, because of the averaged ensemble of many single sensor events, any information regarding number of active sensors at an instant or the change in their activity is lost in the bulk signal noise limited by resolution. Therefore, while relative changes in the concentration of the target [T] can be quantified in equilibrium, information regarding instantaneous changes is lost in the system noise. Therefore, measuring I does not yield an instantaneous real time profile of the sample.

While the variance of the signal, $\sigma^2$, sensed by the detector pad over time can also be observed from the signal readout from the pad, it is not directly evident how much of the variance arises from noise such as thermal fluctuations, non-specific interactions, external disturbances, etc. Thus, no meaningful information can be extracted reliably from measuring the variance of the signal from bulk detection.

Bulk Detection of Several Varieties of Target Molecules with a Mixture of Different Types of Sensing Elements When multiple targets are exposed to a mixture of unique sensing elements on the detector pad (assuming that the $k_D$ values are distinct for each unique target), the mean signal sensed by the detector pad is an amalgamation of the active sensor signals arising from the equilibration of the set of targets with the batch of sensors. Let us assume that these unique sensors are cross-reactive such that each sensing element is receptive to a wide variety of target molecules and produces a unique signal ($i_{pq}$) for a target p interacting with the sensor q. The cumulative signal detected by the pad is a sum of the individual signals $i_{pq}$ produced by each unique sensor.

In this case, the mean signal I from the pad is a summation of individual signals from each of the distinct sensing elements $I_q$. For every sensor element q, the average signal in equilibrium $I_q$ is given by equation (3). This is dependent on the cumulative signals arising from interaction of each target p with the $q^{th}$ sensing element. This is dictated both by the individual sensor-target interactions $(k_D)_{pq}$ and the individual target concentrations in the sample $[T]_p$.

$$\bar{I} = \sum (i_{pq}) \text{ for } q = 1 \text{ to } n \text{ and } p = 1 \text{ to } m \qquad (2)$$

Where $$\bar{T_q} \propto \sum \left( \frac{[T]_p}{(k_D)_{pq}} \right) \text{ for } p = 1 \text{ to } m \qquad (3)$$

Here each unique sensor can produce an analog signal $a_{pq}$ that depends on the strength of interaction between the sensor and the target molecule. Therefore, equation 3 reduces to follows:

$$\text{Where } \bar{T_q} = \sum \left( \frac{a_{pq}[T]_p}{(k_D)_{pq}} \right) \text{ for } p = 1 \text{ to } m \qquad (4)$$

$$(5)$$

$$[\bar{I_1}\ \bar{I_2}\ \bar{I_3}\ ...\ \bar{I_n}] =$$

$$[[T]_1\ [T]_2\ ...\ [T]_m]* \begin{bmatrix} \frac{a_{11}}{(k_D)_{11}} & \frac{a_{12}}{(k_D)_{12}} & \cdots & \frac{a_{1n}}{(k_D)_{1n}} \\ \frac{a_{21}}{(k_D)_{21}} & \frac{a_{22}}{(k_D)_{22}} & \cdots & \frac{a_{2n}}{(k_D)_{2n}} \\ \frac{a_{31}}{(k_D)_{31}} & \vdots & \cdots & \frac{a_{3n}}{(k_D)_{3n}} \\ \vdots & \vdots & \ddots & \vdots \\ \frac{a_{m1}}{(k_D)_{m1}} & & \cdots & \frac{a_{mn}}{(k_D)_{mn}} \end{bmatrix}$$

$$\bar{I} = \sum (\bar{T_q}) \text{ for } q = 1 \text{ to } n \qquad (6)$$

In this case, if the target identities are known, i.e. $(k_D)_{pq}$ are known, but the concentrations are unknown, then we have (pq+p) unknowns while we have q equations available. Here, it is impossible to predict the exact concentrations of all the targets simultaneously. The only case when a direct evaluation of either the concentration or the dissociation constant (i.e., the identity) of the targets is uniquely possible is when the sensor elements interact selectively with only a single target and remain unaffected by the rest of the targets. That is indeed the case of singleplexed ensemble detection techniques such as ELISA where highly selective antibody targets are used.

However, for unique sensor elements that weakly interact with a variety of targets in the mixture, it is analytically impossible to measure the concentrations of each of the targets directly from the cumulative signals of each sensor, even if the target identities are known beforehand. One advantage of the cross-reactive construct however is that data in a high-dimensional feature space are obtained. As the dimensionality increases, the cross-reactivity increases the amount of data and hence probability of decoding the sensor identities increases. If n≥m, when, e.g., identifying a limited set of proteins rather than their proteoforms, the data can be evaluated using kernel-based machine learning methods such as Support Vector Machines (SVMs) in high dimensional feature space to perform linear inference using Mercer's Theorem. Hyperplanes that separate the data in high dimensional space can be predicted for target classification. Nevertheless, sensor-based ensemble methods fail when quantification of single or multiple targets is required in addition to target classification.

Thus, in ensemble measurements, the signals measured are unsynchronized contributions of the individual interactions. Because the detector pad is in constant interaction with the environmental thermal bath, the information embedded in individual stochasticity of single sensor events was lost in the noise of random thermal fluctuations. Thus, in general, a detector pad with many single molecule sensors under equilibrium cannot distinguish between only one type of target, mixture of non-reacting targets or a mixture of reacting targets. In addition, this system also fails at measuring instantaneous changes in the mixture as the signals observed by the pad are an ensemble average and the instantaneous changes at each sensor are masked by inherent measurement noise.

Single Molecule Measurements

The best available resolution, without the need for calibration, is at the single molecule level. Single molecule methods are attractive and powerful for the study of complex biological and chemical systems and processes due to their unique abilities to probe molecular structure, dynamics and function, unhindered by the averaging inherent in ensemble experiments. Unlike in ensemble measurements where the individual events cannot be distinguished, single molecule methods allow detection of rare events and remove the need for synchronization of many single molecules undergoing a time-dependent process. In addition, single molecule methods facilitate real-time and enhanced quantification of biomarkers compared to the standard immunoassays, and therefore enable rapid understanding of normal and pathological processes of clinical relevance.

Single molecule measurements become necessary when a mixture of multiple target molecules need to be sensed and quantified simultaneously in a complex sample with large variations in abundance of molecules. At the single-molecule level, signals display random and stochastic dynamics because the steps of a chemical reaction generally involve thermally induced, random crossing of a free energy barrier of the interaction. Analytical intensities of these random interactions provide insights into how the complexes form and thus are indicative of the signature or identity of the molecule. Therefore, by measuring the signal intensities from many single molecule sensors, it is possible to decompose the signatures of a variety of targets in a mixture. If the detector pad had only a single sensor, i.e., the detector measured the signal when a single molecule of the target interacted with the sensor element, then in principle we could distinguish the presence of a variety of targets based on the unique signal intensity.

However, if one wanted to use the single molecule tools to measure the bulk characteristics of a population of targets such as concentration, e.g., $k_{on}$, one would need several copies of such single molecule sensors such that the number of sensors is much more than the saturation limit of each variety of target. So, in principle if one needs 1000 single molecule sensors to overcome the saturation limits and measure the concentration of one target, one will need at least $10^6$ sensors to measure the concentrations of 1000 targets simultaneously, assuming that the targets concentrations in a similar dynamic range in the mixture. If the dynamic range varies over several orders of magnitude, for example as in the case of immunoglobulin which exists in tens of mg/dL in human serum compared to cytokines, which exist at few pg/dL, one will need at least $10^{12}$ sensors to accurately measure the concentrations of these two target molecules. Therefore, using single molecule methods presents a problem of multiplexing and scaling, especially when simultaneous detection at single molecule level and quantitative measurement at ensemble level are desired.

This fundamental limitation of single molecule measurements can be resolved by adding a temporal dimension to the measurements such that dynamic changes are observable within the measurement window. While the signal amplitude provides structure specific information sufficient for target identification, the distribution of lifetimes for each target further characterizes the mechanism and provides information of dynamical properties of the population of targets. Thus, a single copy of single molecule sensor in principle is capable of multiplexed sensing of a variety of targets given sufficiently long measurement window. However, this may not be practical for complex biological samples quantification, for example quantifying 1 million proteins in human blood.

Stochastic Measurements are Necessary for Multiplexed Quantification

A stochastic sensor is a single molecule sensor with a reasonably measurable sensor-target complex lifetime. In its simplest form, it is a single molecule sensor with an added dimension of time such that it can exist in one of two states, each with its unique signal-occupied by the target or unoccupied by the target. Unlike a generic singe molecule sensor such as electrochemical, colorimetric, spectrophotometric, or antibody recognition, a stochastic sensor can have a rapid and reversible response to the presence or absence of a target molecule making it feasible to monitor dynamic changes in binding events and target concentration. For example, monitoring dynamic events such as protein-protein interactions, peptide cleavage and protease activity is possible only through stochastic sensing. Stochastic sensors are also active over a wide range of concentrations. As opposed to monitoring a single parameter such as signal intensity, a stochastic sensor allows higher dimensional measurements such as dwell time of how long the target interacts with the sensor and the frequency of occurrence of the fluctuations. These parameters facilitate its use in simultaneous identification of target signatures as well as estimation of bulk properties such as concentration. Since each target produces a characteristic signal, the sensor element itself need not be highly selective or unique to a target, thereby reducing the engineering complexity for varied applications. This capability allows for multiplexed sensing. In addition, fouling of the sensor does not produce an inaccurate measurement as the signal generated from fouling does not match the signature of the target. Thus, stochastic sensing allows accurate measurement even at low target concentrations without loss of signal to noise.

In stochastic sensing, the signals of a single sensor appear as square pulses of random duration, as sensor-target complexes form and dissociate. The event frequencies of a specific sensor turning "on" and "off" in presence of a specific target molecule are defined by their unique rate constants. The ratio of the rate constants gives the equilibrium constant. The values of the rate constants and their ratio correlate to the height of the energy barriers for the reactions and the difference in free energy between the two states. At steady-state, i.e., at a fixed target concentration, the sensor has a constant probability of exiting its current state. Since this process follows Poisson statistics, the sensor's lifetime in each state is exponentially distributed, comparable to lifetimes during the radioactive decay. The mean lifetime of a state is the reciprocal of the sum of the rate constants for exiting that state. That is, for two states such as on and off, by measuring the mean duration of on events we could obtain the rate constant for going from on to off state, and vice versa.

From the temporal distributions, for mean on time, $T_{on}$ and mean off time, $T_{off}$ observed during the experimental record, the relations to the rate constants and free target concentration in equilibrium [T] are given by:

$$T_{on} = \text{mean on time} = \frac{1}{k_{off}} \quad (7)$$

$$T_{off} = \text{mean off time} = \frac{1}{k_{on}[T]} \quad (8)$$

$$\frac{T_{off}}{T_{on}} = \frac{k_{off}}{k_{on}[T]} = \frac{k_D}{[T]} \quad (9)$$

$$[T] = \frac{k_D T_{on}}{T_{off}} \quad (10)$$

The unbinding event rate $k_{off}$ is independent of the target concentration, as expected for a first-order reaction. Hence, by measuring the mean on time, $k_{off}$ can be directly determined. In contrast, $k_{on}$ is dependent on both the mean off time and target concentration, and is also directly proportional to the frequency of binding events. A common approach to determine the exact target concentration in single molecule experiments is to first evaluate the $k_D$ by plotting the ratio of mean event lifetimes of the sensor on and off states at various target concentrations. Target concentrations in the sample could be varied through steps of sequential dilution. Then using equation (10), the exact target concentration in the original sample can be estimated. An alternative approach relies on the signal intensities instead of the information from time trace for estimating the $k_D$. For a complex biological sample, the experimental record of a single sensor can be differentiated to be associated with individual targets based on the signal intensities. The intensity changes between on and off state of the extracted signal trace for a single target can be examined to evaluate the $k_D$. For a single target trace with a mean on signal of $I_{on}$, mean off signal of $I_{off}$, and an averaged signal of $I$ over the entire duration of observation, $k_D$ can be evaluated based on an alternative interpretation of equation (9). This method is particularly suitable for experiments involving low time resolution or short observation periods.

$$\bar{I} = \frac{T_{on}}{T_{on} + T_{off}} I_{on} + \frac{T_{off}}{T_{on} + T_{off}} I_{off} \quad (11)$$

$$\frac{T_{on}}{T_{off}} = \frac{\bar{I} - I_{off}}{I_{on} - \bar{I}} \quad (12)$$

$$[T] = \frac{\bar{I} - I_{off}}{I_{on} - \bar{I}} k_D \quad (13)$$

In theory, a generic stochastic sensor can be either a digital sensor or an analog sensor. A digital sensor exhibits a single on and single off state in presence of a target molecule, irrespective of the complexity of interaction between the target and the sensor. They possess advantages such as high signal to noise, ease of design and lack of necessity for instrument resolution. However, a digital sensor is not capable of distinguishing multiple stages of on or off states that the target-sensor complex undergoes and only produces a binary signal trace. Therefore, the time constants are no longer reflections of single rate constants but arise from matrix multiplication of rate constants of a subset of the states. Approaches developed for single cell patch clamp recordings have extensively dealt with the complexity of digital stochastic sensing, and algorithms for fitting rate constants that maximize the likelihood of observed experimental records have been developed. However, in a multiplexed environment, digital sensors can lack the richness of information contained in an analog equivalent and involve mathematical complexity in distinguishing various states of a single target-sensor complex from multiple target interactions.

Analog sensors can distinguish the presence of multiple stages of multiple states for a single target-sensor complex, provided the measuring instrument if capable of enough resolution in signal and time. Signals corresponding to multiple targets can be deconvolved based on their amplitude and sequence in conjunction with the time trace. Further, due to the additional dimension of amplitude, multiplexed measurements are less complex to interpret and more accurate. A key challenge is designing stochastic sensors that are capable of producing differential signals to subtle changes in conformation of the sensor-target complex and choosing a detection method that is capable of dynamic readouts, a challenge addressed by the aspects and embodiments of the disclosure.

Thus, in contrast to common assays that typically rely on high affinity, tight binding of a probe (e.g., antibody) to an analyte target in a sample, or rely on the above described methodologies that each lack one or more attributes necessary to accomplish the quantitative processes described herein, the present disclosure describes that to realize highly parallel stochastic measurements in a dynamic and high throughput readout system, each binding event between aptamer and target should be weak or relatively weak (low affinity) and of low specificity. That is, as described herein, to recognize a variety of targets and to enable dynamic readout of changes in concentration in a reasonably small (temporal) sampling window, a plurality of binding-unbinding events need occur on a sensor, which is made possible when the sensor is a weak binder and is receptive to a wide variety of targets. Such sensors, when exposed to a sample, generate a characteristic electrical signal with temporal attributes governed by the interaction between the sensor and a molecule. The collective signals across an array of nanosensors are analyzed dynamically by a machine learning algorithm to reveal the unique signatures of the molecules in the sample, schematically shown in FIG. 1.

Sensor cross-reactivity is desirable due to the need for increased dimensionality for unsupervised pattern recognition for a fixed set of data, such as for a fixed number of stochastic sensors, such as in a sensor array. That is, the predictive power of a classifier increases as the number of dimensions increase up to a limit, beyond which performance deteriorates. Thus, having weakly cross-reactive sensors that interact with multiple targets in the solution increases the features that describe a particular target, enabling techniques such manifold hypothesis, feature selection via correlations or random forests and feature extraction via Principal Component Analysis, or t-Distributed Stochastic Neighbor Embedding to be used to increase the data depth. For example, relevant additional dimensions can increase contrast and close neighbors can be discerned from far neighbors as long when the signal-to-noise ratio is high. At least as importantly, cross-reactivity increases the multiplexing capability, since as a small number of sensors can yield highly dimensional data about multiple targets rather than information about one target.

Therefore, novel devices for sensing one or more targets in a sample with an array of unique single molecule sensors that include synthetically constructed DNA nanopores precisely organized on a bioprotonic nanopore protodes/electrodes (e.g., palladium hydride), are provided herein, as well as methods for using and fabricating such devices. Such devices are also referred to herein as "bioprotonic sensors" or "bioprotonic devices". Embodiments of this tool address limitations of other proteome quantification techniques by relying on the capabilities of DNA origami, such as atomically precise placement, seamless biotic-abiotic interface with lipid bilayer (LBL) and Complementary Metal-Oxide Semiconductor (CMOS) electrodes, molecular programmability based on the proteins to be sensed, self-assembly and scalability for high throughput arrangements. Using an array of these bioprotonic nanopore electrodes enables a pattern-recognition based protein quantification platform to be developed. Further, each nanopore can be explicitly modified to have a non-covalent binding site to enable differential biochemical selectivity to various molecules of interest. Depending on the identity and concentration of proteins present in the solution, each individual sensing element interacts transiently with protein(s) and produces a characteristic temporal signature. The collective temporal response from the array will serve as a unique signature of the mixture of targets. The weak and reversible binding not only renders this sensing platform label free but also enables continuous real time quantification of change in molecular composition using the same planar array. Based on collection of data from a training set, it is possible to analyze and uniquely identify the concentration of individual molecules dictating the signal.

In one aspect, a device for sensing one or more targets in a sample is provided, including an array of two or more stochastic sensors, wherein each sensor interacts weakly with a determinant on the target; a means for capturing electrical signals from each sensor and the temporal duration of each signal; and a means for analyzing the cumulative signals from the array of stochastic sensors.

In some embodiments of the device for sensing one or more targets in a sample, the means for capturing electrical signals from each sensor and the temporal duration of each signal includes a power supply in electrical contact with each stochastic sensor to provide an electric potential difference across the stochastic sensor; and a detector to detect changes in electrical signal through the nanopore over time as each sensor interacts with one or more targets. In some embodiments, a signal amplifier is optionally included. Electrical signal changes detected by a detector can include changes in signal magnitude/amplitude, signal duration and frequency of signal changes.

For example, a target that transiently binds stochastic sensor may totally occlude the nanopore channel, preventing, e.g., proton flow through the channel. Such a binding event would produce a signal (i.e., a drop in current) of a large magnitude when compared to a target transiently binding a stochastic sensor that only partially occludes the nanopore channel, which would allow some level of continued current flow. Signal duration is representative of the length of the association event between a target and, e.g., an aptamer on the nanopore. Longer residence time yields a longer signal duration. Signal frequency (when considering a signals of like magnitude and duration, indicating the same target is repeatedly binding) is indicative of the number of binding events. A higher signal frequency per unit time indicates a greater number of binding and dissociation events occurring per unit time.

In some embodiments of the device for sensing one or more targets in a sample, the means for analyzing the cumulative signals from the array of stochastic sensors includes a processing system; computer storage accessible to the processing system, and computer program instructions encoded on the computer storage, wherein when the computer program instructions are processed by the processing system, the computer system is configured to: define data structures in the computer storage representing target molecules; and execute a machine learning program applied to the data structures to identify targets reacting with the sensors of the device, and quantify the targets reacting with the sensors of the device.

In some embodiments, one or more computers can be used to implement such a computational pipeline (i.e., analyze the cumulative signals from the array of stochastic sensors, define data structures in the computer storage representing target molecules; execute a machine learning program applied to the data structures to identify targets reacting with the sensors of the device, and quantify the targets reacting with the sensors of the device), using one or more general-purpose computers, such as client devices including mobile devices and client computers, one or more server computers, or one or more database computers, or combinations of any two or more of these, which can be programmed to implement the functionality such as described in the example implementations.

Figure 7:
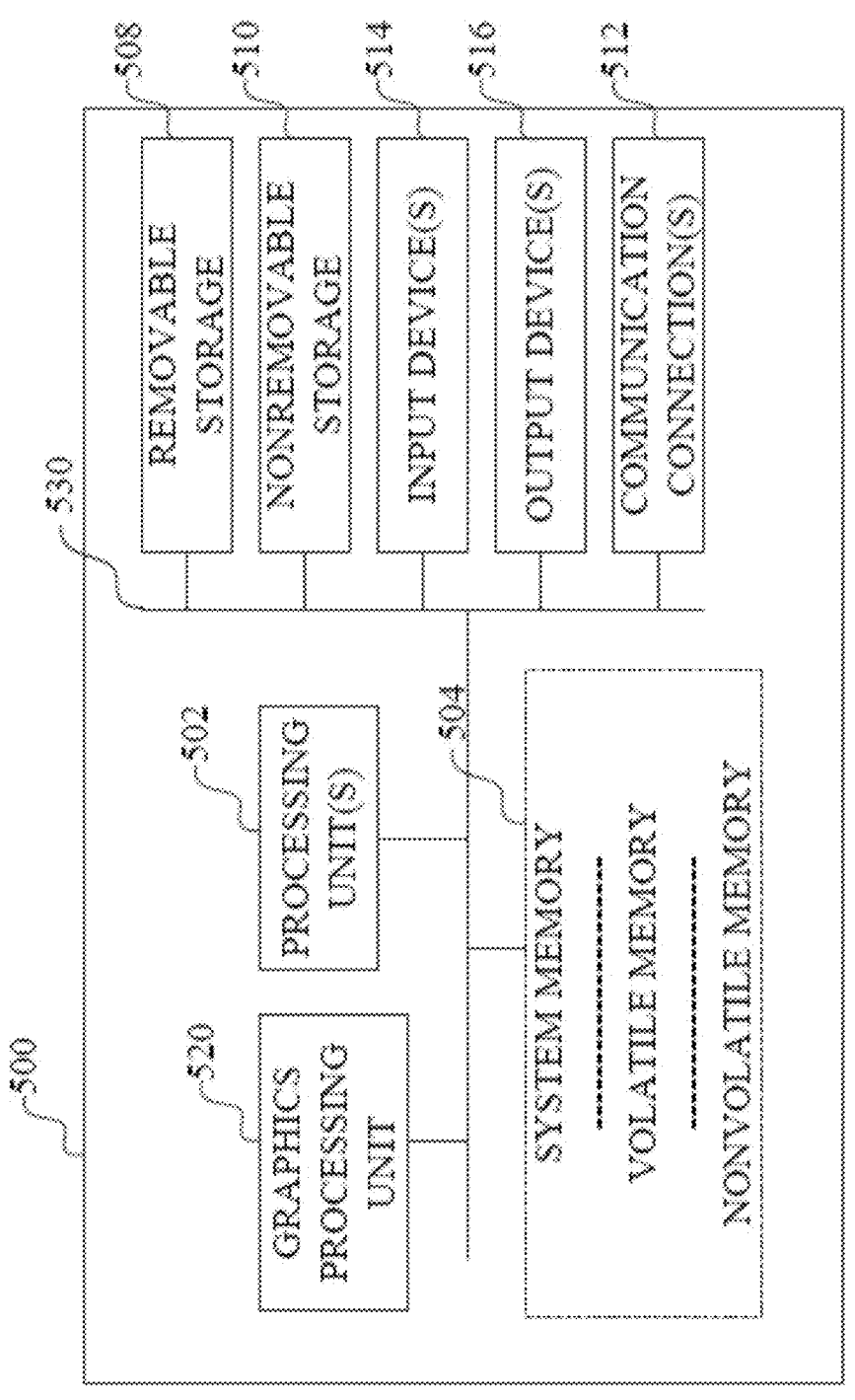
FIG. 7 is a block diagram of a general-purpose computer which processes computer programs using a processing system.

FIG. 7 is a block diagram of a general-purpose computer which processes computer programs using a processing system. Computer programs on a general-purpose computer generally include an operating system and applications. The operating system is a computer program running on the computer that manages access to resources of the computer by the applications and the operating system. The resources generally include memory, storage, communication interfaces, input devices and output devices.

Examples of such general-purpose computers include, but are not limited to, larger computer systems such as server computers, database computers, desktop computers, laptop and notebook computers, as well as mobile or handheld computing devices, such as a tablet computer, handheld computer, smart phone, media player, personal data assistant, audio and/or video recorder, or wearable computing device.

With reference to FIG. 7, an example computer 500 comprises a processing system including at least one processing unit 502 and a memory 504. The computer can have multiple processing units 502 and multiple devices implementing the memory 504. A processing unit 502 can include one or more processing cores (not shown) that operate independently of each other. Additional co-processing units, such as graphics processing unit 520, also can be present in the computer. The memory 504 may include volatile devices (such as dynamic random-access memory (DRAM) or other random-access memory device), and non-volatile devices (such as a read-only memory, flash memory, and the like) or some combination of the two, and optionally including any memory available in a processing device. Other memory such as dedicated memory or registers also can reside in a processing unit. Such a memory configures is delineated by the dashed line 504 in FIG. 1. The computer 500 may include additional storage (removable and/or non-removable) including, but not limited to, solid state devices, or magnetically recorded or optically recorded disks or tape. Such additional storage is illustrated in FIG. 7 by removable storage 508 and non-removable storage 510. The various components in FIG. 7 are generally interconnected by an interconnection mechanism, such as one or more buses 530.

A computer storage medium is any medium in which data can be stored in and retrieved from addressable physical storage locations by the computer. Computer storage media includes volatile and nonvolatile memory devices, and removable and non-removable storage devices. Memory 504, removable storage 508 and non-removable storage 510 are all examples of computer storage media. Some examples of computer storage media are RAM, ROM, EEPROM, flash memory or other memory technology, CD-ROM, digital versatile disks (DVD) or other optically or magneto-optically recorded storage device, magnetic cassettes, magnetic tape, magnetic disk storage or other magnetic storage devices. Computer storage media and communication media are mutually exclusive categories of media.

The computer 500 may also include communications connection(s) 512 that allow the computer to communicate with other devices over a communication medium. Communication media typically transmit computer program code, data structures, program modules or other data over a wired or wireless substance by propagating a modulated data signal such as a carrier wave or other transport mechanism over the substance. The term "modulated data signal" means a signal that has one or more of its characteristics set or changed in such a manner as to encode information in the signal, thereby changing the configuration or state of the receiving device of the signal. By way of example, and not limitation, communication media includes wired media such as a wired network or direct-wired connection, and wireless media include any non-wired communication media that allows propagation of signals, such as acoustic, electromagnetic, electrical, optical, infrared, radio frequency and other signals. Communications connections 512 are devices, such as a network interface or radio transmitter, that interface with the communication media to transmit data over and receive data from signals propagated through communication media.

The communications connections can include one or more radio transmitters for telephonic communications over cellular telephone networks, and/or a wireless communication interface for wireless connection to a computer network. For example, a cellular connection, a Wi-Fi connection, a Bluetooth connection, and other connections may be present in the computer. Such connections support communication with other devices, such as to support voice or data communications.

The computer 500 may have various input device(s) 514 such as a various pointer (whether single pointer or multi-pointer) devices, such as a mouse, tablet and pen, touchpad and other touch-based input devices, stylus, image input devices, such as still and motion cameras, audio input devices, such as a microphone. The compute may have various output device(s) 516 such as a display, speakers, printers, and so on, also may be included. These devices are well known in the art and need not be discussed at length here.

The various storage 510, communication connections 512, output devices 516 and input devices 514 can be integrated within a housing of the computer, or can be connected through various input/output interface devices on the computer, in which case the reference numbers 510, 512, 514 and 516 can indicate either the interface for connection to a device or the device itself as the case may be.

An operating system of the computer typically includes computer programs, commonly called drivers, which manage access to the various storage 510, communication connections 512, output devices 516 and input devices 514. Such access generally includes managing inputs from and outputs to these devices. In the case of communication connections, the operating system also may include one or more computer programs for implementing communication protocols used to communicate information between computers and devices through the communication connections 512.

Any of the foregoing aspects may be embodied as a computer system, as any individual component of such a computer system, as a process performed by such a computer system or any individual component of such a computer system, or as an article of manufacture including computer storage in which computer program code is stored and which, when processed by the processing system(s) of one or more computers, configures the processing system(s) of the one or more computers to provide such a computer system or individual component of such a computer system.

Each component (which also may be called an "engine" or "computational model" or the like), of a computer system such as described herein, and which operates on one or more computers, can be implemented as computer program code processed by the processing system(s) of one or more computers. Computer program code includes computer-executable instructions and/or computer-interpreted instructions, such as program modules, which instructions are processed by a processing system of a computer. Generally, such instructions define routines, programs, objects, components, data structures, and so on, that, when processed by a processing system, instruct the processing system to perform operations on data or configure the processor or computer to implement various components or data structures in computer storage. A data structure is defined in a computer program and specifies how data is organized in computer storage, such as in a memory device or a storage device, so that the data can accessed, manipulated, and stored by a processing system of a computer.

In some embodiments of the devices of this and other aspects, each stochastic sensor in the array is unique. Likewise, across aspects of the disclosure, in some embodiments of the device the array is a planar array, wherein "planar" can include curved surfaces (e.g., a cylindrical surface) and surfaces of three-dimensional shapes (e.g., pyramidal structures). Non-planar arrays are also contemplated herein. Planar arrays are a favorable configuration where a large number of single molecule sensing events are to be addressed individually while being spatially resolved. A planar array format typically also allows for discrete spaces to be more easily fabricated or modified to produce a multi-functional array capable of multiplexed quantification, as well as integration into, e.g., a microfluidic or other continuous flow apparatus whereby sequential flow of different target mixtures can invoke corresponding temporally separated responses from the same set of sensors. Planar arrays are also amenable to incorporating advances in optics, microelectronics, and force-based methods to spatially resolve single molecule events.

In another aspect, a device for sensing one or more targets in a sample is provided, including (i) a bioprotonic conducting material forming a planar array of protodes on a non-conducting substrate; (ii) a plurality of DNA origami tethered DNA nanopores immobilized to the planar array of protodes, wherein the outer surface of the DNA nanopore comprises one or more hydrophobic moieties; (iii) an insulating membrane, defining a space inferior (below or "cis") to the membrane and a space superior (above or "trans") to the membrane, wherein a DNA nanopore spans the membrane and provide an ionic pathway between the bioprotonic conducting material inferior to the membrane and bulk solution; (iv) a power supply in electrical contact with each protode to provide an electric potential difference across the membrane; and a detector to detect changes in electrical signal through the nanopore over time as each nanopore interacts with one or more targets, in which electrical signal changes can comprise changes in signal magnitude, signal duration and frequency of signal changes.

In embodiments of this and other aspects, the bioprotonic conducting material forms an "electrode" in the compartment below, or cis, to the membrane. A complementary protode/electrode is provided in the compartment above, or trans, to the membrane such that an electrical potential and proton flow can be generated across a DNA nanopore, perturbation of which are measured herein.

In some embodiments of this and other aspects, the DNA nanopores comprise one or more target binding moieties, one or more target binding linkers, or combinations thereof. Target binding moieties include aptamers designed, synthesized, isolated, and/or selected that interact weakly with one or more determinants (e.g., binding sites) on the one or more targets. Aptamers can include, e.g., DNA, RNA, XNA, peptides, or combinations thereof. Nucleic acid aptamers can also be designed, synthesized, isolated, and/or selected to bind (anneal) to specific locations in the DNA nanopore, i.e., include staple strand-like sequences. Such sequences can be included during initial aptamer synthesis and participate in the selection process (e.g., by SELEX), or appended, e.g., by de novo synthesis or amplification of a pool of suitable aptamers isolated during a selection process. Such aptamers, though anchored on the surface of a DNA nanopore by their staple strand-like sequence, protrude from the surface of the DNA nanopore and reside in solution near the DNA nanopore channel opening able to interact with one or more targets. In some embodiments, one or more target binding moieties on a DNA nanopore can be the same as one or more nanopore anchoring moieties located on the opposite end of the DNA nanopore. In some embodiments, the target binding moieties on a DNA nanopore are the same as the nanopore anchoring moieties located on the opposite end of the DNA nanopore.

In some embodiments, DNA nanopores include one or more target binding linkers. Target binding linkers are distinct from target binding moieties like the aptamers described above in that they are not intended to bind directly to one or more targets in a sample. Rather, they bind to the surface of a DNA nanopore and provide a sequence or chemical moiety that can bind to or react with a separate molecule that serves as a target binding moiety. Target binding linkers can be designed to bind to specific locations in the DNA nanopore, and in some embodiments, such linkers include staple strands that, in addition to hybridizing with sequences in the DNA nanopore for precise location, can hybridize to complementary sequences attached to one or more separate moieties that serve as target binding moieties, or, in some embodiments, chemically react or otherwise bind to one or more separate moieties that serve as target binding moieties to create a target binding linker-target binding moiety conjugate. For example, a linker-binding moiety pair can be linked by click chemistry by reacting one half of the pair with a dibenzocyclooctyne (DBCO), amine or thiol moiety attached to the other half of the pair with a complementary azide, ester or maleimide moiety, respectively, attached. As a specific illustrative example of the concept, a target binding linker attached to biotin could be used to bind to a streptavidin target, though such an interaction is of an affinity higher than relevant for the aspects and embodiments of the disclosure. Thus, in embodiments, DNA nanopores include one or more target binding moieties that include a DNA nanopore binding or staple strand-like sequence. In some embodiments, DNA nanopores include one or more target binding linkers or target binding linker-binding moiety conjugates, and in some embodiments, DNA nanopores include combinations thereof.

In embodiments of this and other aspects, DNA nanopores can be formed or constructed from one or more DNA origami modules, or pieces of a complete nanopore. In some embodiments, the nanopore can be formed from an arrangement of modules that forms a higher order shape, frame or framework (e.g., six similar or identical DNA origami helical bundle modules formed in a circle with the long axis of each helical bundle module parallel to the others). In some embodiments, the modules of the frame are supported or connected by additional submodules that connect the modules to lock in or set the higher order shape. Typically, at least part of a module is intended to form at least part of the membrane-spanning portion of the DNA nanopore, though, in some embodiments the DNA nanopore can include a membrane spanning portion and a cap structure that sits on the portion of the membrane spanning portion that is superior to (above) the membrane. In such embodiments, modules and submodules can be formed by typical DNA origami processes from scaffold DNA and staple DNA. Individual modules can be joined by DNA strands, the DNA strand either being integral with the module, or hybridized to each module.

The three-dimensional configuration of DNA nanopores of the disclosure define a channel that spans the membrane, with the channel having a lumen that has a minimum internal width of at least about 1 nm. Nanopores of the disclosure have a single channel located at least substantially centrally in the nanopore structure when viewed perpendicular to the plane of the membrane. The cross-sectional profile of the lumen parallel to the plane of the membrane may be circular, ellipsoidal, polygonal or irregular, and may vary in terms of the internal dimensions. In some embodiments, the channel has a consistent internal profile and size for its entire length, and in embodiments, the cross-sectional profile of the channel is a circle or a quadrilateral in the form of a square, rectangle or trapezoid. In some embodiments, the minimum opening diameter of the channel is suitable to allow passage of a proton. Typically, the minimum opening is about 1 nm, 2 nm, 3 nm, 4 nm, 5 nm, 6 nm, 7 nm, 8 nm, 9 nm, 10 nm, 11 nm, 12 nm, 13 nm, 14 nm, or 15 nm or more. In some embodiments, the lumen is between about 1 nm and around 10 nm in width, and in some embodiments between about 10 nm and around 20 nm in width. The maximum opening of the channel is limited by the need to maintain structural integrity of the pore and to obtain an electrical read-out when a molecule of interest (proton or otherwise) passes through. In embodiments, the maximum opening of the channel (i.e. minimum constriction) is about 100 nm, 75 nm, 50 nm, 40 nm, 30 nm, 20 nm, 18 nm, 15 nm, 12 nm, or 10 nm. In embodiments, the cross-sectional area of the minimum opening of the channel (i.e. maximum constriction) is at least 1 $nm^2$, 2.5 $nm^2$, 5 $nm^2$, 7.5 $nm^2$, 10 $nm^2$, 12.5 $nm^2$, 15 $nm^2$, 17.5 $nm^2$, 20 $nm^2$, 25 $nm^2$, 30 $nm^2$, 35 $nm^2$, 40 $nm^2$, 45 $nm^2$, or 50 $nm^2$ or more. The cross-sectional area of the maximum opening of the channel (minimum constriction) is about 10,000 $nm^2$, 5,000 $nm^2$, 1,500 $nm^2$, 1,000 $nm^2$, 750 $nm^2$, 500 $nm^2$, 250 $nm^2$, 100 $nm^2$, 50 $nm^2$, 30 $nm^2$, 20 $nm^2$ or 15 $nm^2$, 10 $nm^2$, 7 nm2, or less.

In embodiments of this and other aspects, DNA nanopores include several DNA modules, e.g., helical bundles. In some embodiments, the nanopore includes between about 3 and 20 bundles of DNA, while in others about 3 and 16 bundles. In some embodiments, the DNA nanopores include between about 4 and 16 helical bundles, and in some embodiments, between about 6 and 16 bundles, or about 6 and 12 bundles of DNA.

In some embodiments of this and other aspects, DNA nanopores include one or more hydrophobic moieties on an outer surface of the DNA nanopore. To accomplish this, one or more nucleic acids that form a DNA nanopore can be modified to attach to, bind to, join, or link to one or more hydrophobic moieties, where hydrophobic moieties refer to a hydrophobic organic molecule. The hydrophobic moiety may be any moiety comprising non-polar or low polarity aliphatic, aliphatic-aromatic or aromatic chains and are capable of forming non-covalent attractive interactions with membranes, e.g., phospholipid bilayers and (co)polymer analogs thereof as defined elsewhere herein, and act as membrane anchors for the nanopore. Hydrophobic moieties of the disclosure encompass, e.g., long chain carbocyclic molecules, polymers, block co-polymers, and lipid molecules possessing membrane anchoring properties including sterols (including cholesterol, derivatives of cholesterol, phytosterol, ergosterol and bile acid), alkylated phenols, flavones and flavone-containing compounds, saturated and unsaturated fatty acids, and synthetic lipid molecules. The anchors for the polymer membrane may be the same as for lipid bilayers or they may be different. The specific hydrophobic moiety anchor may be selected based on the binding performance of the membrane chosen. In some embodiments, the hydrophobic moieties include one or more of ethyl phosphonothioate, cholesterol, porphyrin, or combinations thereof.

DNA nanopores of the disclosure can comprise two or more hydrophobic moieties that act to attach or connect or anchor the hydrophilic DNA nanopore to the generally hydrophobic membrane (e.g., lipid bilayer or polymer). Suitably attachment includes DNA oligonucleotides that carry the lipid anchor at the 5' or 3' terminus. Polynucleotides or oligonucleotides may be functionalized using a modified phosphoramidite in the strand synthesis reaction, which is easily compatible for the addition of reactive groups, such as cholesterol and lipids, or attachment groups including thiol and biotin. Enzymic modification using a terminal transferase can also be used to incorporate an oligonucleotide that incorporates a modification such as a hydrophobic moiety, to the 3' of a single stranded nucleic acid (e.g. ssDNA). Such hydrophobic moiety-modified anchor strands may hybridize via adaptor oligonucleotides to corresponding sections of the DNA sequence forming the scaffold section of the pore. Alternatively, the hydrophobic moieties can be assembled with the pore using lipid-modified oligonucleotides that contribute as either the scaffold or staple strands. A combination of approaches to incorporating hydrophobic moieties may also be used wherein hydrophobic moieties are incorporated into one or all of a scaffold strand, a staple strand and an adaptor oligonucleotide.

In some embodiments, the hydrophobic moieties are positioned around the periphery of the nanopore (i.e. away from the channel) such that they may extend radially outwardly from the nanopore structure and interact with the amphipathic membrane that surrounds and encloses the nanopore. In some embodiments, the hydrophobic moieties are positioned on a membrane-facing surface of the DNA nanopore such that they may extend radially outwardly from the nanopore structure and interact with the amphipathic membrane that surrounds and encloses the nanopore. In embodiments, the plurality of hydrophobic moieties can be positioned substantially equidistantly about the periphery of the nanopore such that insertional forces may be distributed more evenly about the outer periphery of the nanopore. By way of example, where two membrane anchors are used they will be spaced about 180° from each other; where three membrane anchors are used spacing between each is about 120°; for four membrane anchors spacing is around 90°; for five membrane anchors spacing is around 72°; for six membrane anchors spacing is around 60°; and for seven spacing is around 52°. Spacing diminishes proportionately for a greater number of hydrophobic moieties.

Alternatively, the hydrophobic moiety can include one or more modifications within synthetic nucleic acids (XNAs) incorporated into the DNA nanopore. For example, one or more of the DNA origami scaffold and/or staple strand may be fully or partially comprised of a synthetic nucleic acid analogues with hydrophobic character that enables the nanopore to interact and embed within a membrane. In such an embodiment the presence or one or more additional hydrophobic moieties bound to the nanopore may not be necessary, with the requisite level of hydrophobic membrane anchoring capability comprised within the backbone of the nanostructure itself. In some embodiments, DNA nanopores include a combination of hydrophobic moieties attached to the surface of the DNA nanopore and synthetic nucleic acids.

The membrane in which the DNA nanopore is inserted or enclosed may be of any suitable type. In some embodiments, the membrane can be a lipid bilayer or a polymer sheet or film. The membrane can be an amphiphilic layer, which is a layer formed from amphiphilic molecules which have both hydrophilic and lipophilic properties. The amphiphilic layer may be a monolayer or a bilayer of synthetic or naturally occurring molecules. The lipophilic properties of the molecules comprising the membrane promote anchoring by hydrophobic moiety-based anchors or other hydrophobic anchoring regions within the nanopore structure as described above.

In some embodiments, the amphiphilic layer may be a lipid bilayer. The lipid composition may comprise naturally occurring lipids such as phospholipids and bipolar tetraether lipids, and/or artificial lipids. The lipids typically comprise a head group, an interfacial moiety and two hydrophobic tail groups which may be the same or different. Suitable head groups include, but are not limited to, neutral head groups, zwitterionic head groups, negatively charged head groups and positively charged headgroups. The head group or the tail group of the lipids may be chemically modified.

In embodiments of this and other aspects, a nanopore that weakly binds or weakly interacts with a target includes a $K_D$ value of less than about 100 nM, less than about 1 μM, less than about 10 μM, less than about 100 μM, less than about 1 mM, or less than about 10 mM, or less than about 100 mM, or between about 100 mM and 100 nM, or between about 10 mM and 10 μM, or between about 1 mM and 10 μM, or between about 10 mM and 1 μM, or between about 100 μM and 100 nM, or between about 100 μM and 1 mM.

In another aspect, a method for identifying one or more target signature of and quantifying the abundance of one or more targets in a sample is provided, including (i) introducing a sample into the space superior to the membrane of two or more DNA nanopores immobilized to the planar array of protodes in devices according to the other device aspects and embodiments described herein, (ii) applying an electric field across the membrane(s); (iii) monitoring changes in signal magnitude, signal duration and frequency of signal change across the membrane to determine one or more target signatures; and (iv) determining a presence and abundance of a target in the sample as a function of the one or more target signatures. In some embodiments, the method can identify and quantify of one or more targets occurs in real time.

The devices and methods described herein are intended to be used to detect one or more targets in any kind of suitable sample. In some embodiments, the sample may be obtained from a biological sample such as cells, tissues, bodily fluids, and stool. Samples that are not in liquid form are typically converted to liquid form before analyzing the sample with the methods described herein, e.g., tissue samples and certain bodily fluids, e.g., cerumen. However, in some embodiments, a sample is not processed prior to testing. Bodily fluids include but are not limited to, amniotic fluid, aqueous humour, vitreous humour, blood (e.g., whole blood, fractionated blood, plasma, serum, etc.), breast milk, cerebrospinal fluid (CSF), cerumen (earwax), chyle, chime, endolymph, perilymph, feces, gastric acid, gastric juice, interstitial fluid, lymph, mucus (including nasal drainage and phlegm), pericardial fluid, peritoneal fluid, pleural fluid, pus, rheum, saliva, sebum (skin oil), semen, sputum, sweat, synovial fluid, tears, tissue exudates, vomit, urine and exhaled condensate. In some embodiments the sample includes whole blood, serum, saliva, urine, sweat, interstitial fluid, spinal fluid, cerebral fluid, tissue exudates, macerated tissue samples, cell solutions, intracellular compartments.

In other embodiments, the sample may be obtained from an environmental sample, including, but not limited to liquid samples from a river, lake, pond, ocean, glacier, iceberg, rain, snow, sewage, reservoir, tap water, drinking water, and the like; solid samples from, e.g., soil, compost, sand, rocks, concrete, wood, brick, sewage, and the like. Typically, samples that are not in liquid form are converted to liquid form before analyzing the sample. However, in some embodiments, a sample is not processed prior to testing. In yet other embodiments, the sample may be obtained from a food sample that is suitable for human or non-human animal consumption. A foodstuff sample may if include, but not limited to, raw ingredients, cooked food, part and animal sources of food, preprocessed food as well as partially of fully processed food, etc. Typically, samples that are not in liquid form are converted to guide for in before analyzing the sample with the present method.

In another aspect, a method for fabricating a stochastic sensing device for sensing one or more targets in a sample, including (i) depositing a bioprotonic conducting material onto a non-conducting material arranged to form one or more protode contact areas; (ii) electrically isolating each protode contact area; (iii) introducing DNA origami to the protode contact areas for self-assembly onto the bioprotonic conducting material, in which the DNA origami comprises one or more anchoring linkers; (iv) introducing DNA nanopores to the protode contact areas, where the DNA nanopores comprise one or more nanopore anchoring linkers complementary to the anchoring linkers on the DNA origami, one or more hydrophobic moieties on an outer surface of the DNA nanopores, and one or more target binding moieties opposite the nanopore anchoring linkers; where the nanopore anchoring linkers bind to the anchoring linkers on the DNA origami thereby immobilizing the nanopores on the DNA origami; and where the target binding moieties interact weakly with one or more determinants on the target; and (v) forming a membrane within the electrically isolated protode contact area and surrounding the DNA nanopore, defining a space inferior to the membrane and a space superior to the membrane, such that one ionic pathway exists between the bioprotonic conducting material and the space superior to the membrane, through the nanopore; where each protode contact area contains on average one immobilized DNA nanopore; and where the stochastic sensing device can identify one or more target signatures and target quantity in real time.

In some embodiments of the method for fabricating a stochastic sensing device, the bioprotonic conducting material is deposited on the non-conducting material, e.g., $SiO_2$, using electron beam lithography (EBL), or other suitable method, such that protode ('electrode') contacts are created and connected to active regions of interest. Such deposition can be affected in an irregular or random manner but is preferably arranged in a patterned array. In some embodiments, each protode contact area is electrically isolated by a method including nano-sphere lithography (NSL), reactive ion etching (RIE), passivation and bead removal; or a photoresist process, or other suitable method. For example, appropriately sized polystyrene microspheres can be self-assembled into the conductive wells of the active regions of interest using NSL such that only a single microsphere is loaded into a single well. Subsequently, RIE of the nanospheres can be conducted to reduce the diameter of the spheres to the desired nano-dimensions, e.g., large enough to contain a DNA nanopore. Exposed regions without a bead present can be passivated to render them hydrophobic and minimize interactions with biomolecules. The beads are removed using physical methods (e.g., sonication, tape stripping, and the like) or washing with organic solvents (e.g., absolute ethanol, chloroform, toluene, and the like), to expose an activated surface of the bioprotonic conducting material in each well. Further steps to complete an exemplary device include using templated polydimethylsiloxane (PDMS) techniques to create a microfluidic device constructed such that the active wells are inside fluid flow channels, and their corresponding electrodes are exposed for electronic connections. A solution of DNA origamis that include one or more anchoring linkers can be introduced into the microfluidic device, which precisely self-organize on the active spots of the patterned surface. Uniquely modified DNA nanopores with (1) one or more nanopore anchoring linkers complementary to the anchoring linkers on the DNA origami and (2) hydrophobic moieties on the outer surface are introduced and immobilized to the DNA origami via complementary overhang hybridization of respective linkers. An insulating membrane, such as lipid bilayer (LBL) or block co-polymer layer, is created on the surface through sequential microfluidic flow of a lipids or block co-polymers over the microwells to ensure that the DNA pores are membrane spanning such that the only ionic pathway between the surface of the bioprotonic conducting material and the bulk solution is through the nanopores. An array of active surfaces each of which accommodates only one DNA origami is preferably obtained.

Yields of such assemblies can be optimized by reducing non-specific interactions of the nanopores with the background, which can be achieved through, e.g., surface passivation to minimize non-specific interactions using polymers like, e.g., PEG or other zwitterionic polymers, and/or surfactants like, e.g., Tween 20, Tween 80, or sodium dodecyl sulfate (SDS) in the buffer during assembly.

In some embodiments of the devices described herein, the array of low affinity nanopore sensors are constructed as a lab-on-chip microfluidic assembly compatible with biotic interfaces and capable of dynamic quantification over a relevant period of measurement, e.g., seconds, minutes or tens of minutes time scales preferably, even for a limited quantity of sample. Such embodiments can stochastically sense targets at single molecule sensitivity, in a complex biofluid. In some embodiments the sample does not require pre-processing.

The effects of size, complexity, and different modifications of the nanopore on the patterned array formation can be explored and systematically characterized using Atomic Force Microscopy (AFM), fluorescent microscopy and electrical impedance spectroscopy. Sensing can be optimized by decorating the nanopore with affinity binders whose interaction to molecules in solution can be engineered to differentially vary across the array. To achieve this, each nanopore can be prepared with a specific conjugated peptide or nucleic acid aptamer using, e.g., overhang hybridization or click chemistries as described elsewhere herein. The lip of nanopore is designed to be decorated with unique peptides or aptamers such that any reversible binding event at this region leads to a marked reduction in the nominal cross-section of the conductive pathway, which, in turn, reduces the protonic current through the pore. It is not necessary to track which nanopore is tagged with which binding moiety since the single molecule binding events can be post-processed to uncover this information. This makes the fabrication of the entire nanopore population a single one pot reaction. Software such as caDNAno, CanDo, oxDNA, NUPACK, and the like, can be utilized to design, simulate, and analyze of the nanopore structure and interactions.

Sensor Array Arrangement

Current methods for spatially separating sensors on a surface can be classified into three categories. A first category relates to surface chemistry modifications, such as charge based adsorption of antibodies paired with localized wide field techniques such as photoactivation localization microscopy (PALM), direct stochastic optical reconstruction microscopy (dSTORM). A second category relates to physical separation either through self-assembly methods, such as water in oil droplets, or on a pre-patterned surface such as microwells for capturing beads in the case of digital ELISA. A third category relates to direct sensor synthesis at known locations via selective spatial activation.

Surface chemistry modifications offers minimal control and produces a non-uniform distribution of sensors on a planar surface where single molecule signal differentiability is lost when high concentrations of sensing elements are loaded. In addition, multiplexing involves either loading different sensing elements on different spatial locations or using multiple channels for simultaneous detection, hampering scalability due, e.g., to space and cost.

Physical separation offers more control and can produce a more uniform spatial distribution of sensors. This technique offers an advantage of eliminating the need for specific sensor arrangement and allows dense packing of sensors limited by the fabrication techniques. For example, in digital ELISA, microwell arrays are created from a master mold using lithography techniques followed by injection molding and integrated polymeric assemblies. There are disadvantage to standard physical separation techniques. For every new assay design or functional change, a new mold is required, which reduces the modularity of the process. Further, dense packing of sensors are limited to about 300 nm, much larger than the size of the sensing elements, which can be about 2 orders of magnitude smaller. Still further, an advantage of this technique when identifying a modest number of targets, i.e., retroactive label-based sensor recognition using multiple readout channels, limits scaling as the number of readout channels increases linearly with the number of targets to be identified (and therefore sensors) increases.

Direct sensor synthesis allows multiplexed sensor synthesis in fewer bulk chemical reactions, higher density of sensors, limited only by the diffraction wavelength of energy wave used for activation, and higher degree of miniaturization. However, this technique is limited by the availability of synthesis chemistry, creation of a mask and diffraction limits of mode of energy.

To address such challenges, in some embodiments devices of the disclosure include a sensor arrangement that allows sensor identity agnostic, label-independent and multiplexed quantification of targets. In some embodiments, the DNA nanosensors are arranged in a closely packed spatial sensor array where a variety of nanosensors (i.e., a plurality of sensors with distinct target binding moieties attached) are assembled randomly. In embodiments, each sensor is connected to and/or addressed by an individual detector or detector channel with single molecule resolution. Importantly, sensors of the disclosure do not require multiple channels for recognition of identities of the sensor elements. Instead, the sensor array can be calibrated after assembly in at least two ways, including (1) calibration of the randomly assembled array of sensors against known individual targets sequentially to identify individual sensors spatially; and (2) calibration of the randomly assembled array of sensors against unknown target mixtures to get baselines for analyses without the need for individual sensor identification.

Figure 3B:
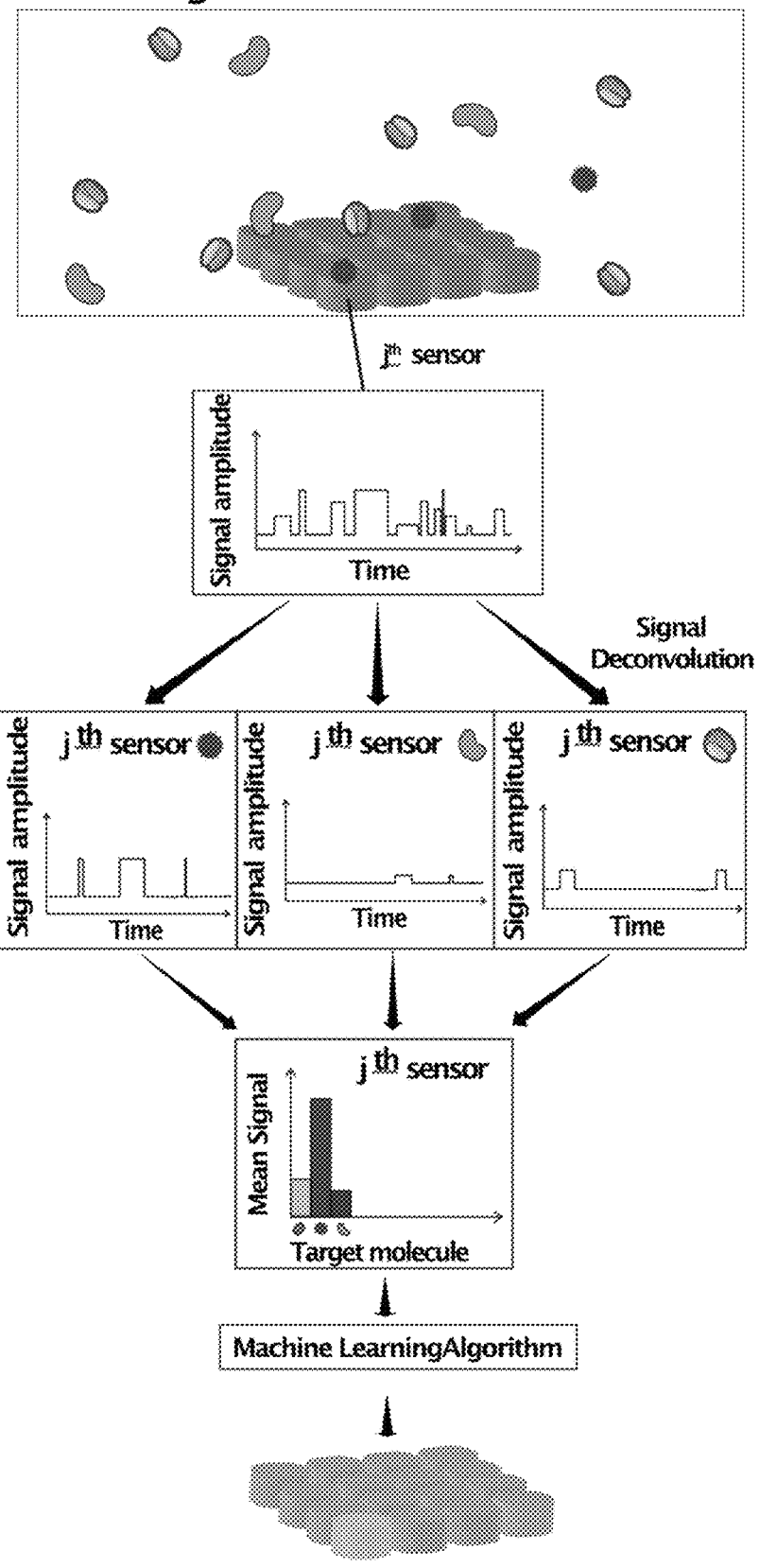

In the first calibration pathway, the planar array of randomly assembled sensors is exposed to each known target sequentially using, e.g., microfluidics. Electrical signals recorded for individual sensors as they interact with the known individual targets are mapped to their distinct spatial locations. The entire set of signals produced from exposure to the set of targets is then input into a machine learning algorithm which identifies the sensor at each spatial location by classifying them in a high dimensional space (FIG. 3).

In the second calibration pathway, individual sensor identities are not decoded. Instead, their response to a rich mixture of targets is set as a baseline. Electrical signals from sensors at each distinct location are de-mixed based on the signal amplitude and labeled for target association. For each target, the signal amplitudes from the entire array of sensors are set as a master baseline for target association (FIG. 3). If a subset of the targets with new mixture composition is introduced, the signal amplitudes from the array for each target should remain unchanged. If a different array with new randomization of sensors is used against the same subset of targets, the sensor-target associations will change; however, an algorithm can be used to identify the target associations based on the master baseline calibrations of the entire subset of targets. For in-vivo applications, the signature amplitudes of biomolecules from a population of healthy individuals can be set as a baseline.

Sensor-Target Relationship

For an array of stochastic single molecule sensors that are cross-reactive with a variety of targets, two theoretical scenarios were considered. In the first scenario five unique but randomized stochastic single molecule sensing elements interacting with a mixture containing 20 unique targets, which scenario addressed whether a variety of targets spread over a large dynamic range were distinguishable using a small set of unique sensing elements, especially in presence of measurement noise. The minimum number of unique sensing elements required to distinguish between a set of targets was evaluated. In the second scenario, 80 unique but randomized stochastic single molecule sensing elements interacted with a mixture containing 20 unique targets, which scenario addressed whether increasing the dimensionality of the system is favorable for distinguishing the identity of the targets, and if so, to what extent is it beneficial.

In each of these scenarios, unique interactions were assumed between each target molecule and the sensor by the virtue of careful design of the sensing element. These unique interactions were characterized by the $k_D$ values for each pair, uniquely drawn from a normal distribution. To represent weak binding design, the $k_D$ values were normally distributed between the range of 1 mM to 0.1 uM, characterizing a dynamic range of 4 orders of magnitude. These were hereby referred as true $k_D$ values. Since $k_D$ values for each pair were obtained from temporal measurements of on and off events, the consequence of missed events due to lack of resolution or error in readings due to presence of measurement noise was considered. To emulate the errors, a randomly drawn Gaussian noise (up to 30% of the true $k_D$ values) was added to the readings. The resulting readings were hereby referred as the measured $k_D$ values. 1000 instances of such measurements were repeated for the set of targets for both scenarios, and the results were fed to a machine learning algorithm to infer the effects of varying number of sensors on distinguishability of the targets.

Figure 4A:
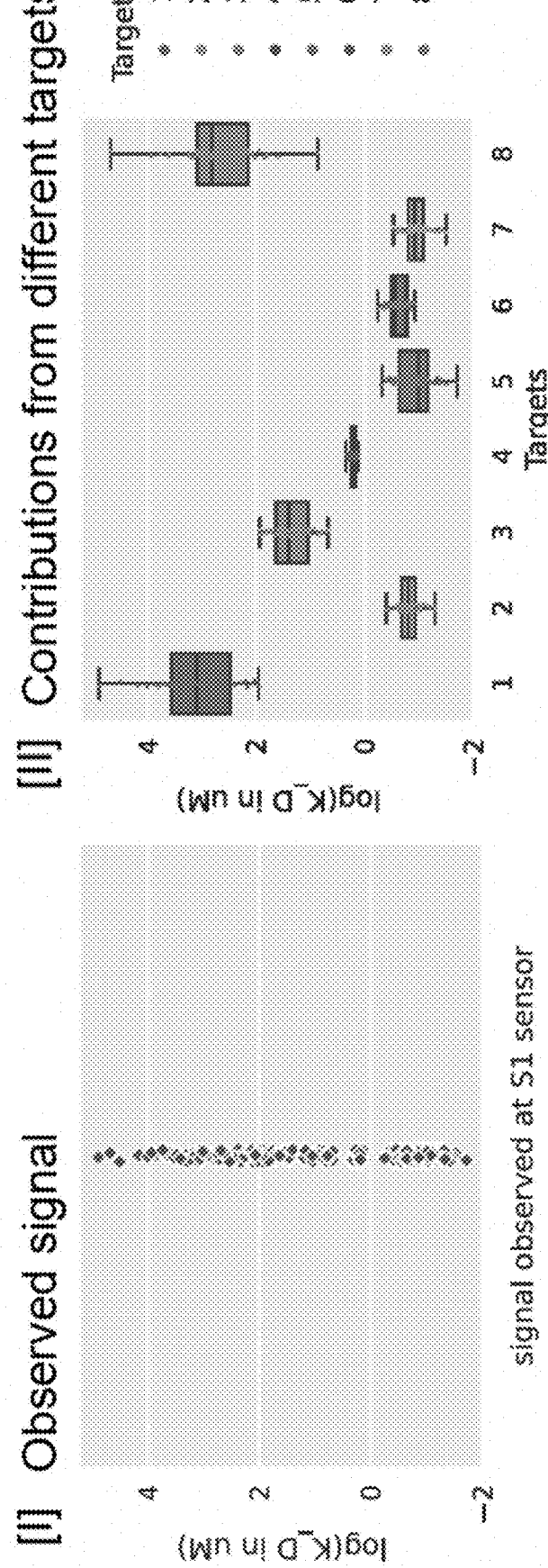
FIG. 4A to FIG. 4C show the effect of increasing dimensionality of the sensor space on accurate classification of signals from multiple targets.
Figure 4B:
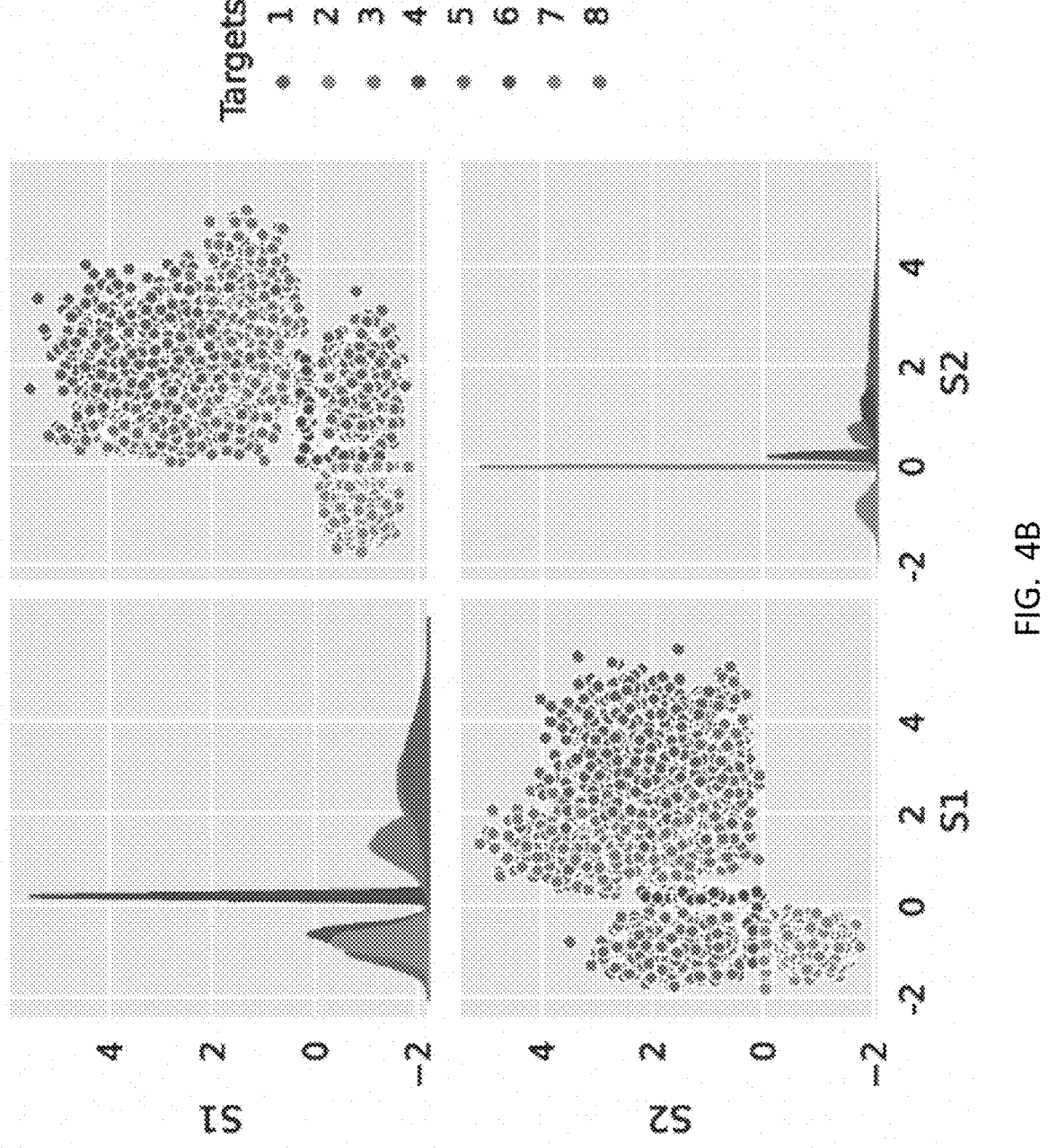
Figure 4C:
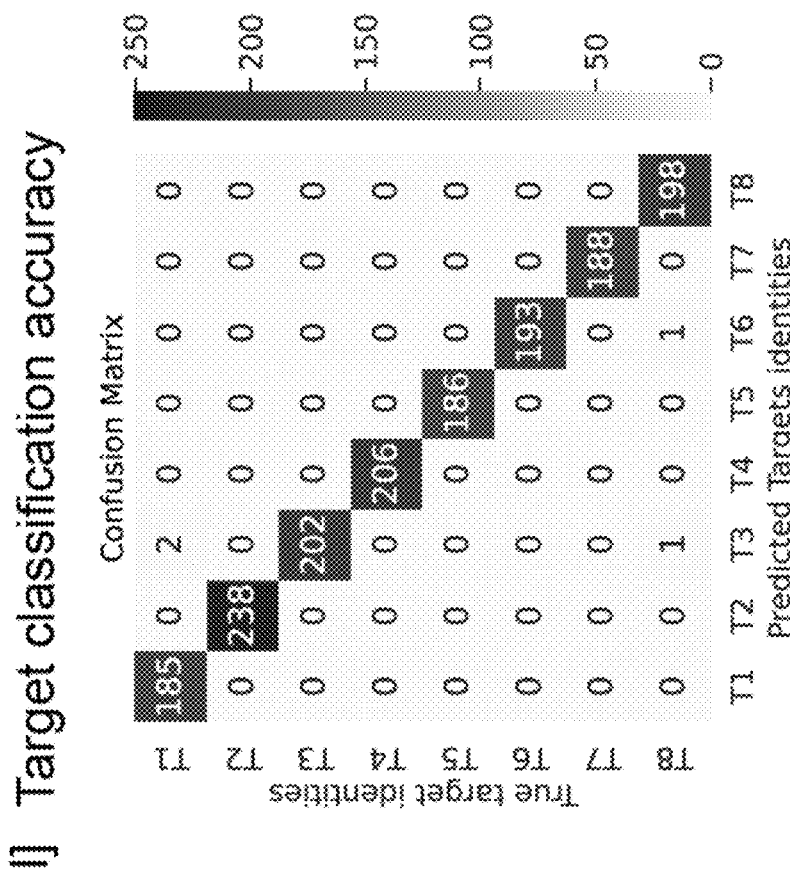
Figure 5A:
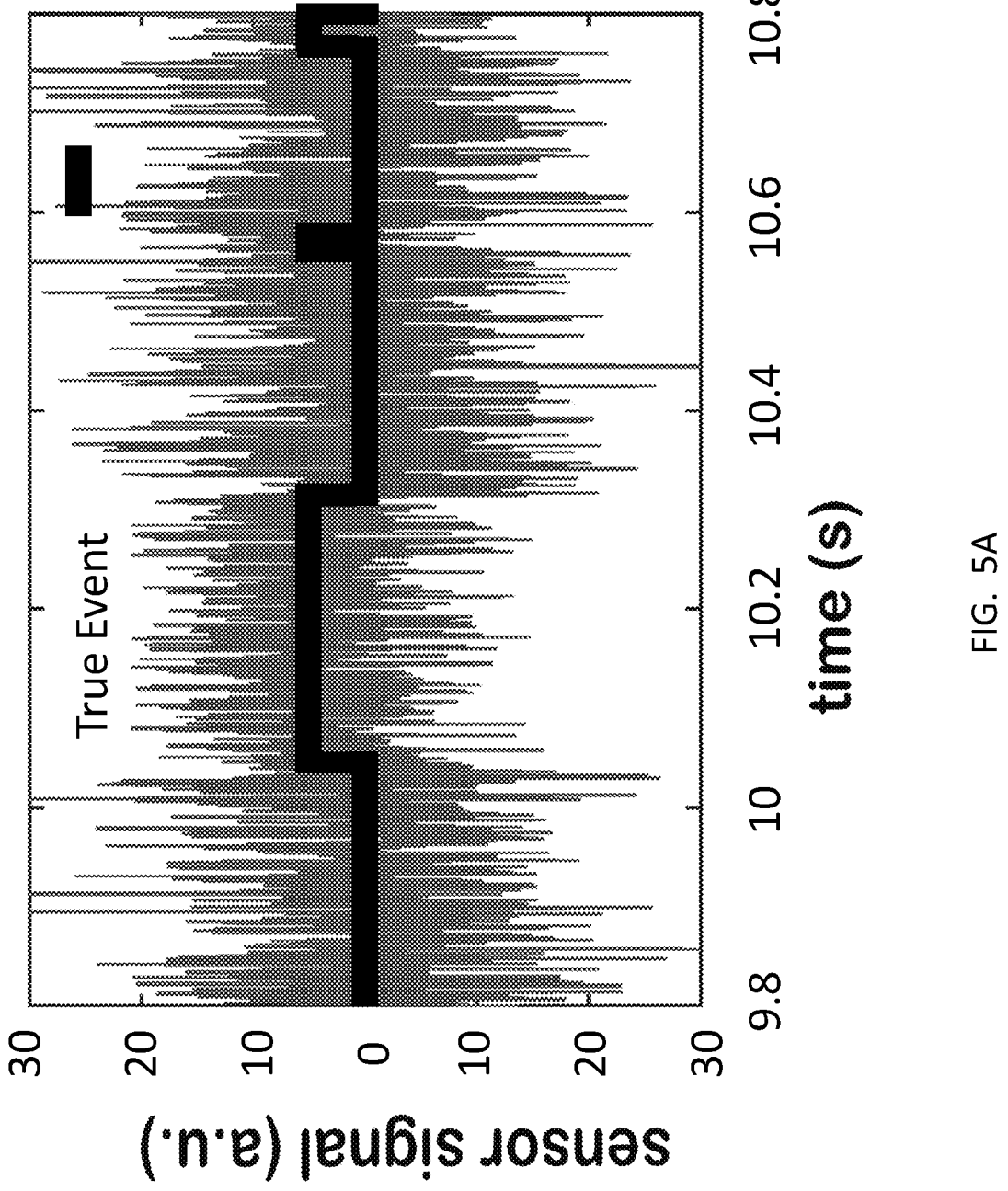
FIG. 5A to FIG. 5C show dynamic analysis of a simulated single stochastic sensor records to obtain $k_{off}$ and $k_{on}$ values.
Figure 5B:
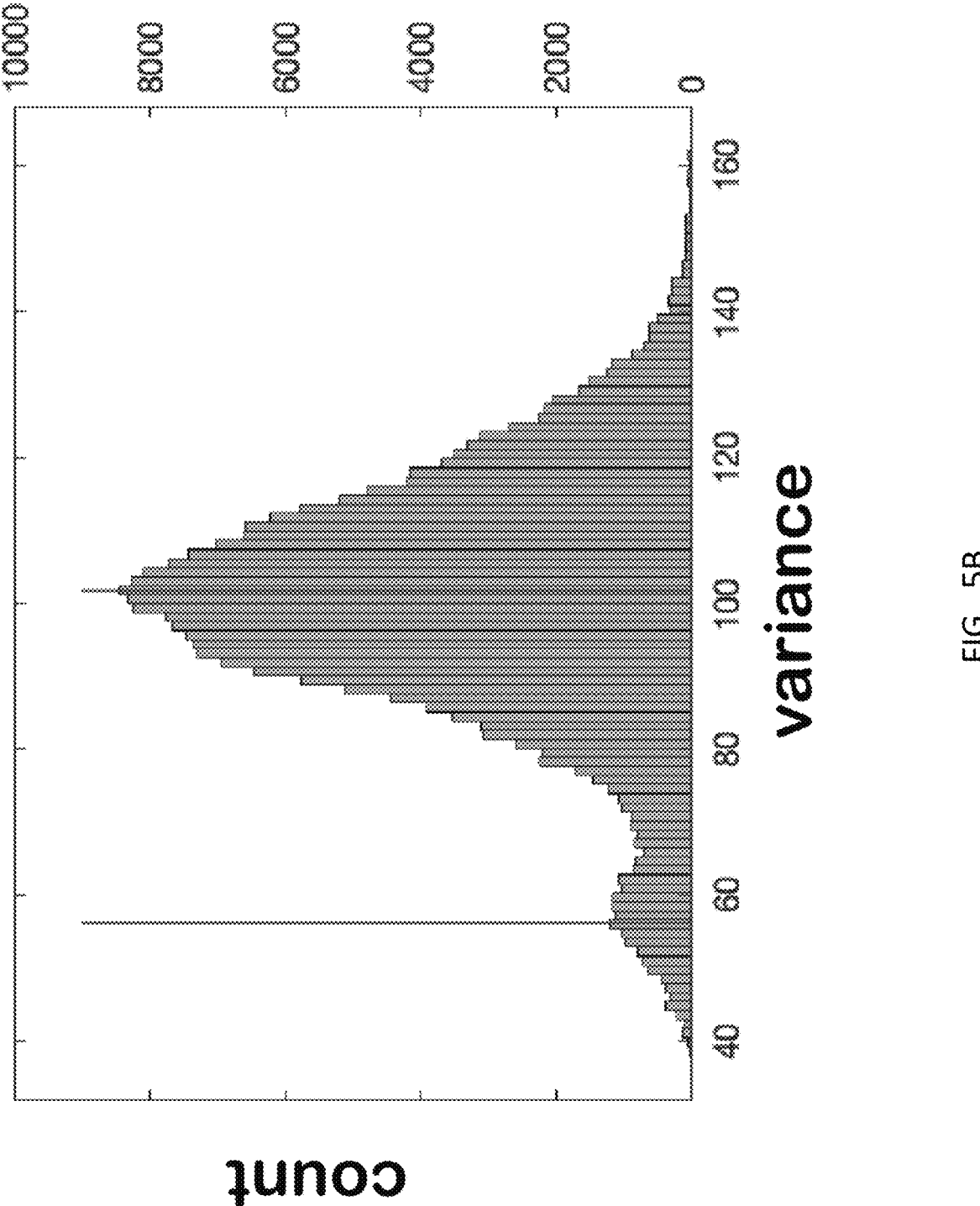
Figure 5C:
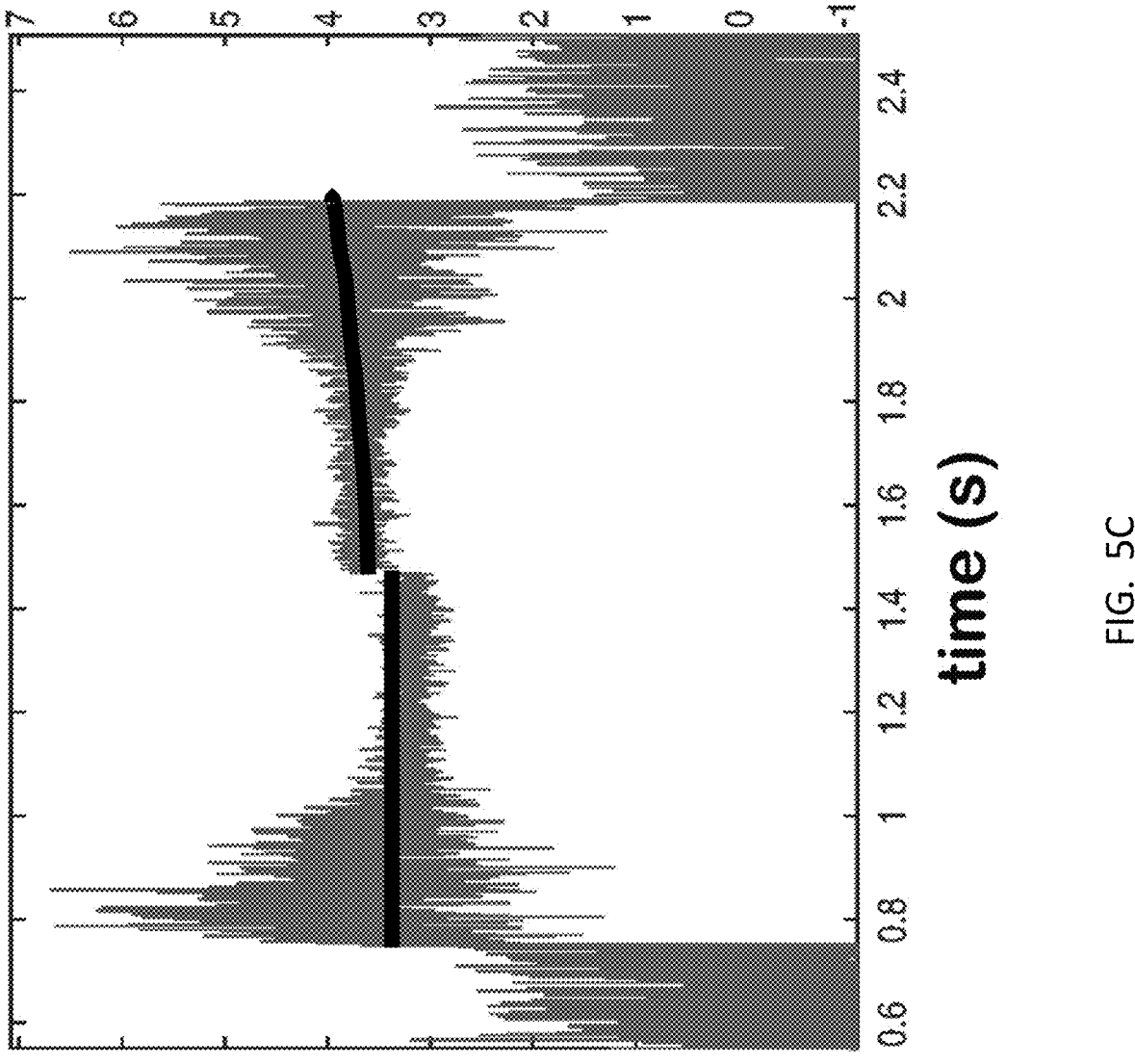

FIG. 4A illustrates a typical matrix of true and measured $k_D$ values as well as the noise in the measurement. Each sensor added a new dimension to the data. This is illustrated in FIG. 4B where, in two dimensions along sensors S1 and S2, data from each target is intermixed. For example, data from target 3 is indistinguishable from data from target 8. However, when an additional sensor S3 was added, data from targets 3 and 8 became spatially distinct along the axes of S2 and S3 sensors. Similarly, after adding a new dimension of sensor S3, data from target 1 was clearly spatially separated from 8 in the 3-dimensional space. Therefore, increasing dimensionality helped to delineate the spread of data owing to the increase of hyperspace in which the data exists. However, a consequence of the increase of hyperspace is also the sparsity of data. Unless the number of measurements scale up exponentially for each added dimension, the data becomes sparse.

The minimum number of sensors for distinct data pools for each unique target in the hyperspace is dictated by the minimum number of dimensions needed to avoid overlap between hyperspheres that encompass data spread of each target.

The array of weak binding sensing elements enable multiplexed protein identification and readout while removing the burden of designing specific sensors for each protein, which may significantly expand the clinical base of proteome assays and protein-based drug targets up from about 1% today. Integration with machine learning techniques allows intelligent optimization of design of the sensors, as well as shifts the burden of protein identification from sensor design to signal readout.

Temporal Bounds of the Array

The design of sensors on the array of the disclosure influences the measurable dynamic range as well as the resolution of the device. Since $k_{off}$ is directly attained from the mean on time $T_{on}$, the desired frame rate should be much faster than rate of dissociation, i.e., the temporal resolution should be much smaller than the smallest observed $T_{on}$. However, the total observation window required to capture all the target interactions is dictated by both binding and unbinding events, and the window should be long enough to capture multiple binding and unbinding events. So, the observation window should be much larger than both maximum $T_{on}$ and maximum $T_{off}$ in the entire sensor-target set. Therefore, the measurement window is dependent on $k_{on}$, $k_{off}$ and [T] in the solution. For example, in a solution where we expect to find a sensor that captures a biomolecule with $k_{off}$ on the order of $10^{-3}M^{-1}$ and with $k_{on}$ of $10^6M^{-1}$ $s^{-1}$, temporal resolution must be much less than 1000 s. To be able to detect a concentration of molecules over the range of 1 mM to 1 nM, the observation window must be at least $1/k_{on}[T]$ long to see binding an unbinding event with high on probability, i.e., at least 17 minutes long. The ability to engineer sensing elements and tweak the binding constants of interactions based on a set of expected targets is immensely powerful in dictating the temporal resolution, experimental window, observable dynamic range and, also, the minimum limits of detection.

In biological fluids, the concentration of proteins and small molecules varies over a large range of about 1 μM to 1 fM. It is desirable for $k_{off}$ values to be on the order of 1 $s^{-1}$ to allow a sufficient resolution in time, though $k_{off}$ values are not limited thereto. In the case of a $k_{off}$ value of about 1 $s^{-1}$ and biologically relevant protein and small molecule concentrations in biological fluids of about 1 μM to 1 fM, the $k_{on}$ values may be between about $10^6$ $M^{-1}$ $s^{-1}$ and $10^{11}$ $M^{-1}$ $s^{-1}$ to keep the experiment window in the order of tens of seconds, i.e., the $k_D$ values should range between $10^{-6}$ M to $10^{-15}$ M. Notably, while such $k_D$ values are typically considered high affinity $k_D$ values, high affinity "tight binding" complexes usually have very small $k_{off}$ values (and thus long mean binding complex lifespans; e.g., biotin-streptavidin with a lifetime of about 10 days) to yield these $k_D$ values. $k_D$ values can also reflect "weaker" binding in the presence of a large $k_{off}$ as contemplated herein. Detectors capable of high temporal resolution can detect binding events with larger $k_{off}$ values (i.e., lower mean lifetime of the binding complex), correspondingly lowering the $k_D$ value. Thus, the sensors of the disclosure have weak interactions with the targets and the detection system is capable of high temporal resolution.

For a planar array, the diffusion times of the biomolecules in the bulk of the solution to the plane of sensors are dependent on their size. This fact can be advantageous for correlating the migration time with the target size depending on when the signature of a particular target is first observed. The temporal data this provides additional information that is useful for target identification and analysis similar to that used in DNA fragment separation.

Multiplexed Data Acquisition

Multiplexed data acquisition from a cross-reactive array of stochastic sensors generates a high density of multivariate signals. The most fundamental and crucial issue in the design of signal transduction mechanism for such a configuration is establishing discrete interfaces between the single molecule sensor where biotic events occur and the abiotic system that generates corresponding detectable signals. Mechanisms that have been explored for signal generation include optical, mechanical, electrical, electrochemical, and calorimetric methods. For example, in ELISA fluorophores are employed to generate signal upon binding and the signal is captured by a charge-coupled device (CCD) detector. However, in multiplexing, a pertinent issue for integration of the generated signal with detection is addressability of the signal from many different sensors, especially when the separation between two sensors is smaller than the resolution limits of the detection system.

Sensors of the disclosure are cross-reactive biological elements or synthetic elements that are patterned or directly coupled to individual detectors such that the stochastic signals are measurable and addressable. Aptamer recognition-based sensors are suitable elements for patterning cross-reactive planar arrays as they form biological interfaces that can overcome issues such as biofouling and aggregation.

However, in biology the primary exchange of information occurs through ions such as protons, sodium, potassium, or other small molecules. Capturing ionic information from non-conductive elements to electrons in conductive substrates for direct readout is typically burdened with a low efficiency of signal conversion. However, synthetic elements, such as polymers, inorganic and organic semi-conductors that undergo redox reactions can be used as cross-reactive sensing elements such that, in a multi-electrode array, each electrode acts as an active sensor and is directly coupled to an electronic detector system.

A complication of integration of abiotic elements in-vivo leads to non-specific adsorption of biological entities such as proteins, lipids, and polysaccharides on the sensor surface and impedes the coupling between the electrode and the redox elements. Chemical modification of the electrode surfaces with layers of, e.g., oligoethylene glycol (OEG) or polyethylene glycol (PEG) can be employed to increase hydrophobicity and minimize biofouling. However, such coatings can partially shield the sensor and minimize interaction forces between the sensor and targets, which leads to reduction in signal conversion efficiency.

Dynamic Readout

Electromoriogram devices of the disclosure produce a dynamic electric signal relating to the real time changes in the molecular interactions of the sensors. The data transduced from each sensor is analyzed individually, as well as in relation to other sensors, for accurate classification and quantification. Choosing a sliding observation window that is larger than the timescale of binding and unbinding events enables analysis of the dynamic signal. To uncover the binding interaction for each target, multiple events from a single stochastic sensor within the sliding window can be synchronized after recording and analyzed using techniques such as ensemble averaging. For multi-target analysis, simultaneously decoding $k_D$ values for all individual target-sensors interactions is possible where the sliding observation window applied to the array of sensors is optimized for the entire set of targets. By combining the individual sensor predictions with a machine learning method, such as the one demonstrated earlier, along with concentration calibration experiments can uncover the identities and quantify all the targets within a complex mixture dynamically. As the concentrations change, the captured readouts change and lead to the current composition. As multiple targets interact with a sensor, unique signal amplitudes, as well as multi-variate binding event distributions, are obtained, which can be deconvolved using algorithms and post-processed to reveal the target identities.

To electrically characterize the array, partially complementary DNA strands can be introduced into the solution. The time trace of protonic current depends, at least in part, on the degree of complementarity between the strand tethered to the nanopore and the strand in the solution as well as the concentration of the strand in the solution. A grid of several sensors with varying degrees of interactions can be obtained by designing nucleic acid aptamers of different lengths and binding abilities such that they have varying degrees of weak and reversible interactions with the solution strands of interest. By observing the map of ionic current in different areas of the grid, a unique molecular signature can be obtained for each strand. Further, by observing the strength of signal within the same pattern, quantitative information about the concentration of the strand can be obtained. Taking advantage of the precise placement and programmability of DNA nanopores, larger nanopore electrodes can be designed such that they are separated widely and only one single nanopore is present per unit area of the bio-protonic membrane. This design allows for repeating of the above experiments to demonstrate single molecular binding events. Such characterization experiments also creating training datasets for a robust and accurate classification algorithm.

Figure 6A:
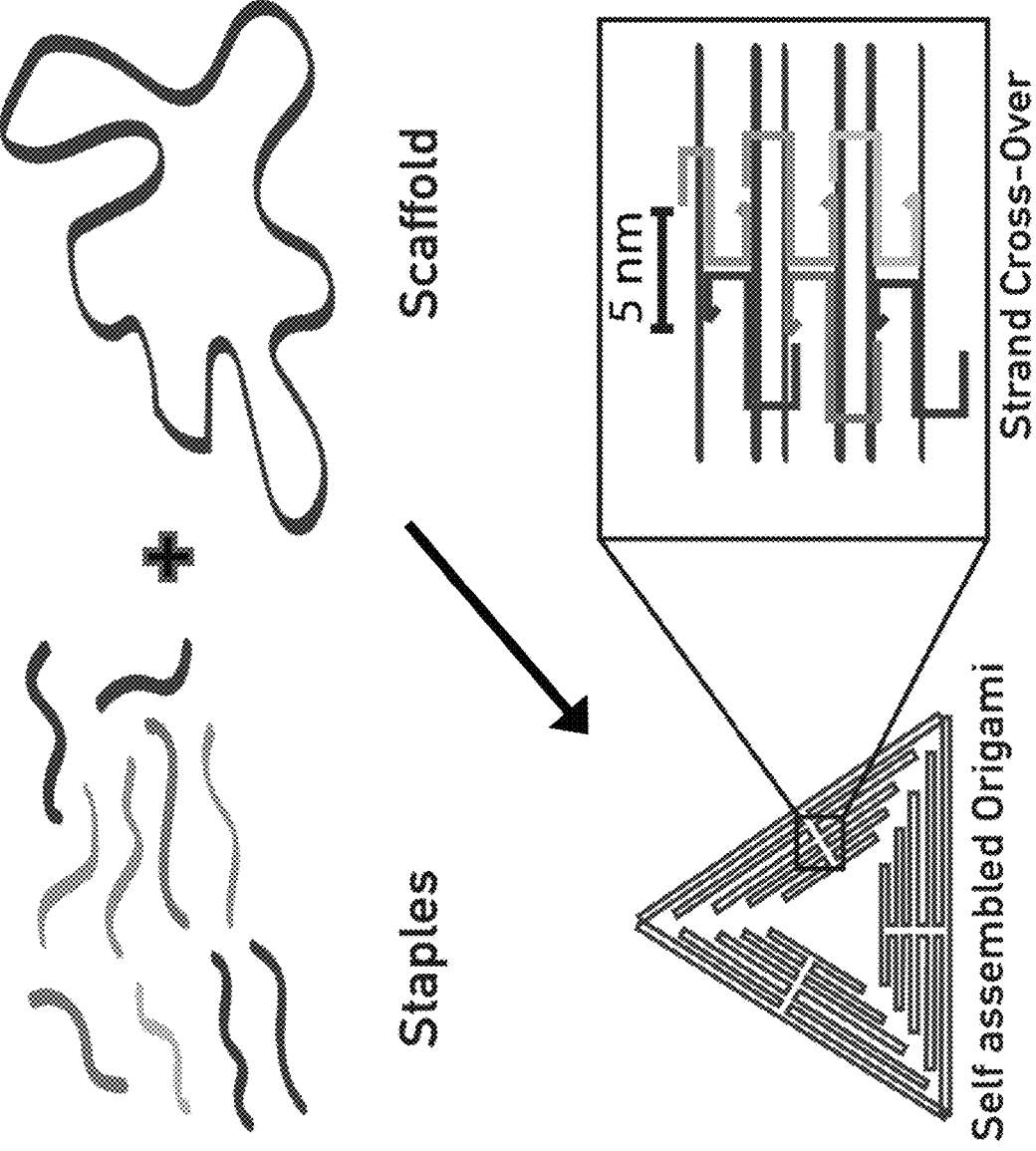
FIG. 6A to FIG. 6C illustrate a facile route to experimentally build an electromoriogram as described herein.
Figure 6B:
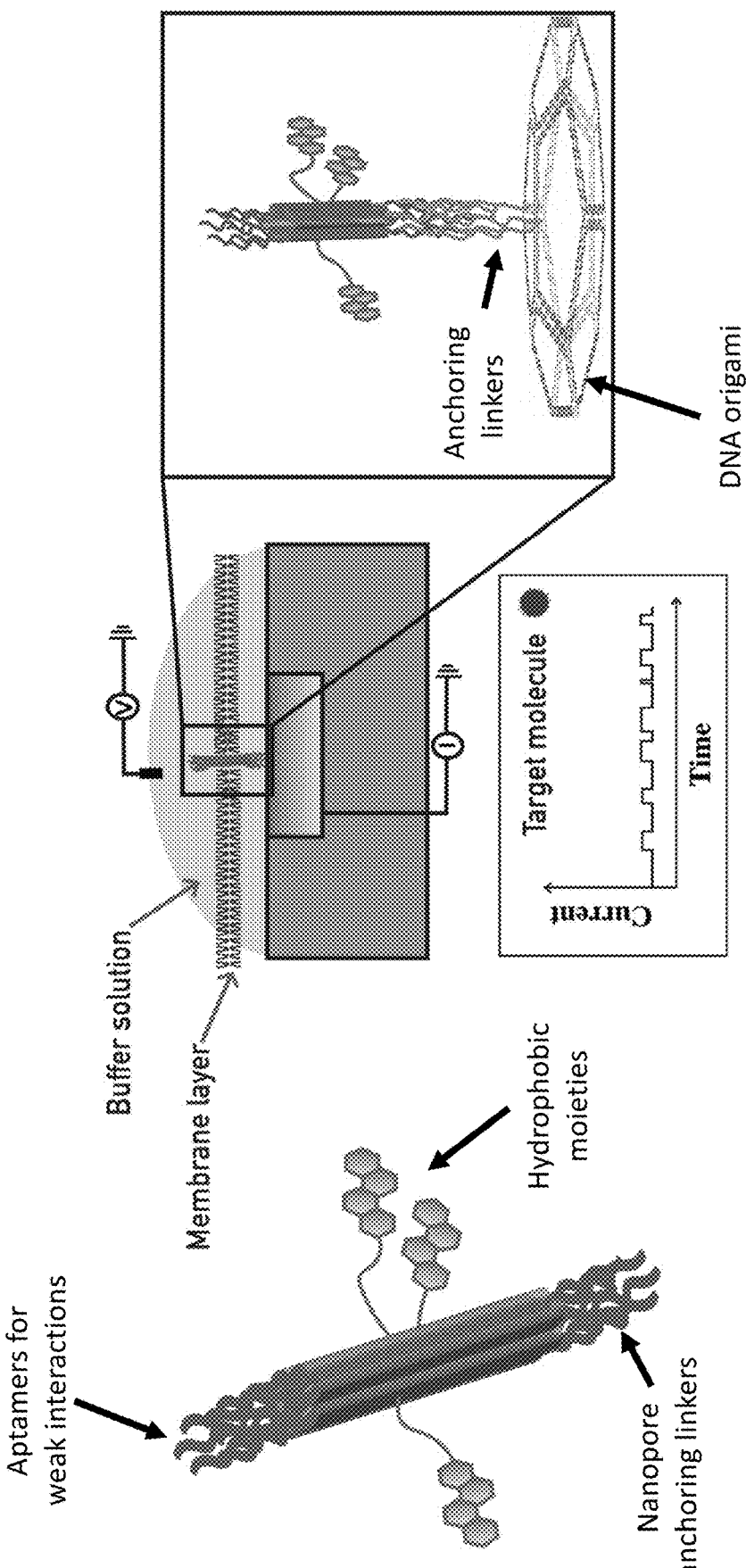
Figure 6C:
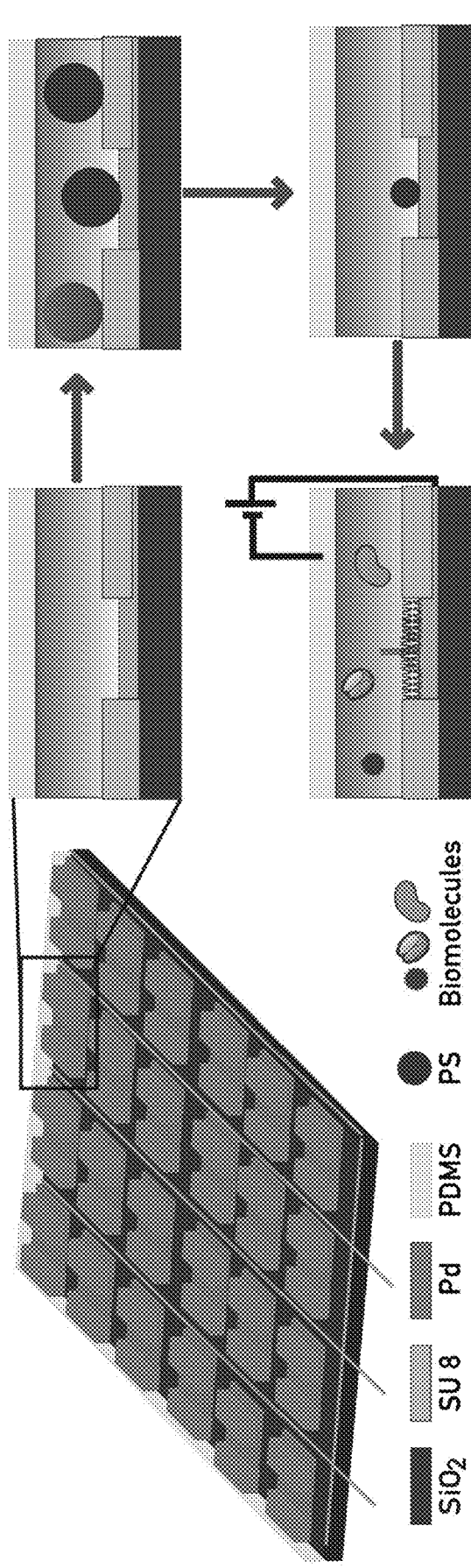

The current across the nanopores can be measured where the proton conductivity through each of the electrodes is measured to verify that the conduction path is defined by the nanopores (FIG. 6C). In this scenario the protonic current per unit area is expected to be directly proportional to the detailed structure of the nanopores, number of conduction pathways, and the interface with the lipid bilayer. Certain optimization parameters for measurement baselines include changes to the conductivity with nanopores of different dimensions, the effect of hydrophobic moieties for membrane insertion, and the length of the anchoring tether as well as use of different lipids or block copolymers themselves.

The sensors and quantification techniques described herein are unlike current state of the art diagnostic tests in that high affinity specific binders such as antibodies are not needed. Pattern recognition capability of this protein quantification array is based on differential binding events. Since ionic current signatures are characterized by differential interactions of targets with a receptor array, a large variety of non-specific unique peptides or orthogonal nucleic acid aptamers are sufficient to generate identification patterns for challenging matrices such as bio-fluids. With an increase in the dimensionality of the signal, the nanopore sensor array provides an enhanced resolution for the differentiation of targets compared with a single-pore configuration.

All statements herein reciting principles, aspects, and embodiments of the disclosure, as well as specific examples thereof, are intended to encompass both structural and functional equivalents thereof. Additionally, it is intended that such equivalents include both currently known equivalents as well as equivalents developed in the future, i.e., any elements developed that perform the same function, regardless of structure.

Various other components may be included and called upon for providing for aspects of the teachings herein. For example, additional materials, combinations of materials and/or omission of materials may be used to provide for added embodiments that are within the scope of the teachings herein. Adequacy of any particular element for practice of the teachings herein is to be judged from the perspective of a designer, manufacturer, seller, user, system operator or other similarly interested party, and such limitations are to be perceived according to the standards of the interested party.

In the disclosure hereof any element expressed as a means for performing a specified function is intended to encompass any way of performing that function including, for example, a) a combination of circuit elements and associated hardware which perform that function or b) software in any form, including, therefore, firmware, microcode or the like as set forth herein, combined with appropriate circuitry for executing that software to perform the function. Applicants thus regard any means which can provide those functionalities as equivalent to those shown herein. No functional language used in claims appended herein is to be construed as invoking 35 U.S.C. § 112(f) interpretations as "means-plus-function" language unless specifically expressed as such by use of the words "means for" or "steps for" within the respective claim.

When introducing elements of the present invention or the embodiment(s) thereof, the articles "a," "an," and "the" are intended to mean that there are one or more of the elements. Similarly, the adjective "another," when used to introduce an element, is intended to mean one or more elements. The terms "including" and "having" are intended to be inclusive such that there may be additional elements other than the listed elements. The term "exemplary" is not intended to be construed as a superlative example but merely one of many possible examples.

The following examples further illustrate the present invention but should not be construed as in any way limiting its scope.

EXAMPLES

Materials 1,2-dioleoyl-sn-glycerol-3-phosphocholine (DOPC, Avanti Polar Lipids), 1,2-dipalmitoyl-sn-glycerol-3-phosphoethanolamine-N-(lissamine rhodamine B sulfonyl) (fluorescent liposomes, Avanti Polar Lipids) were used as received for formation of supported lipid bilayers. Unmodified ssDNA oligonucleotides (oligos) in 25 nanomole scale with standard purification, 3' TEG-Chol modified ssDNA oligos in 100 nanomole scale with HPLC purification, 5'-Bn modified ssDNA oligos in 25 nmole scale with standard purification, AP-modified ssDNA oligos in 100 nanomole scale with PAGE purification, and 5'-Atto modified ssDNA oligos in 100 nanomole scale with HPLC purification were all obtained from Integrated DNA Technologies (IDT). For sequences, refer to Table 2. Recombinant human BNP protein (ab87200) was purchased from Abcam, and Streptavidin was purchased from ThermoFisher Scientific. TE buffer 10× (pH=8.0), $MgCl_2·6H_2O$, 3-aminopropyl-triethoxy-silane (APTEs), and PBS (pH=7.5) were purchased from Sigma-Aldrich. The Ag/AgCl reference electrode (RE) and counter electrode (CE) were from Warner Instruments. Glass wafers, 4-in diameter, were obtained from University Wafer Inc.

Example 1: Device Architecture, Fabrication and Characterization

Figure 12:
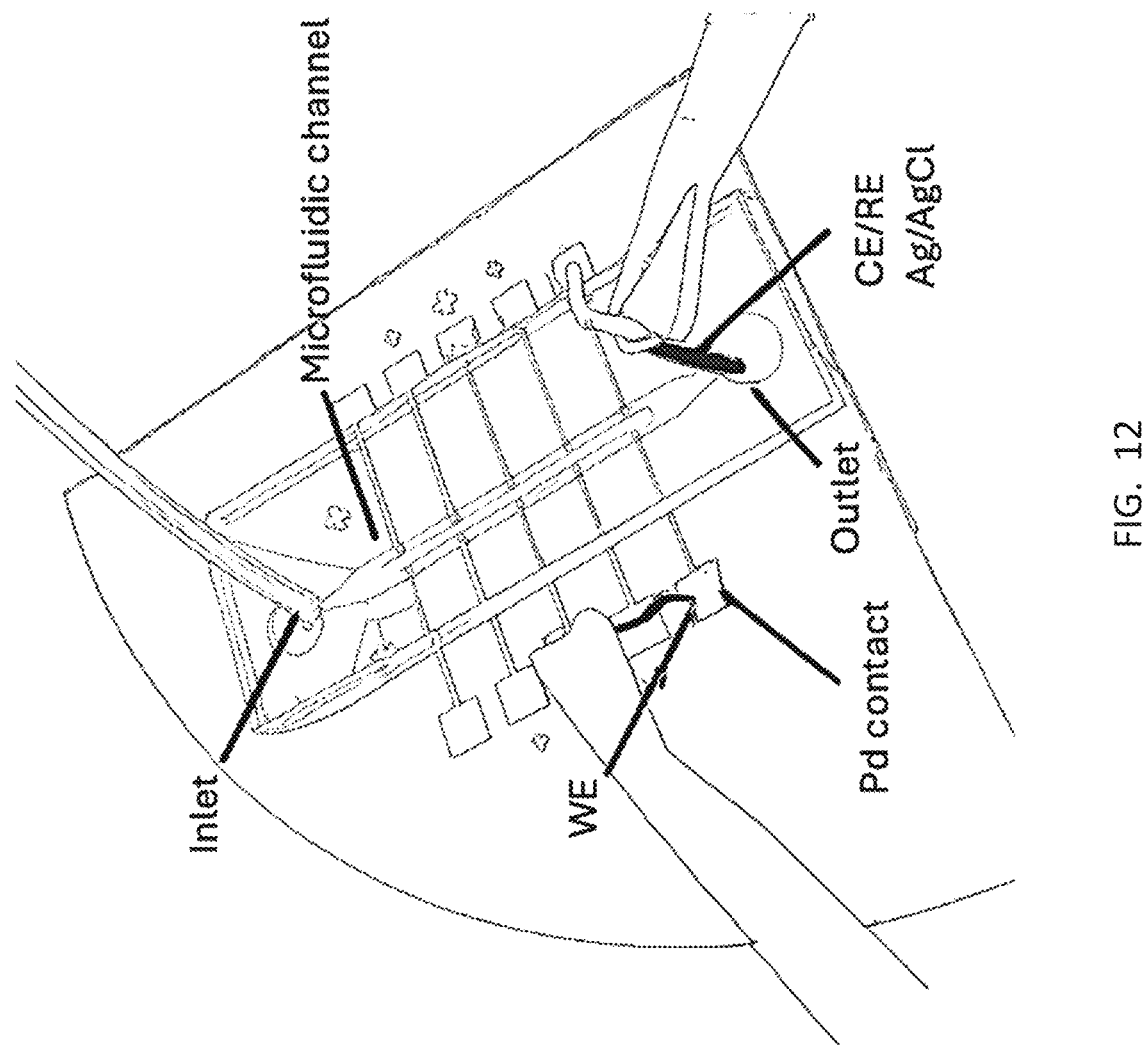
FIG. 12 shows an exemplary microfluidics-based bioprotonic device.
Figure 13A:
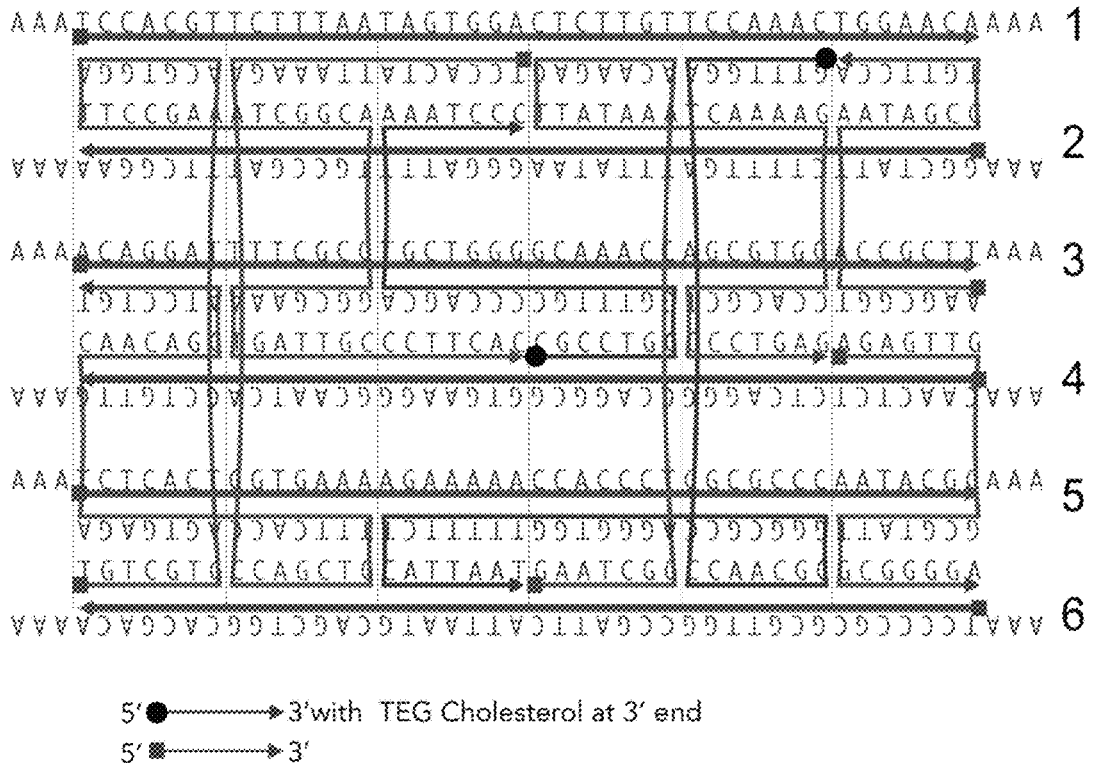
FIG. 13A to FIG. 13B show 6HB-2C nanopore design, conformation and simulations.
Figure 13B:
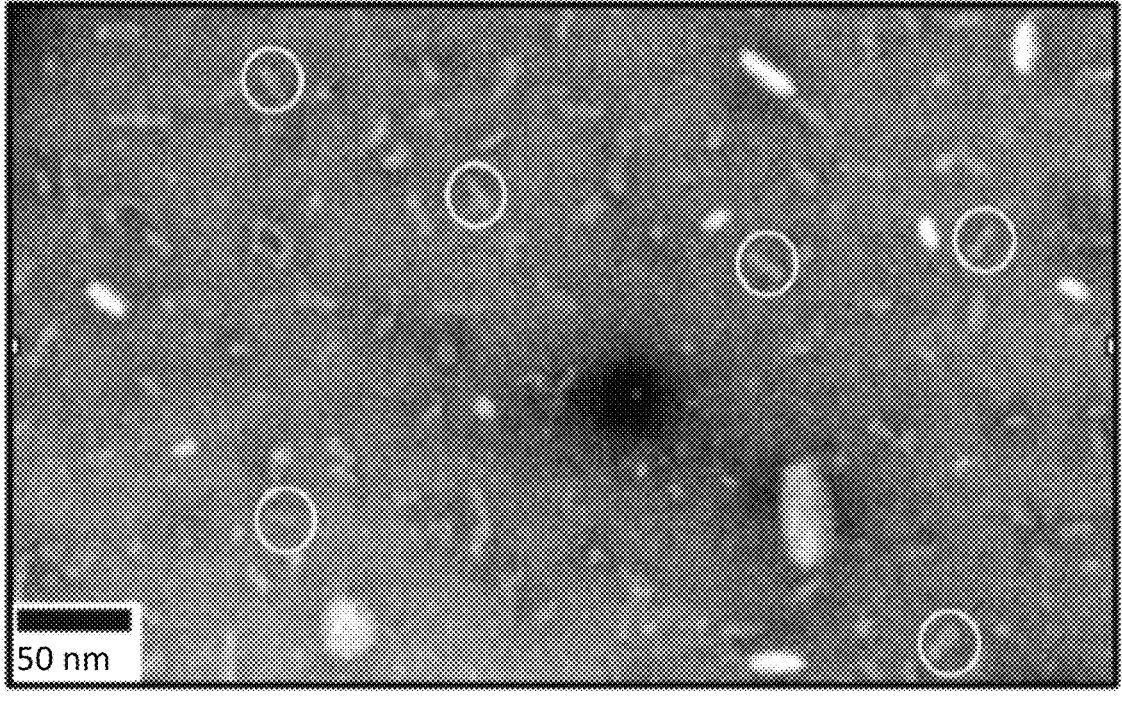

Bioprotonic devices were fabricated with conventional soft lithography and photolithography on a 500 μm thick layer of glass. The SU-8 (photoresist) insulating channel was 10 μm thick, and the PDMS microfluidic channel was 100 μm thick on each chip. The Pd contacts, which served as protodes/electrodes, had a contact area of 0.25 $mm^2$ (500× 500 μm) and a thickness of 100 nm for significant interfacing with lipid solution. The Pd was deposited on top of 5 nm chromium (Cr) adhesion layer via electron beam evaporation. A microfluidic channel confined the flow of liquid to the top of the Pd contact and provides space to insert a reference electrode (RE) and counter electrode (CE; FIG. 12).

Example 2: Lipid Bilayer Formation

In certain fabricated and tested embodiments of the DNA nanopore sensor device, DNA nanopores spanned a supported lipid bilayer (SLB) membrane. In this embodiment, the SLB extended across a chamber with a Pd protode on the bottom and attached to SU-8 photoresist chamber walls, all integrated within a microfluidic architecture (FIG. 8; FIG. 12). In this embodiment, the Pd protode did not have an attached DNA origami with anchoring linkers, nor did the DNA nanopores contain nanopore anchoring linkers complementary to the DNA origami anchoring linkers. Consequently, the DNA nanopores were unanchored and could move fluidly within the membrane as indicated from FRAP experiments described below.

A voltage ($V_{H+}$) between the Pd contact and the Ag/AgCl reference electrode positioned in the solution caused a current of $H^+$ between the Pd contact and the solution, depending on polarity. This flow of $H^+$ induces the electrochemical formation or dissolution of $PdH_x$ that results in a measurable current ($I_{H+}$) in the electronic circuit. Although such an embodiment does not afford the temporal nor spatial resolution necessary to investigate individual ion channel states, it was used to measure the average change in membrane conductance due to ion channel insertion and activity.

Figure 8A:
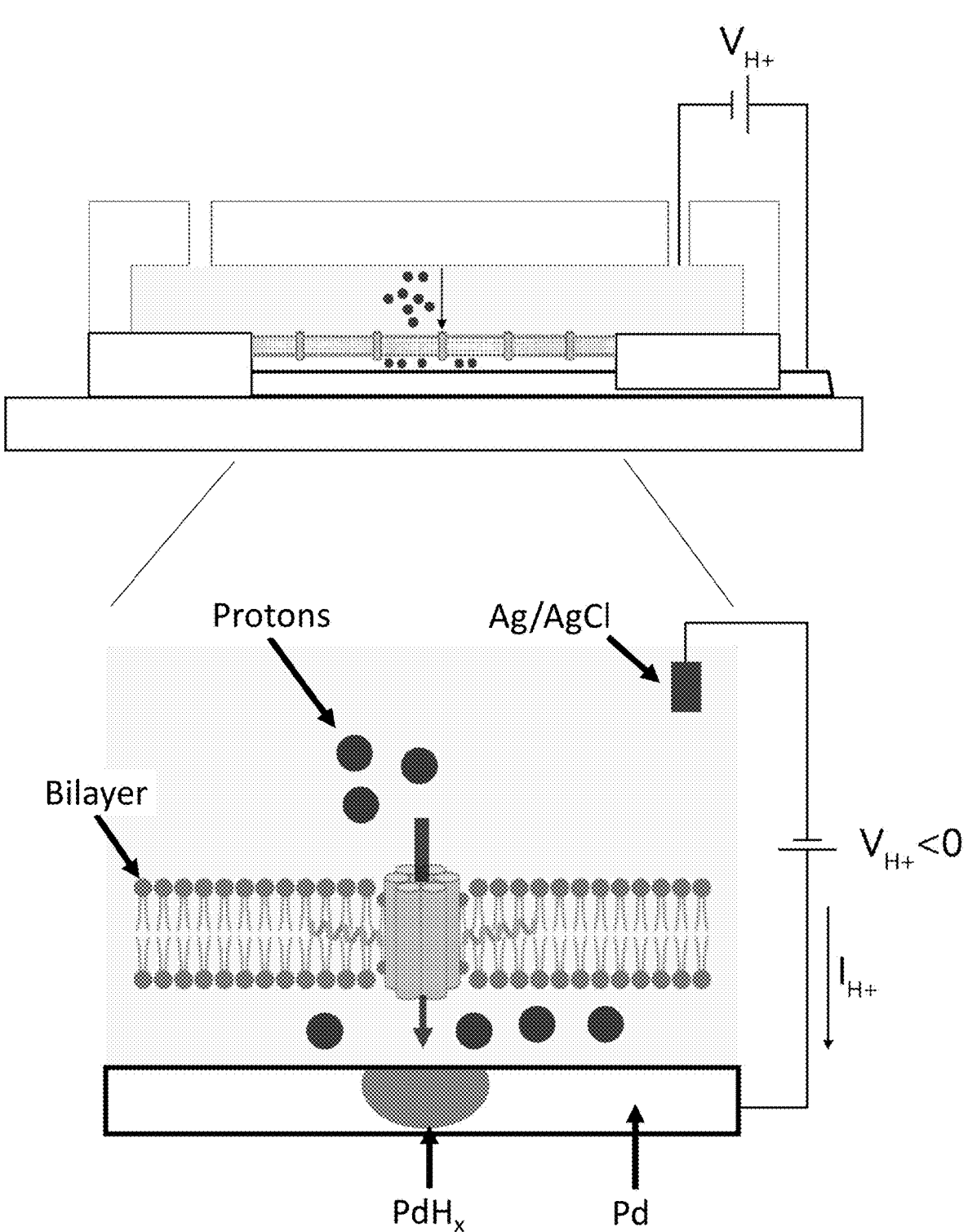
FIG. 8A to FIG. 8F show schematics of bioprotonic devices and related simulated data.
Figure 8B:
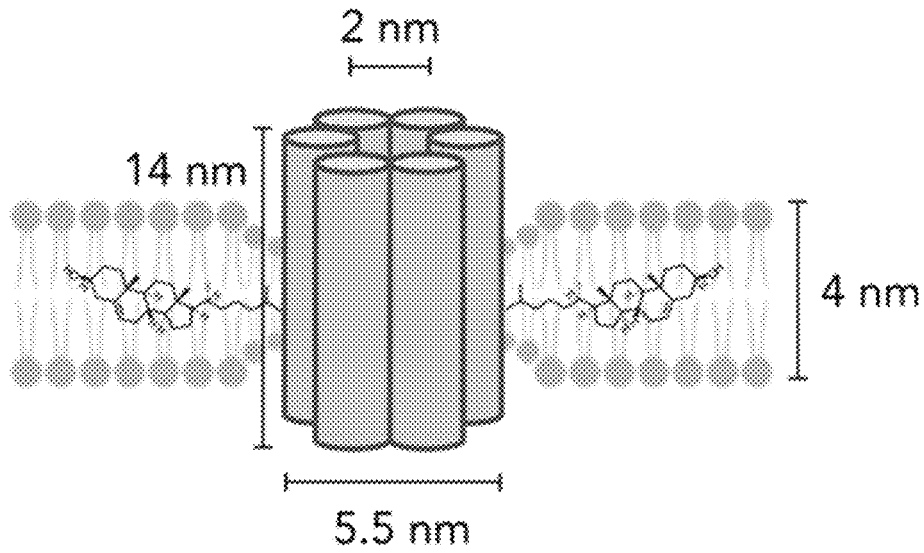
Figure 8C:
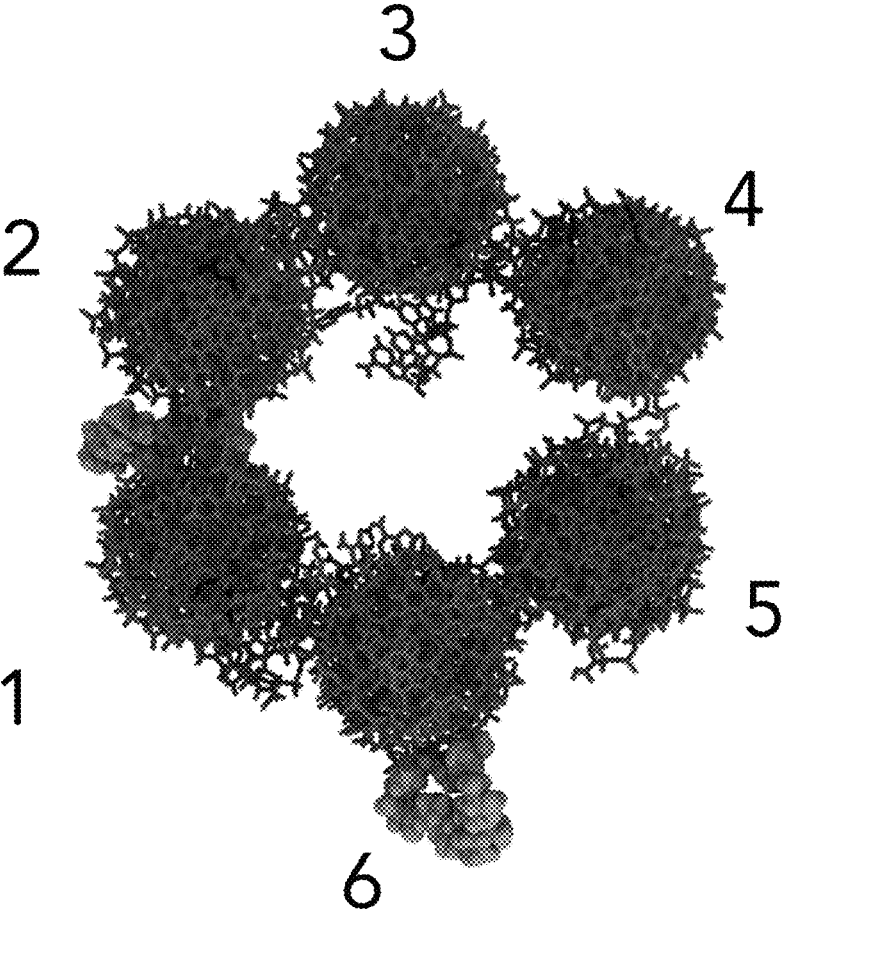
Figure 8D:
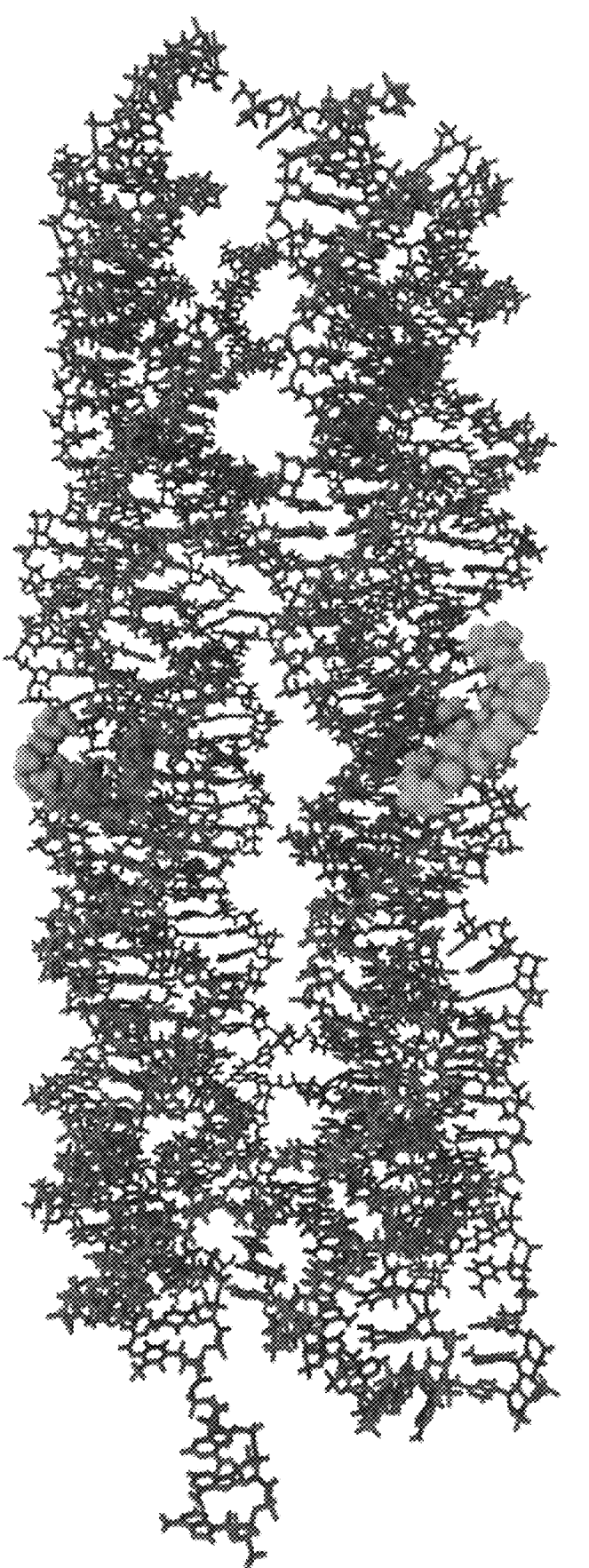
Figure 8E:
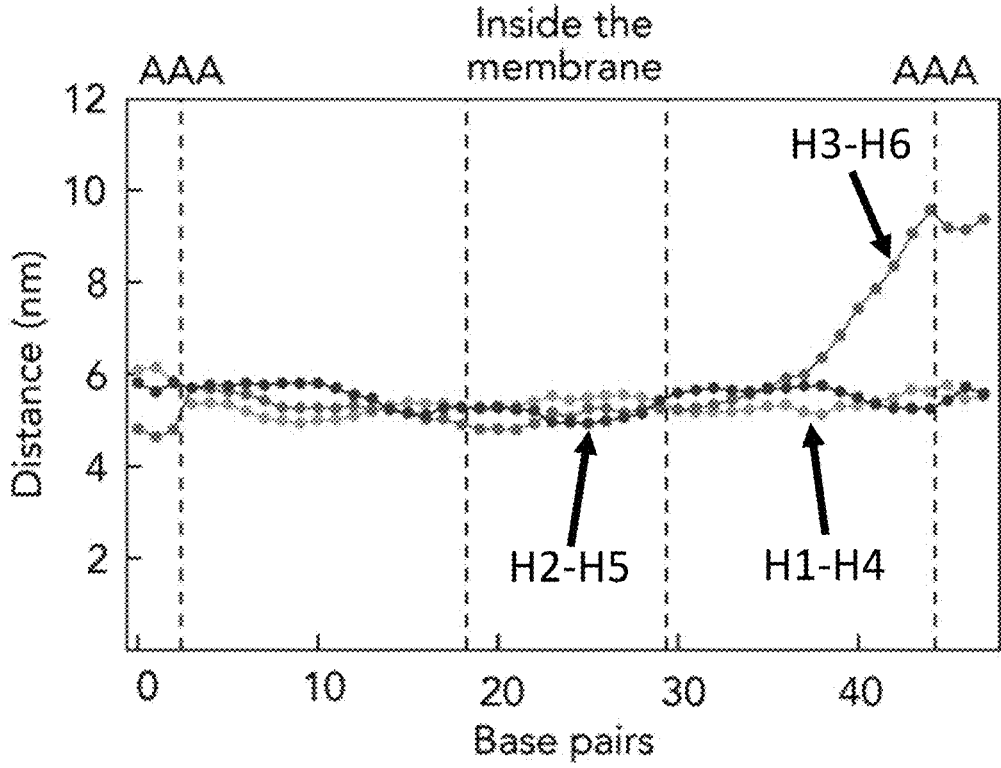
Figure 8F:
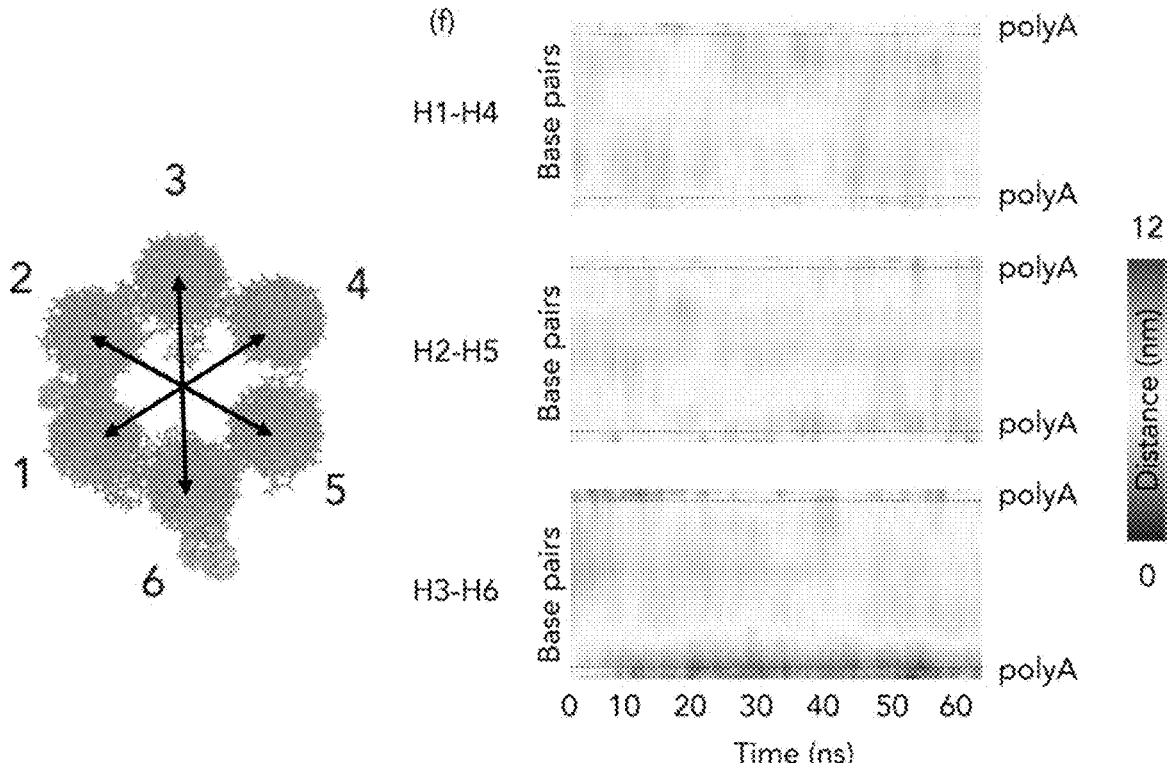
Figure 14A:
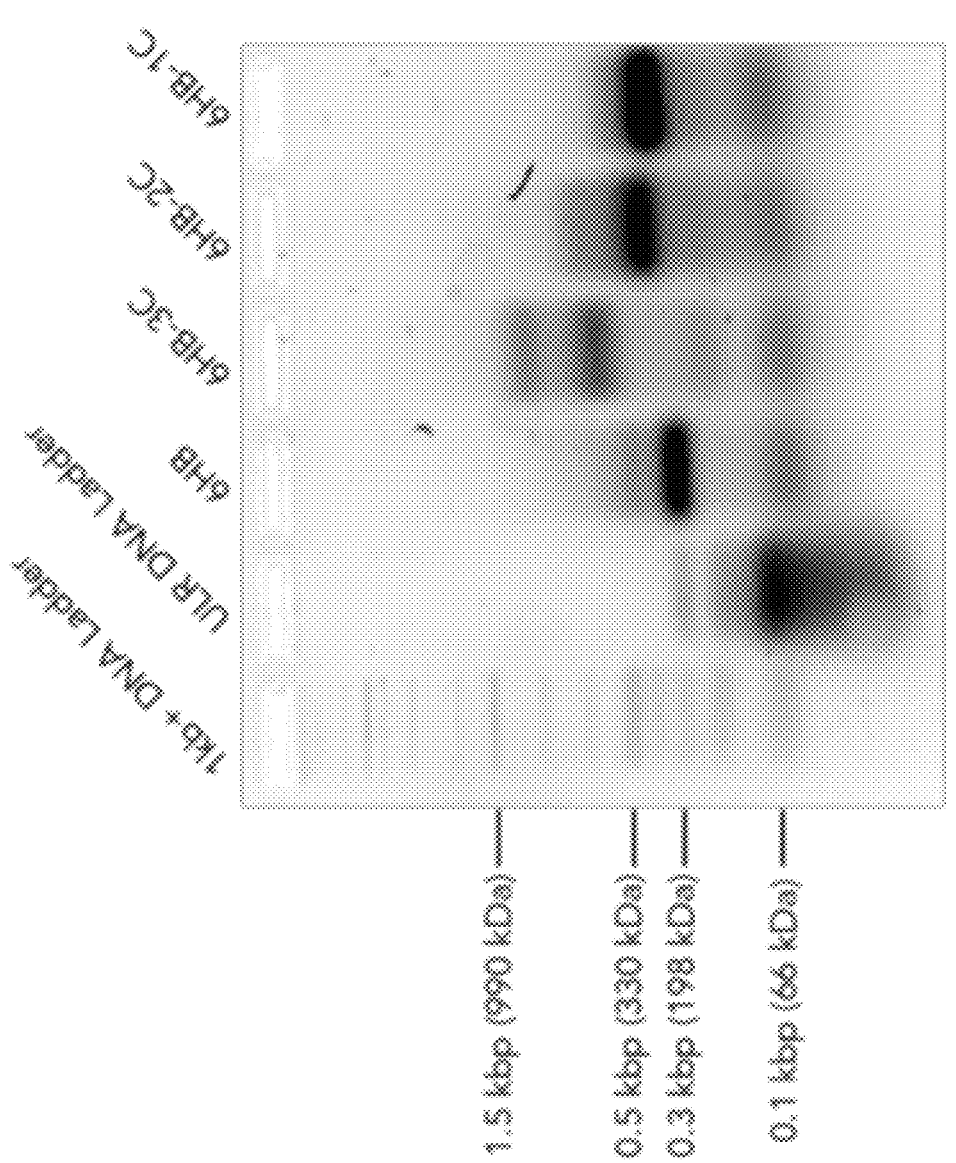
FIG. 14A to FIG. 14D show design and verification of DNA nanopores with cholesterol handles.
Figure 14B:
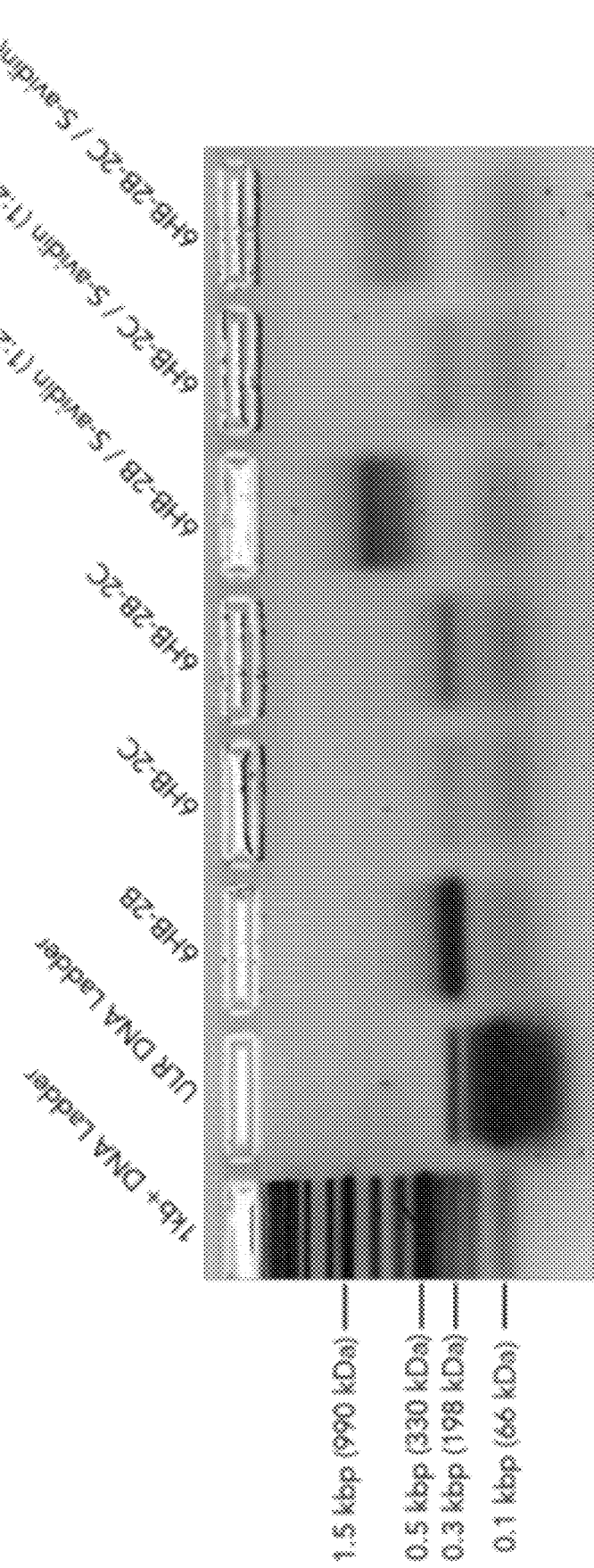
Figure 14C:
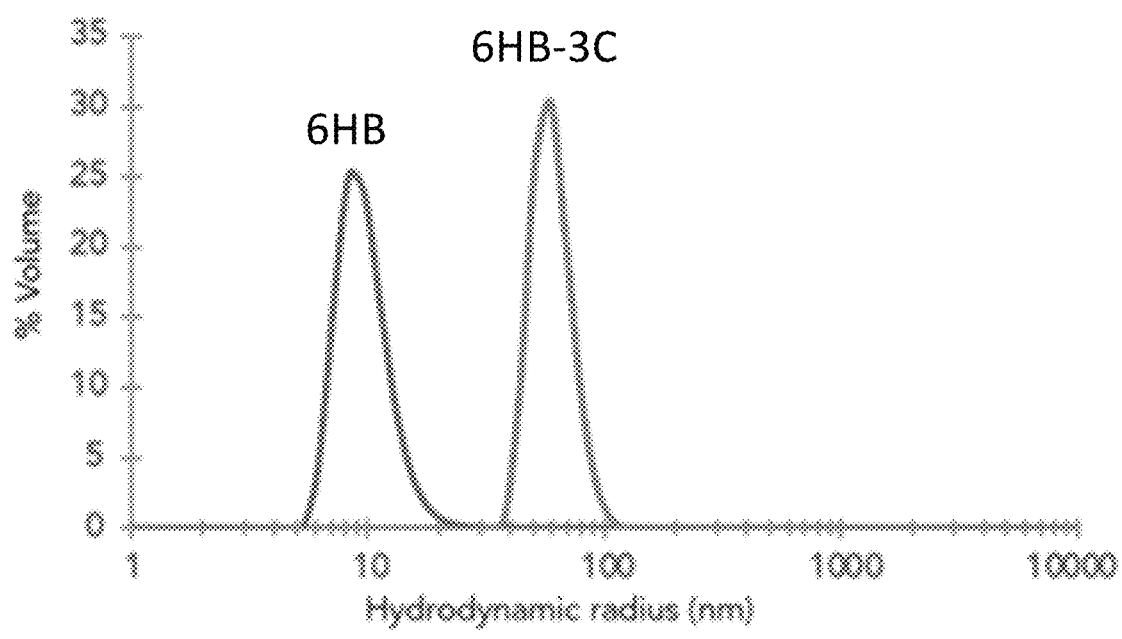
Figure 14D:
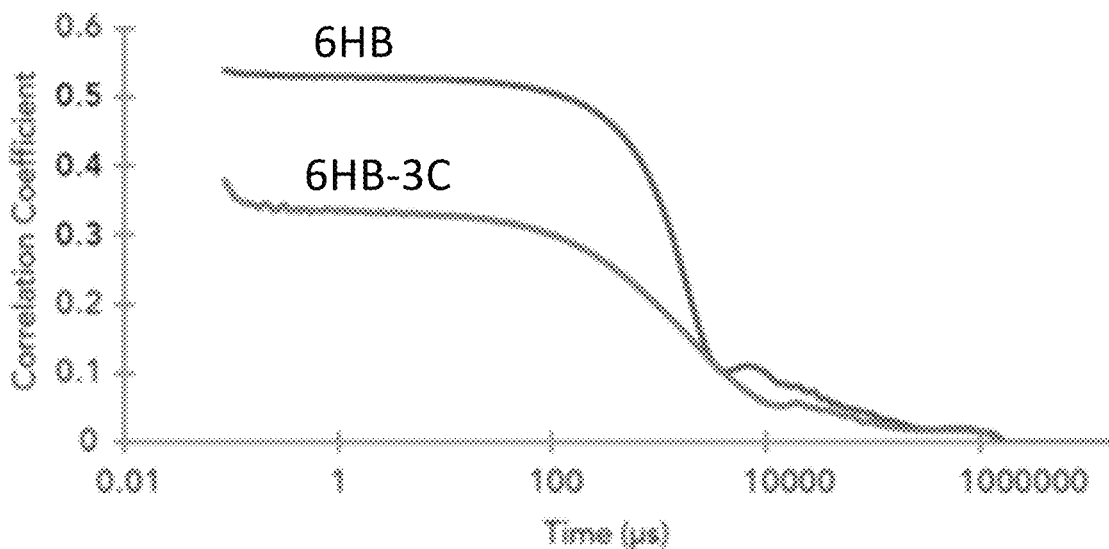

To create biomimicking ion channels that enable $H^+$ transfer across SLB membranes, 14 nm long barrel shaped DNA nanopores were formed via bottom-up, rational design and directed self-assembly (FIG. 8B). A DNA nanostructure geometry consisting of a central physical pore was chosen to enable a large range of signal differentiation upon varied degrees of blockage of the pore. A single stranded tile assembly method was used to design the nanostructure to self-assemble as a nanobarrel-like structure with a hollow lumen from equimolar amounts of 13 short ssDNA strands. To design the strands, the desired geometry was defined in a hexagonal lattice-based DNA design software, caDNAno (open source, caDNAno.org). The hexagonal lattice was filled from top to bottom with an even number of parallel double helices, which were held together by periodic crossovers of the strands. Sequences were randomly generated and then rationally down-selected to maximize primary interactions as designed and minimize secondary and tertiary complex formations. The resulting 13 ssDNA strands (Table 2) were mixed in equimolar amounts to enable one-pot self-assembly into 6 inter-linked Helix Bundles (6HB) that form the walls of the nanopore (FIG. 8B, 8C, 8D). The DNA nanopore was functionalized with tetraethylene glycol cholesterol (TEG-Chol) to provide an anchor for insertion of the hydrophilic DNA nanopores into the hydrophobic environment of the SLB (FIG. 8B, 8C, 8D, FIG. 13, FIG. 14). Transmission electron microscopy (TEM; FIG. 14), dynamic light scattering (DLS; FIG. 14C, 14D) analysis and molecular dynamics (MD) simulations were performed to investigate the dimensions and the stability of the 6HB structure inside the membrane, as well as its pore size under dynamic environments (FIG. 8E, 8F). The average distance between the diametrically opposite DNA helices across the length of the nanopore was analyzed (as depicted in FIG. 8E). The dynamic behavior of these cross helix distances, as they change with time on a base pair level within the DNA nanopore is illustrated in FIG. 8F. Analysis revealed that inside the membrane, the center-to-center distances of the opposite helices ranged between 5 nm and 6 nm. As the radius of a DNA double helix is 1 nm, the average pore size fluctuated between 3 nm and 4 nm. Isolated from the membrane, DNA helices exhibited increased mobility, resulting in some helices moving apart from one another (FIG. 8E, divergent line on plot). However, as seen in FIG. 8F, this phenomenon did not impact the stability of the pore as the TEG-Chol anchors stabilized the DNA nanopore inside the membrane. The length of the nanopore was inferred to provide sufficient area for decoration with hydrophobic anchors to enable spontaneous insertion while projecting essentially beyond the plane of the membrane and enable interactions at the lip of the nanopore without disrupting its stability within the membrane. The small inner lumen size facilitated proton transport across the channel while obstructing proteins and other larger biomolecules, ensuring they remain on the negatively charged side of the nanopore.

For assembly, DOPC liposomes were extracted and dried from a vial containing DOPC and chloroform via nitrogen gas flow and incubation in a vacuum chamber for at least 6 hours to fully dry the DOPC. PBS buffer solution (pH=7.5) was added to the vial for rehydration to a concentration of (1 mg/ml). The DOPC was sonicated and vortexed to promote dissolution of the DOPC, followed by sterile filtration (220 nm sterilizing filters; Millex), which also limited the size of vesicles. Before the deposition of SLBs on Pd contacts, the surface was hydrophilized by oxygen plasma. The vesicle solution was introduced and dispensed in the microfluidic channel and the device was gently agitated for at least 8 hours in high relative humidity (~95% RH) to ensure vesicle fusion and SLB formation, followed by rinsing with buffer solution to wash away unfused vesicle residue.

Supported lipid bilayers mimic cell membranes, electrically insulate the Pd contact, and divide the solution into two volumes, one above (trans) and one below (cis) the membrane. SLBs are not in direct contact with the surface of the solid substrate. The separation offered by this thin layer facilitates the insertion of ion channels, such as the DNA nanopores, by supplying lubrication and mobility to the SLBs.

Example 3: Electrical Measurements

Figure 9A:
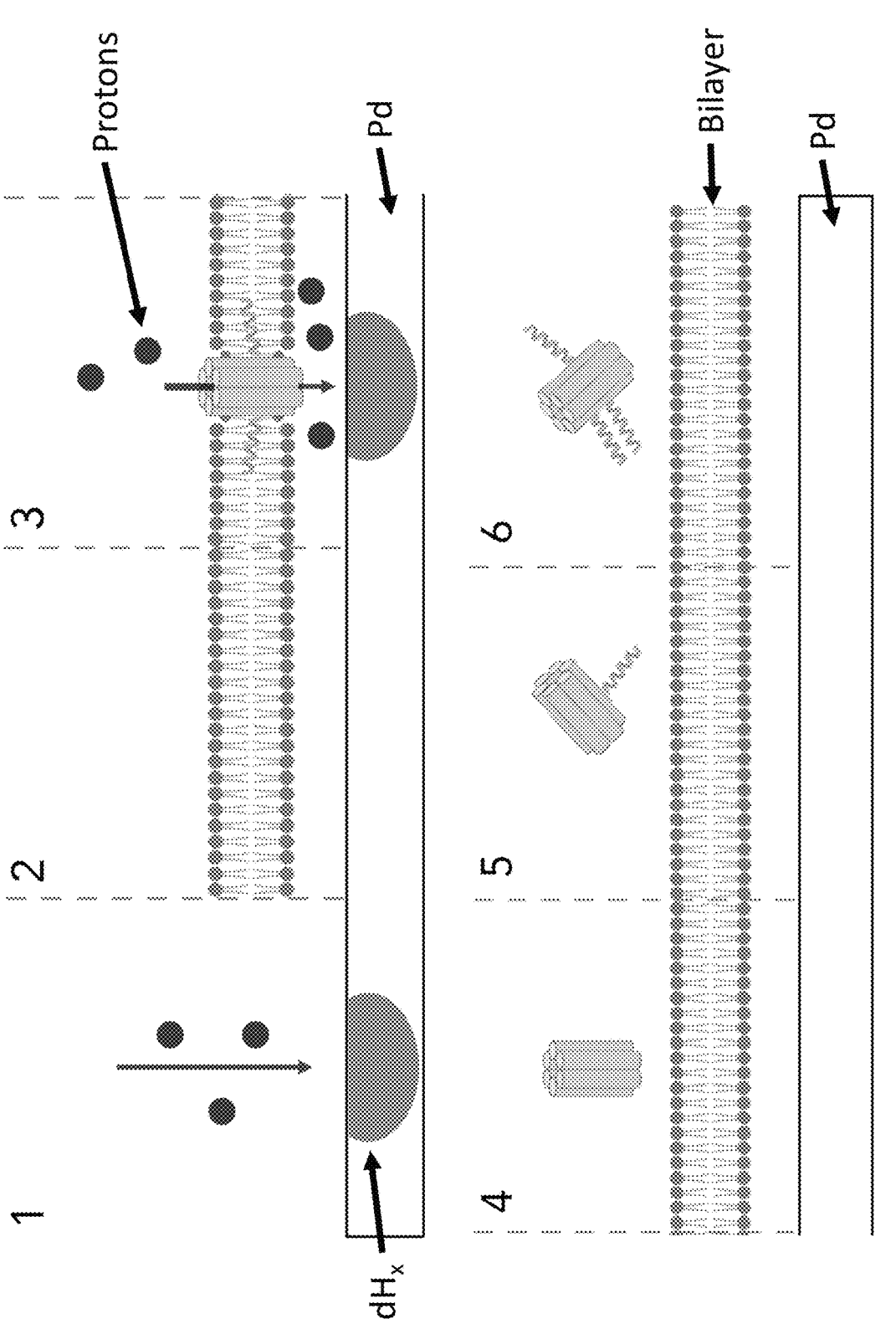
FIG. 9A to FIG. 9C show schematics of control of $H^+$ flow by membrane spanning DNA nanopores.
Figure 9B:
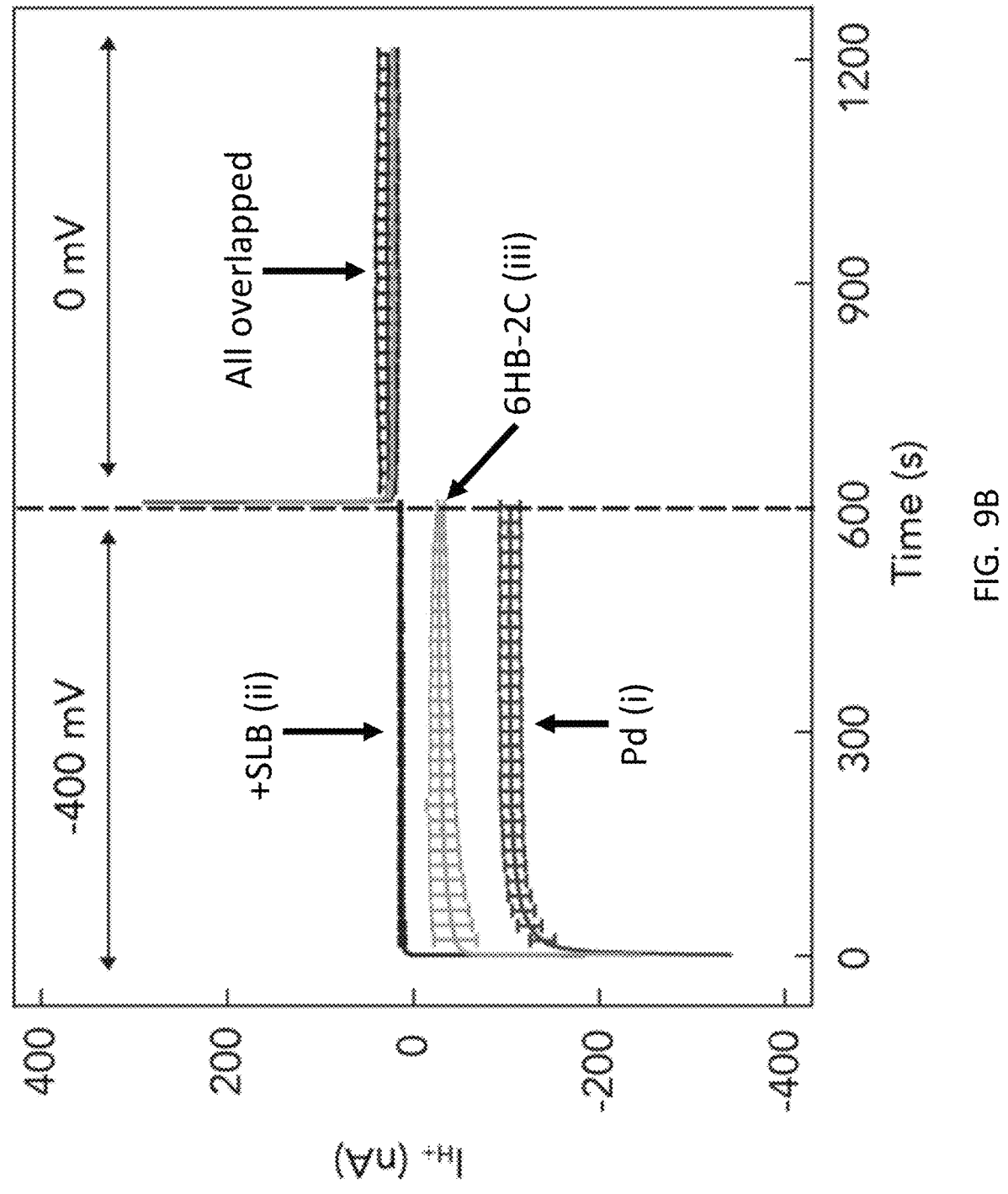
Figure 15A:
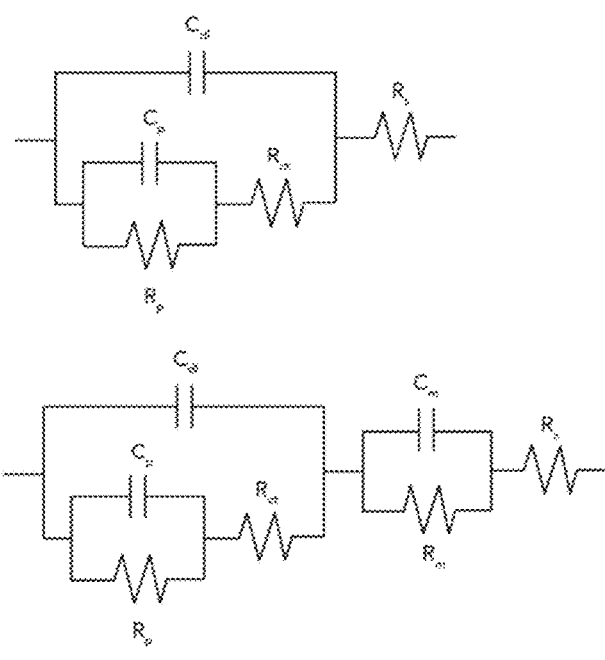
FIG. 15A to FIG. 15C show EIS measurement of a bioprotonic device and lipid bilayer.
Figure 15B:
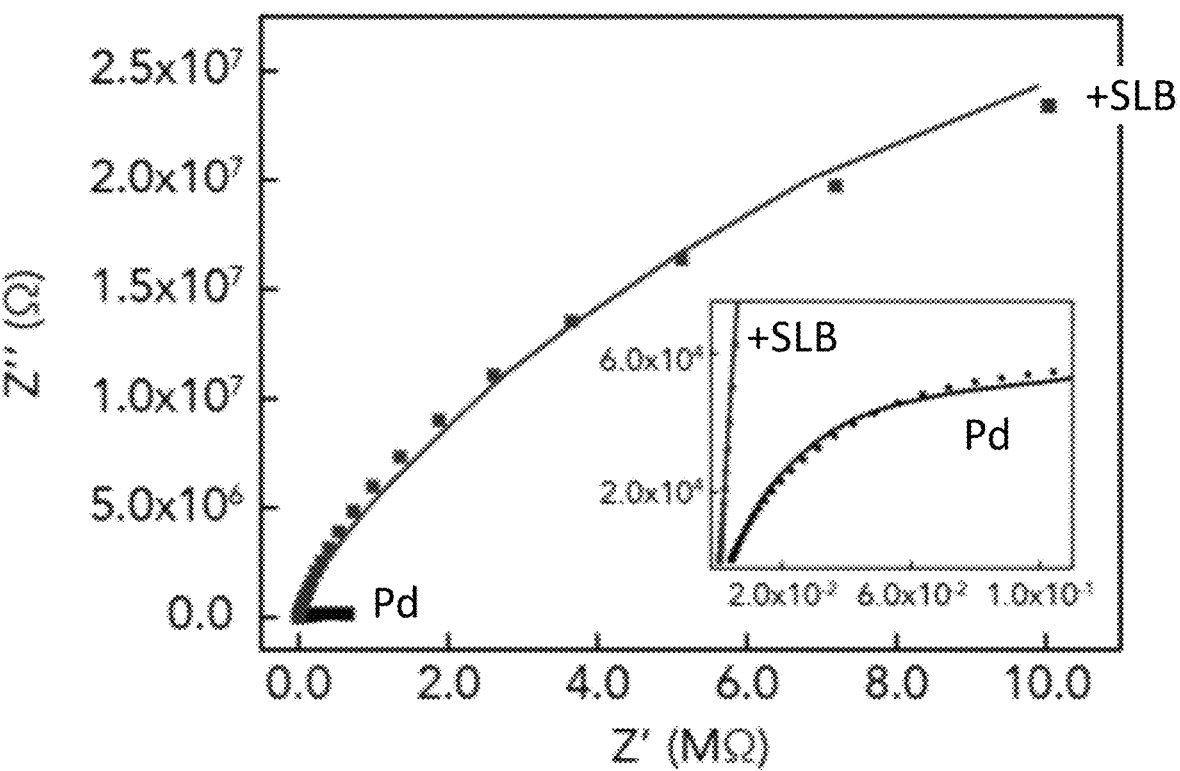
Figure 15C:
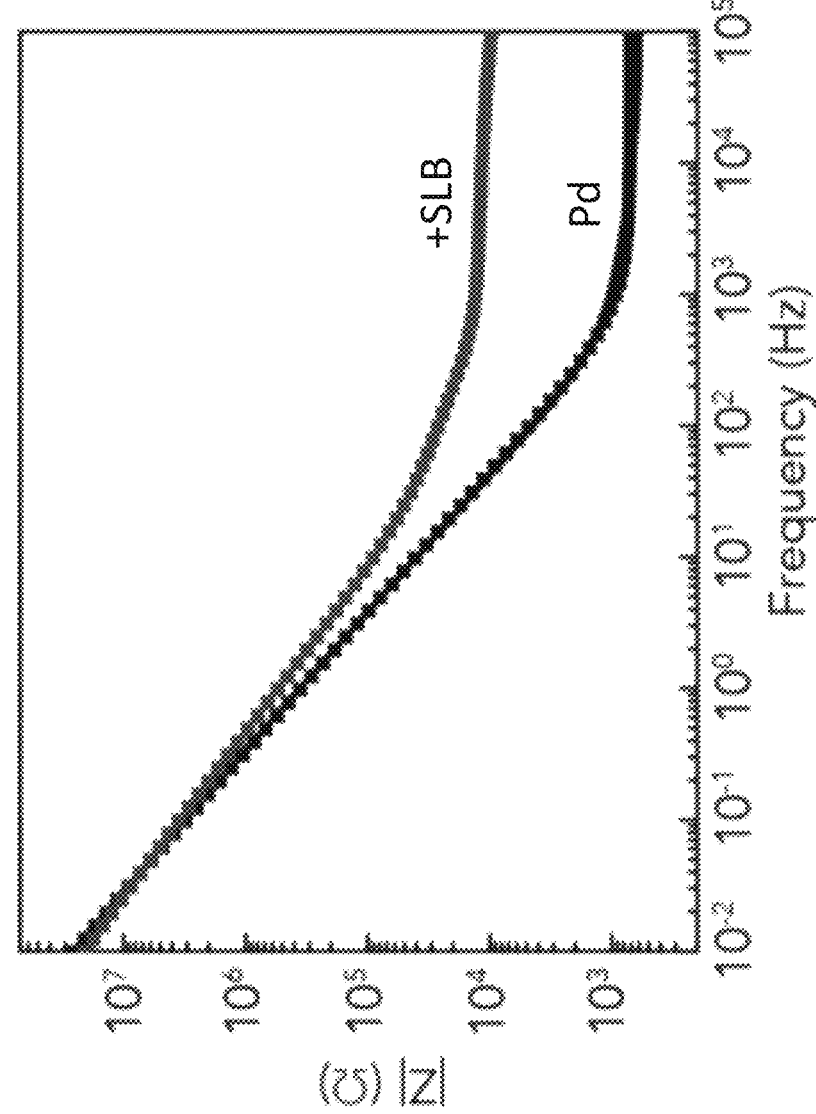

To validate that the DNA nanopore is a $H^+$ conductor, the dependence of $I_{H+}$ to $V_{H+}$ in the DNA bioelectronic device was measured (FIG. 9A). First, it was verified that the bare Pd contact transfers $H^+$ at the solution interface (FIG. 9A-9I). To do so, $I_{H+}$ as a function of $V_{H+}$ was recorded with the following sequence. In the first step, a $V_{H+}$=−400 mV for 600 s induced $H^+$ to flow from the solution into the Pd contact to form $PdH_x$ (FIG. 9A-9I), as indicated by $I_{H+}$=−125±11 nA (FIG. 9B). In the second step, a $V_{H+}$=0 mV transferred $H^+$ from the $PdH_x$ contact into the solution. Here, $I_{H+}$ indicated the prior formation of $PdH_x$ that allowed $H^+$ to transfer from the surface back into the solution even at $V_{H+}$=0 mV because, due to a neutral pH, the protochemical potential of $H^+$ in the $PdH_x$ contact is higher than the protochemical potential of $H^+$ in the solution. The characteristics of the Pd contact were confirmed with Electrochemical Impedance Spectroscopy (EIS; FIG. 15 and Table 1). Second, the SLB was confirmed to create a barrier that blocked $H^+$ transport from the solution onto the Pd surface so that when DNA nanopores were inserted into a SLB, any measured $H^+$ transport originated across the nanopore (FIG. 9A(ii)). Confirmation was achieved as indicated by a $I_{H+}$=−7±1 nA (FIG. 9B). To verify the formation of SLBs, current measurements were repeated and reported the current which are shown as the $I_{H+}$ of 0 nM DNA (FIG. 4a).

The measured current, referred to as the leakage current, indicated that a small amount of $H^+$ diffuse and leak across the bilayer membrane, possibly through the surface defects and were reduced at the Pd surface. After addition of nanopores modified with two cholesterol handles (6HB-2C; 15 nM DNA) to the solution, the nanopores spontaneously inserted into the lipid bilayer (FIG. 9A(iii)) to form membrane spanning ion channels. Insertion resulted in a $I_{H+}$=−52±4 nA for a $V_{H+}$=−400 mV (FIG. 9B), which is significantly larger than the $I_{H+}$ for the SLB in the absence of DNA nanopores and indicated that the DNA nanopores provided a pathway for $H^+$ to move across the SLB. To avoid the accumulation of protons on Pd contact, in the second sequence, the $V_{H+}$ was set to 0 mV. The higher photochemical potential than the electrolyte led to the release of protons into the electrolyte and with positive $I_{H+}$.

Figure 9C:
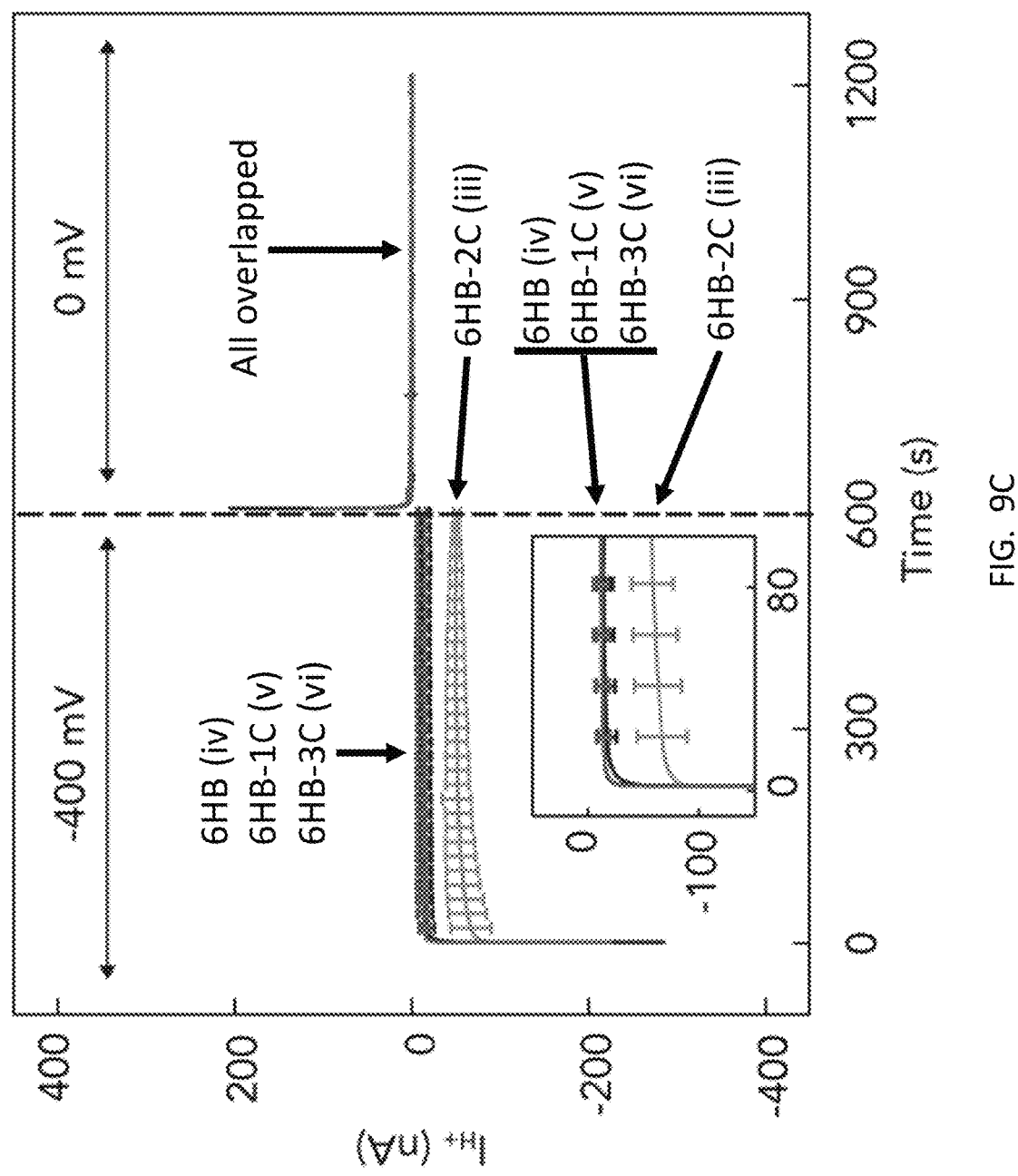

DNA nanopores lacking cholesterol handles did not insert into the SLB (FIG. 9A(iv)), as corroborated by the same observed $I_{H+}$ as recorded for SLB in the absence of nanopore DNA (FIG. 9C). Nanopores with one or three cholesterol handles (6HB-1C, 6HB-3C)(FIG. 9A(v), FIG. 9A(vi)) also did not insert into the SLBs (FIG. 9C). It is likely that 6HB-1C did not insert into the SLBs because one cholesterol handle is not enough to drive the hydrophilic DNA nanopore into the hydrophobic SLBs in a membrane-spanning configuration. However, with the same reasoning, 6HB-3C would be expected to insert into the SLB more efficiently than 6HB-2C. It is likely that the increased hydrophobicity of 6HB-3C drove its aggregation in solution to minimize its interaction with water and made the hydrophobic handles unavailable for insertion into the SLB. This aggregation was confirmed by the appearance of multiple bands for 6HB-3C in gel electrophoresis (FIG. 14A) and a hydrodynamic radius eight times larger than 6HB as measured by DLS (FIG. 14C).

EIS measurements were performed with Autolab, recording impedance spectra in the frequency range between 0.1 Hz-100 kHz. An AC voltage of 0.01 V and a DC voltage of 0 V versus OCP (open circuit potential) were applied (FIG. 15, Table 2).

TABLE 1

| | | | | | | | |
|---|---|---|---|---|---|---|---|
| | $R_s$ (Ω) | $C_m$ (F) | $R_m$ (Ω) | $CPE_{dl}$ (F) | $R_{ct}$ (Ω) | $CPE_p$ (F) | $R_p$ (Ω) |
| Bare Pd | 753.9 | | | $8.08e^{-8}$ | $2.09e^5$ | $1.33e^{-7}$ | $4.55e^7$ |
| Pd/SLB | 753.4 | $6.96e^{-6}$ | $3.95e^{-6}$ | $1.15e^{-7}$ | $4.78e^4$ | $8.92e^{-7}$ | $1.10e^6$ |

Fitted parameter for equivalent circuit model of the bioprotonic device and lipid bilayer Regarding Table 1, the overall impedance of lipid bilayer with the bioprotonic device was found to be higher than that of the bare device, as evidenced by the larger semicircle in the Nyquist plot. However, in the table, the charge transfer resistance (Rct) values were similar between the two systems. This discrepancy can be attributed to the presence of a gap between the lipid bilayer and the device surface, which may result in an additional resistance component, the membrane resistance ($R_m$), which contributes to the overall impedance of the lipid bilayer with bioprotonic devices.

Example 4: DNA Nanopore Programming

Figure 10B:
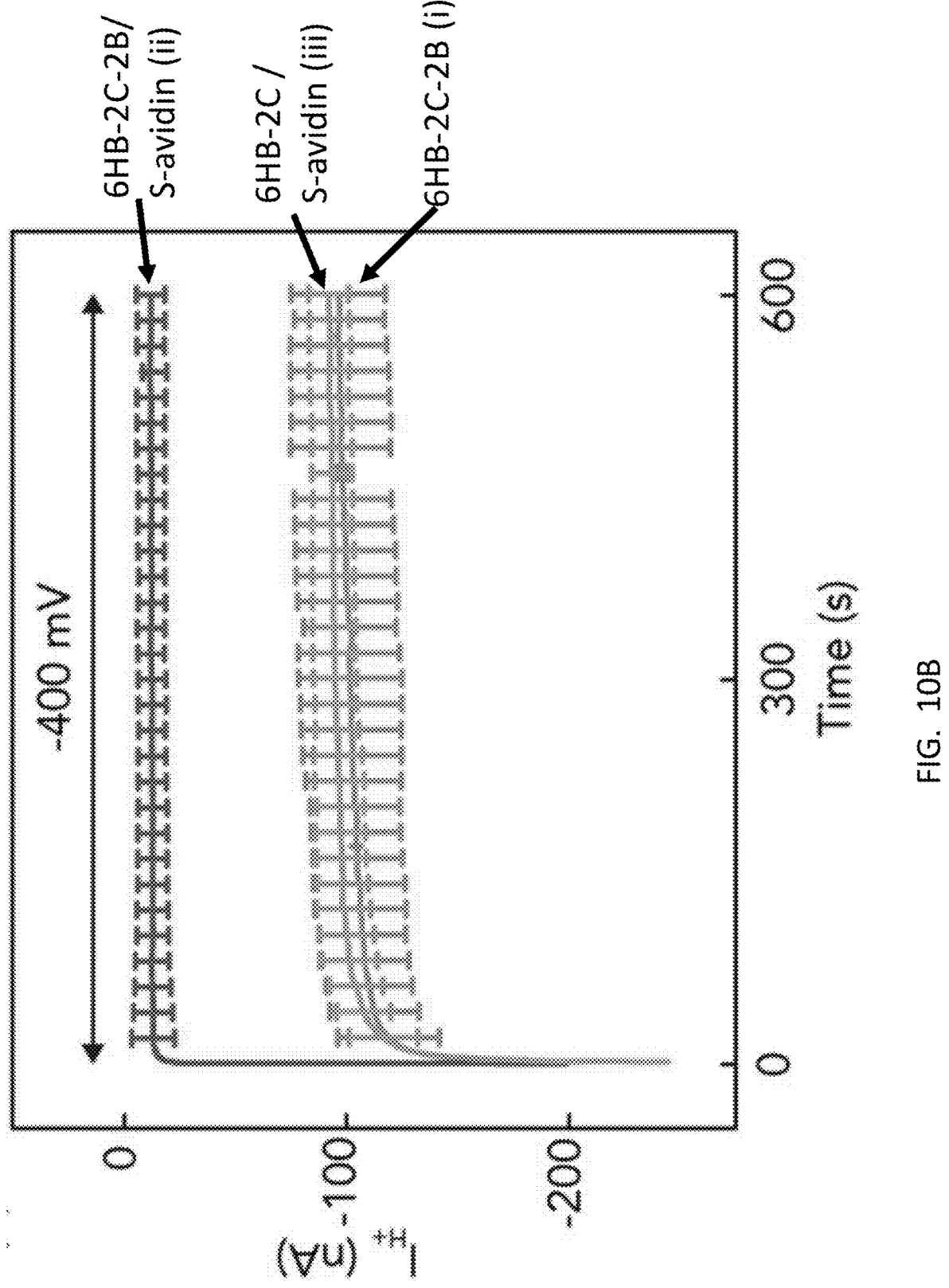

DNA self-assembly allows for programming a desired functionality into the DNA nanopores by designing ad-hoc DNA sequences. As a proof-of-concept for biomolecular sensing, DNA nanopores were designed for the detection of two proteins, streptavidin (S-avidin) and a cardiac biomarker B-type natriuretic peptide (BNP), by including a biotin handle or a DNA aptamer (AP), respectively, on the nanopores. The biotin handle and the AP-DNA aptamer moieties were selected using in-vitro SELEX technology. 6HB-2C nanopores were functionalized using a ssDNA modified with either a biotin handle or the AP handle at their 5' ends, followed by DNA hybridization to obtain the formation of 6HB-2C-2B ("2B" for biotin; FIG. 10A) and 6HB-2C-2AP (for AP; see below) nanopores, respectively. Each specific moiety was designed to reside at either end of the nanopore. To establish a clear current comparison before and after the addition of streptavidin or BNP, the concentration of 6HB-2C-2B and 6HB-2C-2AP was increased to 30 nM. 6HB-2C-2B nanopores inserted into the SLB and resulted in a large ensemble current $I_{H+}=-96\pm21$ nA at $V_{H+}=-400$ mV, indicating that the nanobarrel inside the DNA nanopore aided $H^+$ transport across the SLB (FIG. 10A(i), FIG. 10B). The addition of streptavidin at a concentration 5× the nanopore concentration resulted in a significant decrease in current, to $I_{H+}=-12\pm6$ nA, indicating that the binding of streptavidin to the biotin handle on the DNA nanopore effectively occluded the opening of the nanopore and impeded $H^+$ transport across the SLB to the level of SLB leakage $I_{H+}$ (FIG. 10A(ii) and FIG. 10B).

Figures 17A, 17B:
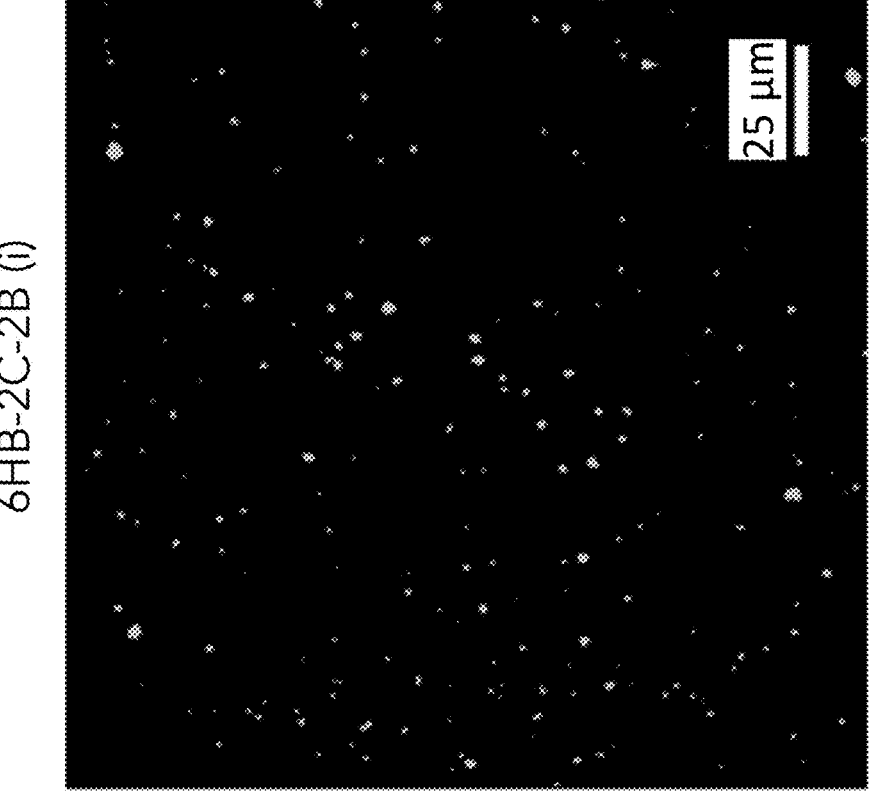
FIG. 17A to FIG. 17B show fluorescence images of 2-cholesterol handled DNA nanopores before and after streptavidin binding.
Figure 18:
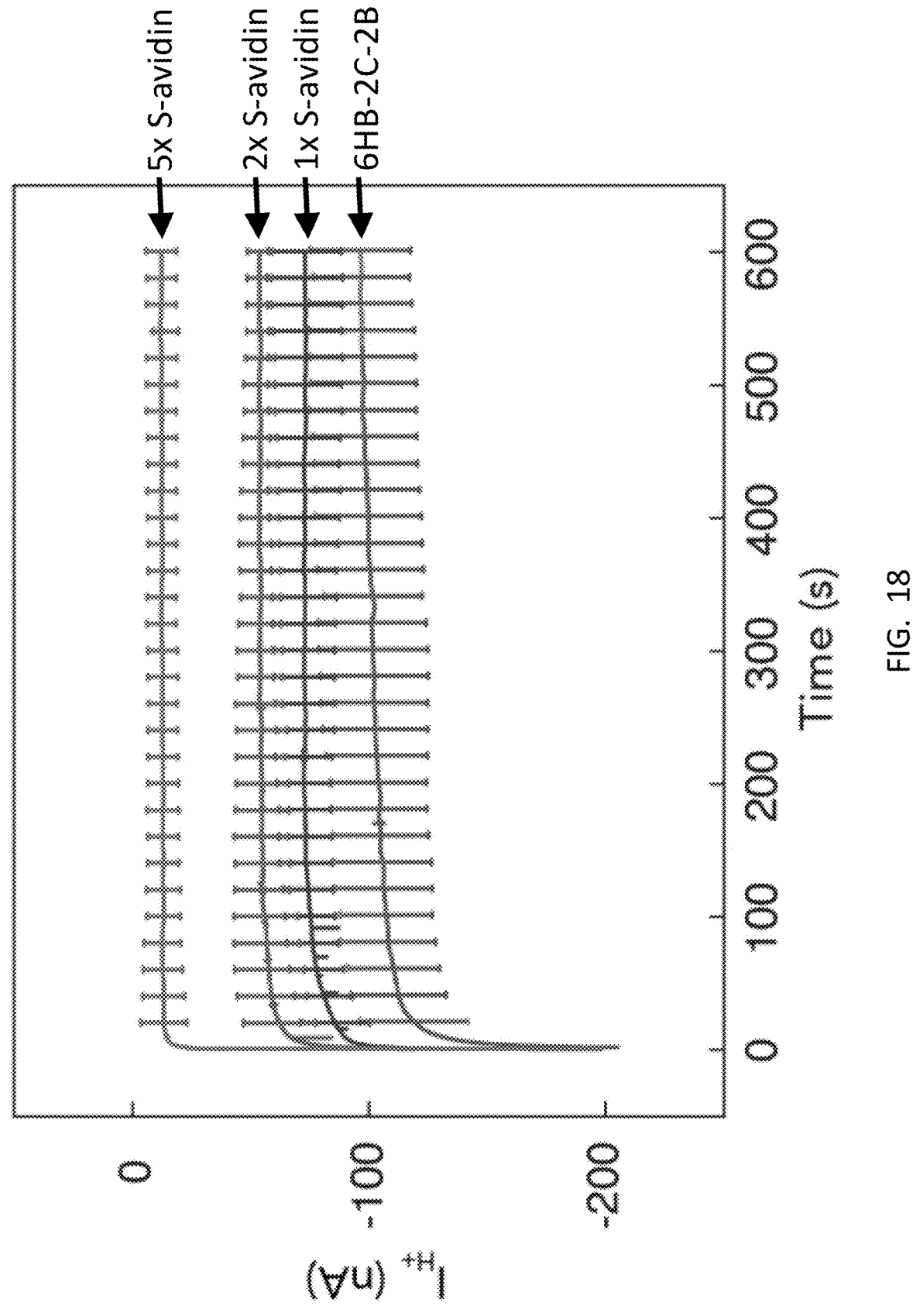
FIG. 18 shows a $I_{H+}$ versus time plot for V=−400 mV under different concentrations of streptavidin. The "6HB-2C-2B" trace represents 6HB-2C-2B; the "1X S-avidin" trace represents 6HB-2C-2B/1X S-avidin (30 nM); the "2X S-avidin" trace represents 6HB-2C-2B/2X S-avidin (60 nM); and the "5X S-avidin" trace represents 6HB-2C-2B/5X S-avidin (150 nM), which is also the same with the 6HB-2C-2B/S-avidin in FIG. 10B. $I_{H+}$ was measured as −96±21 nA, −73±16 nA, −54±5 nA and −12±6 nA for DNA-biotin (6HB-2C-2B), 6HB-2C-2B/1X S-avidin, 6HB-2C-2B/2X S-avidin, and 6HB-2C-2B/5X S-avidin, respectively. Error bars are 1 s.d. (n=3). Increases in streptavidin concentration led to the decrease of $I_{H+}$.
Figure 20:
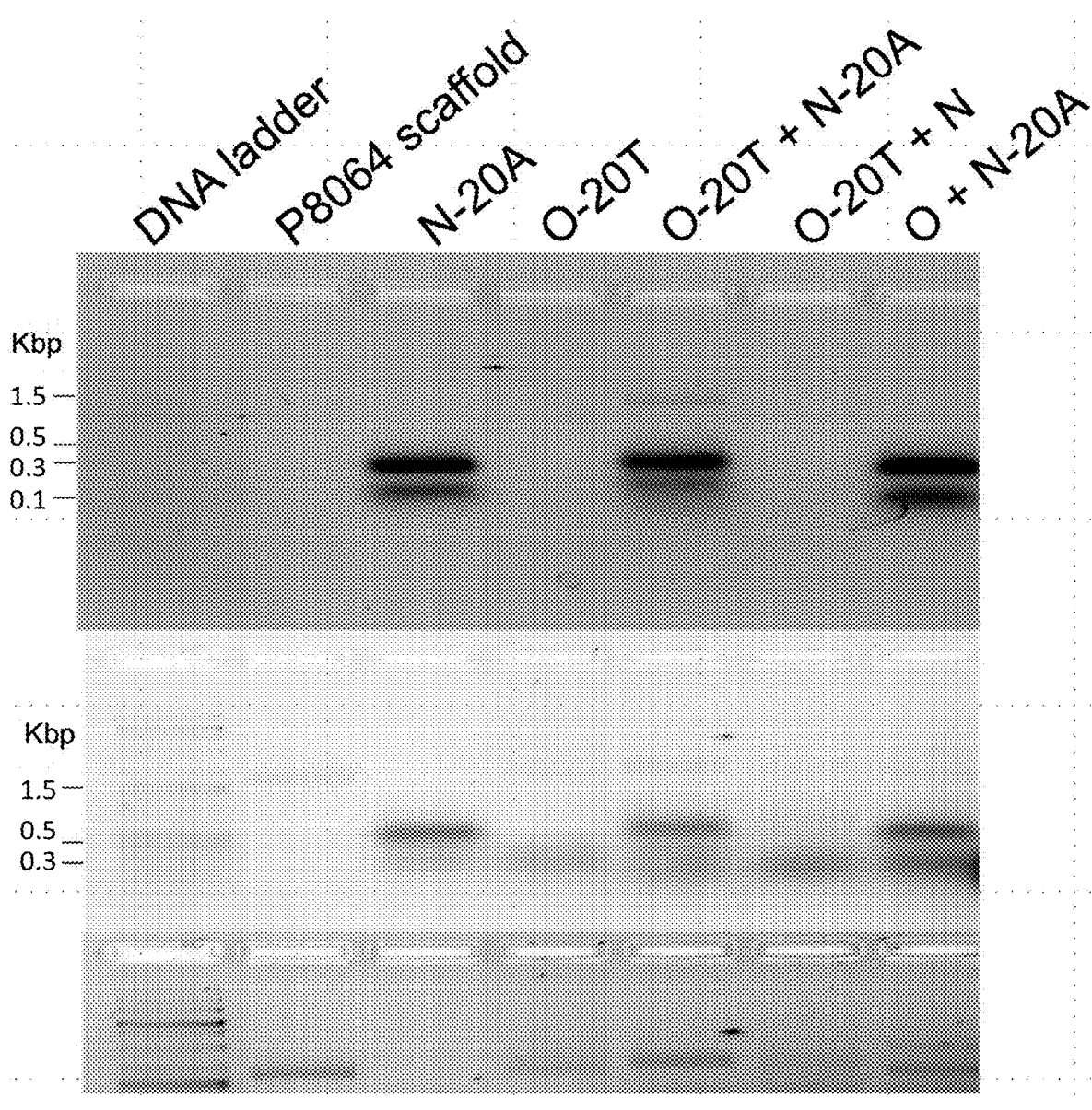
FIG. 20 shows binding of DNA origamis with poly-T anchoring linkers and DNA nanopores with poly-A nanopore anchoring linkers in solution by native gel electrophoresis. Lane 3 shows N-20A (DNA nanopore with 20A nanopore anchoring linker) alone; lane 4 shows O-20T (DNA origami with 20T anchoring linker) alone; lane 5 shows conjugated N-20A and O-20T as a band with mobility equivalent to a DNA standard of about 1.3 Kbp.
Figure 21A:
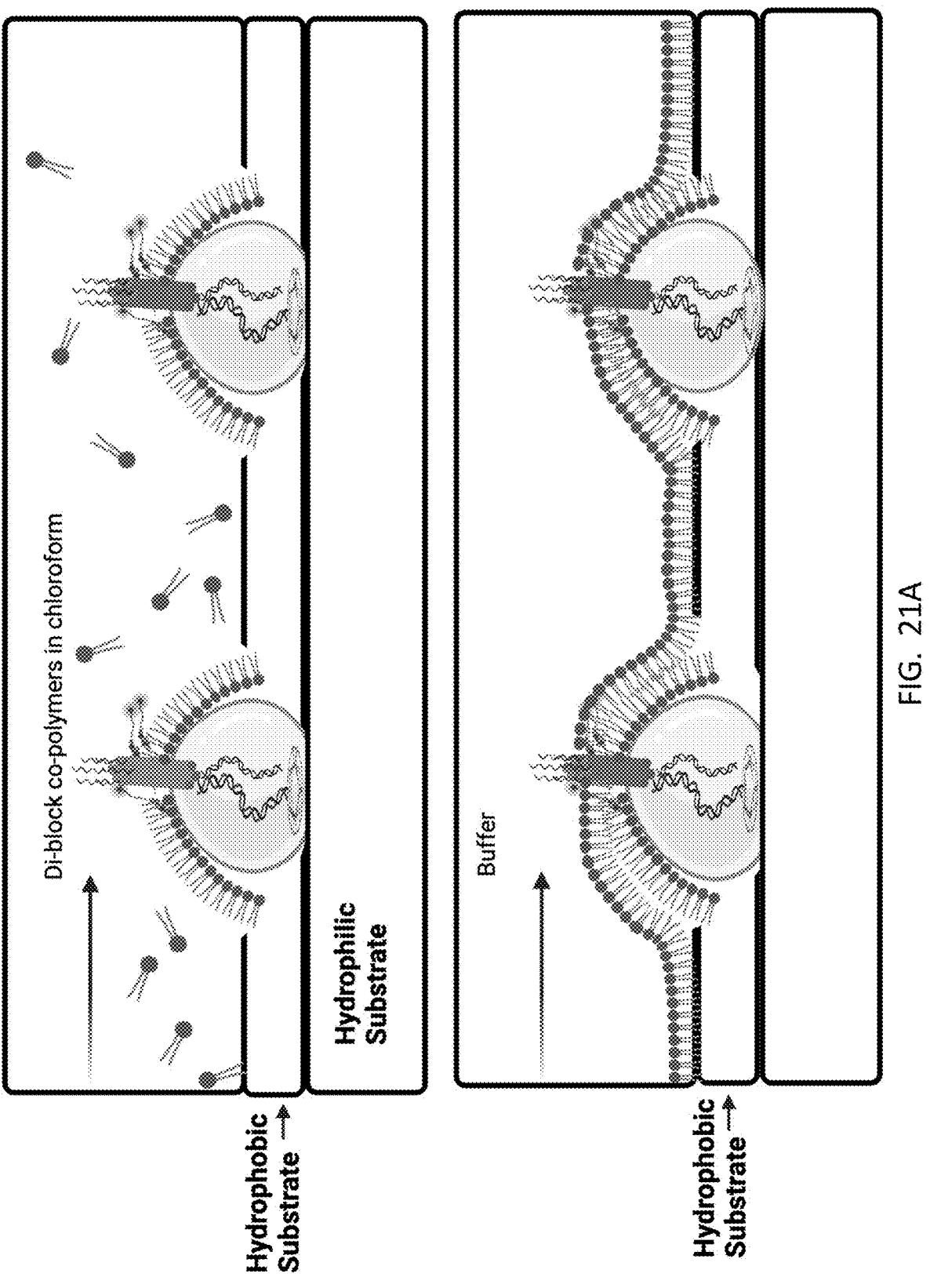
FIG. 21A shows a schematic of self-assembled lipid bilayer formation around membrane spanning pores.
Figure 21B:
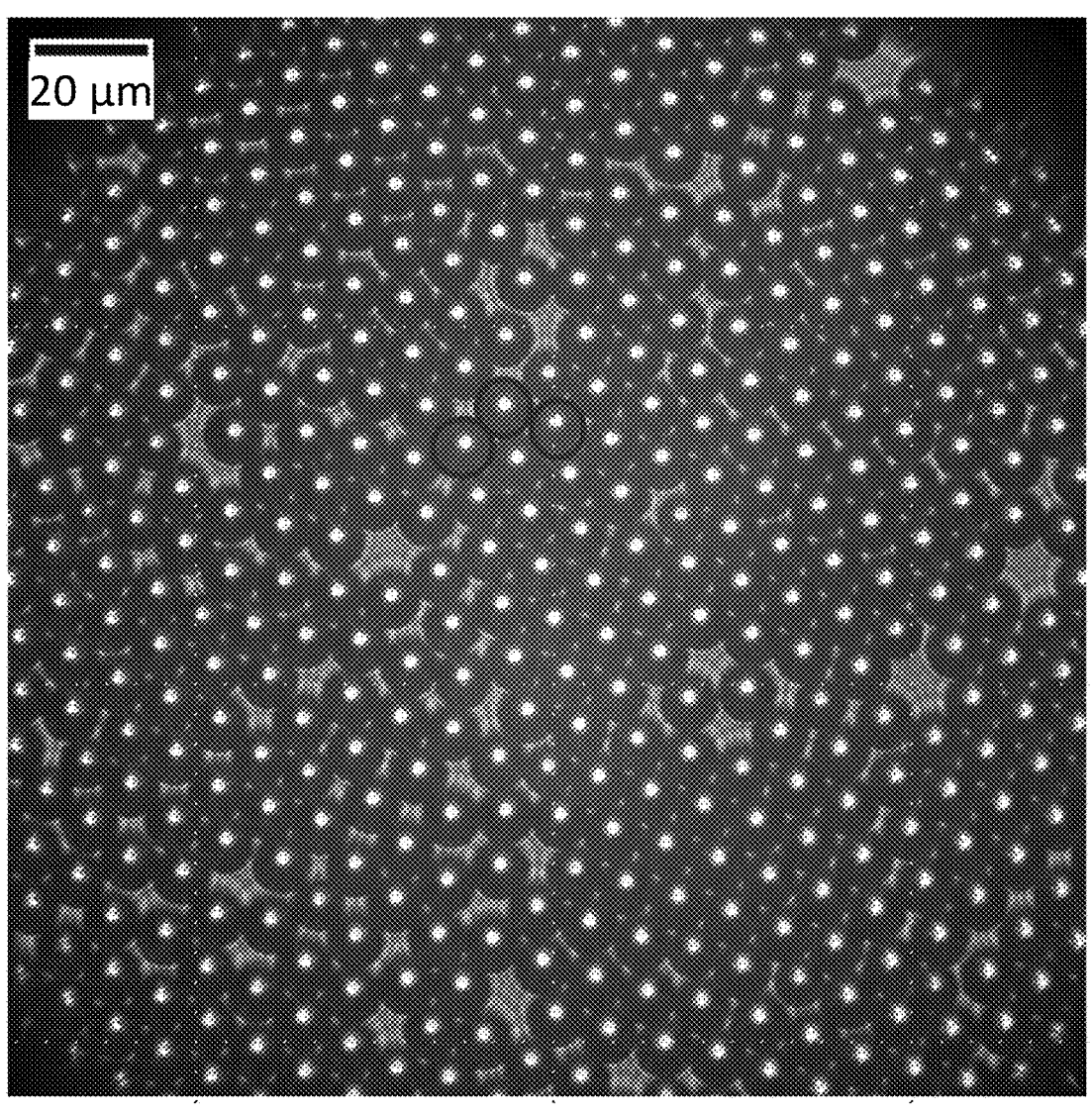
FIG. 21B shows self-assembled arrays of femtoliter chambers based on nanosphere lithography-based patterning of hydrophilic spots on a hydrophobic substrate.

DNA structures without interior pores have been shown to create $H^+$ conduction pathways across a SLB. To confirm that streptavidin is blocking the nanopore rather than, e.g., plugging conduction pathways around the DNA structure, non-biotinylated 6HB-2C were exposed to the same streptavidin concentration (6HB-2C/S-avidin) in solution and did not observe appreciable change in $I_{H+}=-92\pm9$ nA (FIG. 10A(iii) and FIG. 10B) because the streptavidin has no binding site available on the DNA nanopore that would result in the occlusion of the nanopore barrel. To further confirm that the current drop was caused by the binding of streptavidin to the biotin handle and occlusion of the nanopore barrel, fluorescence imaging experiments were performed prior to and after the addition of streptavidin. Fluorescent nanopores were created by modifying certain existing ssDNA strands with Atto 488 tags on their 5' ends (Table 2) prior to the single pot hybridization of the nanostructures. Fluorescent images of DNA nanopores before and after the addition of streptavidin (FIG. 17) demonstrated essentially equivalent numbers of DNA nanopores spanning the SLBs, which indicated binding between streptavidin and biotin blocked the channels and reduced ensemble current rather than other possible phenomena, such as nanopore aggregation or bulk dissociation of DNA nanopores from the SLB membrane. Additionally, the dependence of the $I_{H+}$ on the relative concentration of streptavidin with respect to the concentration of the biotin tagged nanopores was measured. Increasing streptavidin concentrations led to a greater number of blocked channels and a more pronounced decrease in current (FIG. 18).

Figure 10D:
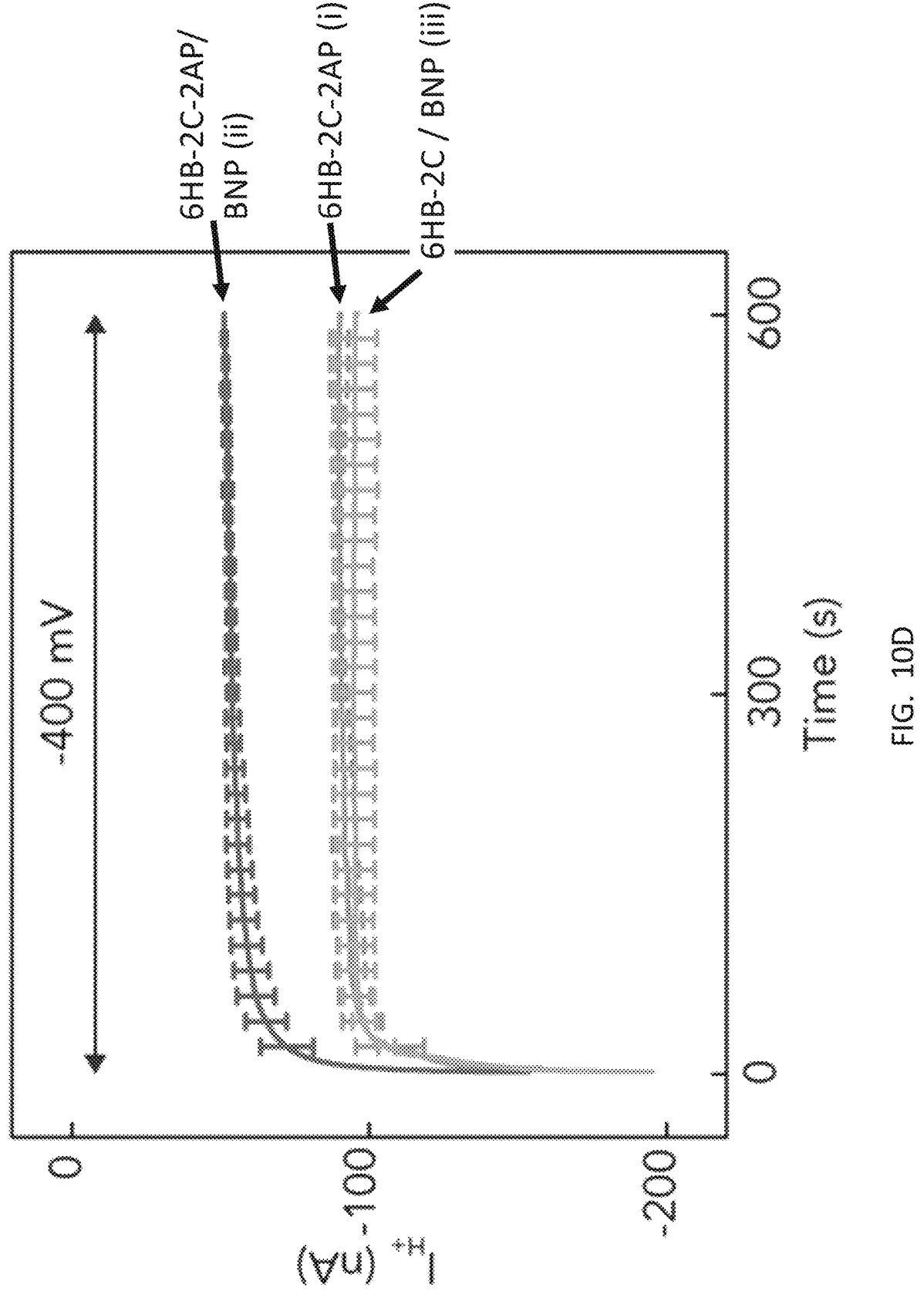

Similar experiments and controls were conducted with 6HB-2C-2AP nanopores. For the same concentration of 6HB-2C-2AP (FIG. 10C) nanopores as those of 6HB-2C-2B nanopores, the $I_{H+}$ observed at $V_{H+}=-400$ mV was $-90\pm3$ nA (FIG. 10C(i) and FIG. 10D). Like the biotin-tagged nanopores, the DNA aptamer-tagged nanopores inserted themselves into the SLB to form membrane-spanning ion channels and resulted in $H^+$ transport across the SLB. When BNP protein was introduced into the environment in five times excess concentration with respect to the nanopore concentration, a reduced $I_{H+}$ of $-51\pm1$ nA was observed (FIG. 10C(ii) and FIG. 10D) at $V_{H+}=-400$ mV. This showed that the affinity interactions between AP-BNP at the lip of the ion-channels blocked the transport of $H^+$. The smaller reduction in current in the case of AP-BNP compared to the dramatic reduction observed in biotin-streptavidin was attributed to the weaker interaction affinity ($k_D$ of $12\pm1.5$ nM) as compared against strong affinity of biotin-streptavidin ($k_D$ of $10^{-1}$ nM). Similarly, as control, exposing non-aptamer modified 6HB-2C nanopores to the same BNP concentration in solution (6HB-2C/BNP) did not cause any appreciable change in $I_{H+}$ of $-96\pm9$ nA (FIG. 10C(iii) and FIG. 10D) because the BNP has no binding site available on the DNA nanopore that would have resulted in the occlusion of the nanopore. By leveraging the programmability offered by the DNA nanostructures, nanopores were engineered to demonstrate an electronic sensing response to a specific analyte in in-vitro environments without the need for modifying the analyte.

Example 5: Fluorescence Imaging and Fluorescence Recovery after Photo-Bleaching Measurements (FRAP)

Figure 16A:
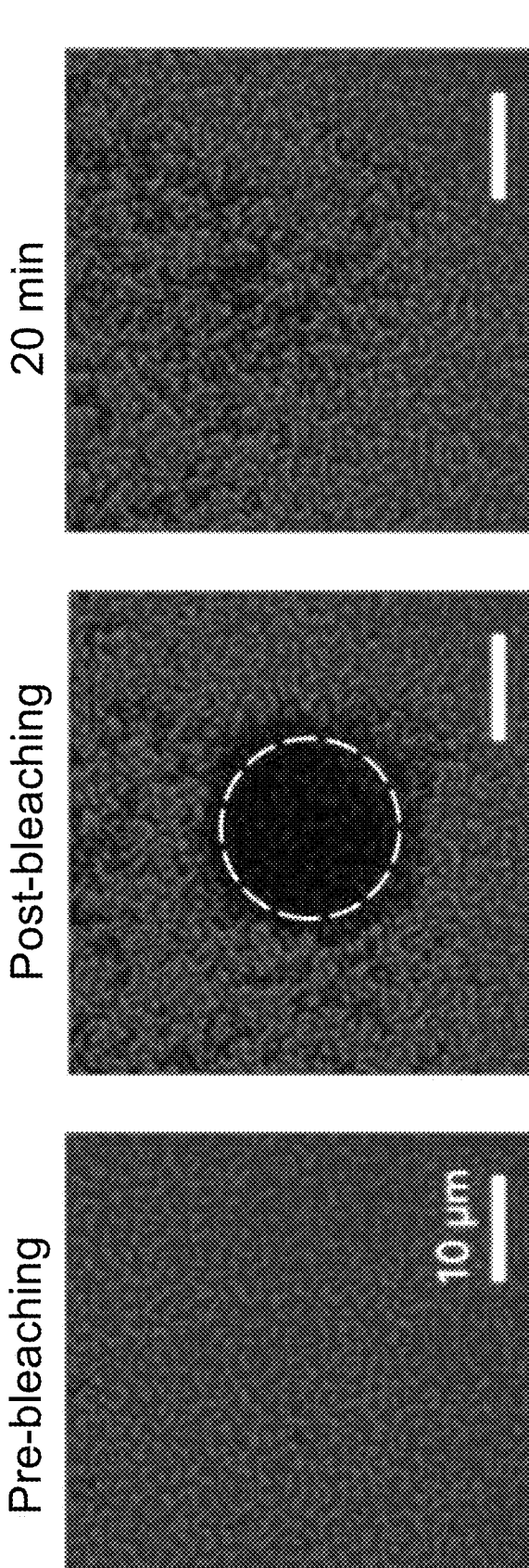
FIG. 16A to FIG. 16C show the characterization of lipid bilayer formation on Pd by FRAP.
Figure 16B:
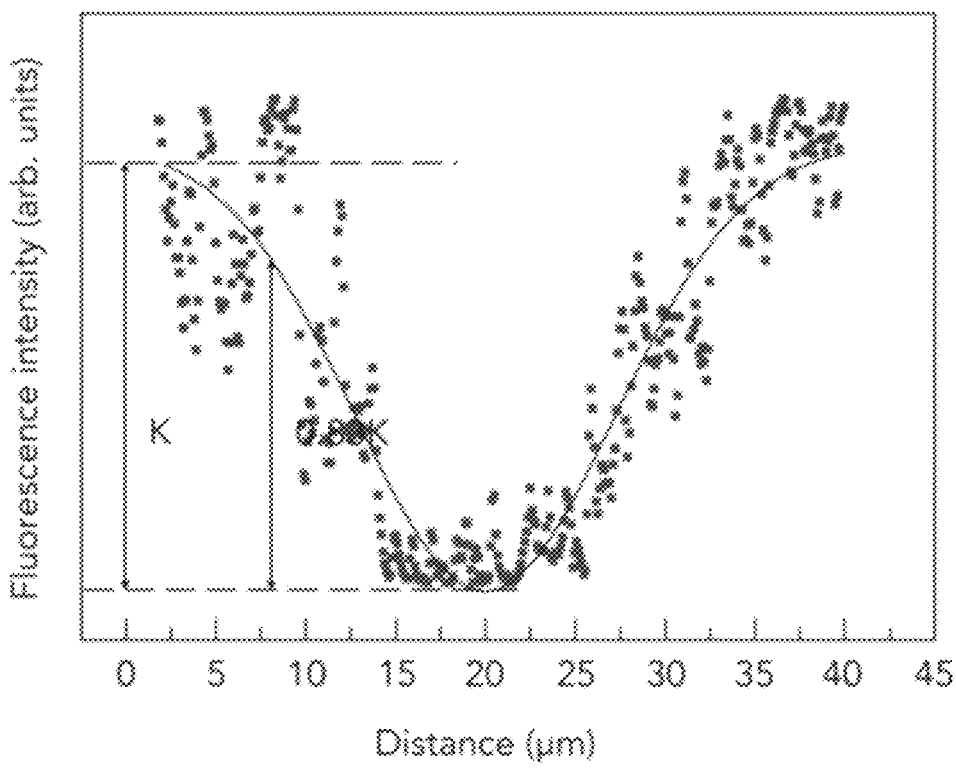
Figure 16C:
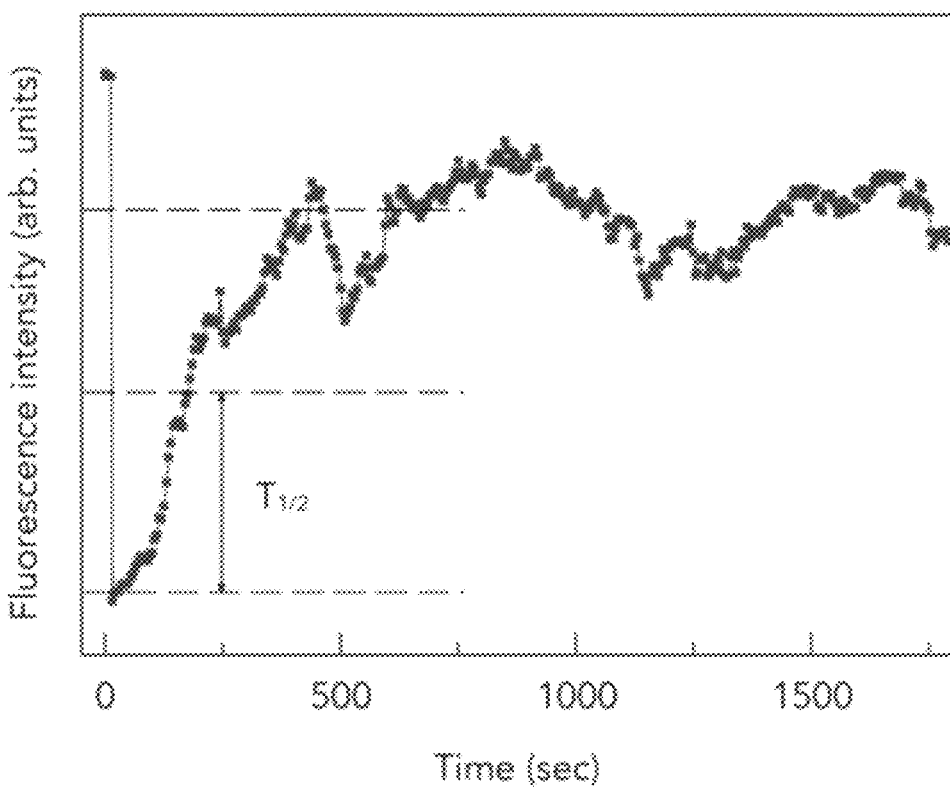

The formation and quality of SLBs were validated by Fluorescence Recovery After Photobleaching (FRAP; FIG. 16), where fluorescent liposomes were combined with the DOPC lipids to form the bilayer. The samples were flushed with PBS buffer several times to remove excess fluorophores. Fluorescence imaging and FRAP experiments were performed on confocal microscopy (Leica, SP5 Confocal Microscope) with a 63× water immersion objective. DNA nanopores tagged with 488 Atto fluorophores on either end of the nano barrel were used for the fluorescence imaging experiments. A 488 nm Argon laser was used for fluorescence imaging, and 543 nm and 594 nm HeNe laser was used for photobleaching. A 20 μm diameter spot in the supported lipid bilayer was photobleached, and its fluorescence intensity recovery was monitored for 30 min. The fluorescence intensity of diameter and changes over time were analyzed with Image J and fitted using a Gaussian function. The diffusion coefficient was calculated with the below equation:

$$D = \frac{R_n^2 + R_e^2}{T_{1/2}}$$

where Rn is the nominal radius from the user defined spot, Re is the effective radius from the bleached radius right after the bleaching process, $T_{1/2}$ is half time to recovery and the diffusion coefficient was 8.52 μm2/sec.

Example 6: DNA Nanopores Folding and Characterization

6HB-2C DNA nanopores were assembled by heating and cooling an equimolar mixture of 11 unmodified and two TEG-Chol-modified DNA strands (Table 2). 10 μL of each ssDNA (1 μM stock) were mixed along with 6 μL of 200 mM MgCl₂, 10 μL of 10×TE (pH=8.0) and MilliQ water to prepare a 100 μL folding mixture. The mixture was divided into 50 μL aliquots so that the solution maintained an even contact with the heating elements of the thermocycler. Aliquots were first heated to a temperature of 95° C. and then sequentially cooled to 16° C. by reducing the temperature at a rate of 0.13° C. per minute. For 6HB control nanopores without cholesterol anchors (6HB) and other variations such as 6HB-1C, and 6HB-3C, 6HB-2B, 6HB-2C, 6HB-2C-2B, 6HB-2C-2AP and fluorescent tagged nanopores, the sequences were appropriately modified (for sequences, see Table 2).

TABLE 2

| Nanopore oligonucleotide sequences | | |
|---|---|---|
| Sequence Name | SEQ ID NO | Oligo Sequence |
| 6HB-2C nanopores | | |
| S1-A | 1 | AAATCCACGTTCTTTAATAGTGGACTCTTGTTCCAAACTGGAAC AAAA |
| S2-A | 2 | AAAGGCTATTCTTTTGATTTATAAGGGATTTTGCCGATTTCGGA AAAA |
| S3-A | 3 | AAAACAGGATTTTCGCCTGCTGGGGCAAACCAGCGTGGACCGCT TAAA |
| S4-A | 4 | AAACAACTCTCTCAGGGCCAGGCGGTGAAGGGCAATCAGCTGTT GAAA |
| S5-A | 5 | AAATCTCACTGGTGAAAAGAAAAACCACCCTGGCGCCCAATACG CAAA |
| S6-A | 6 | AAATCCCCGCGCGTTGGCCGATTCATTAATGCAGCTGGCACGAC AAAA |
| S7 | 7 | AGAGTTGGCGTATTGCGGGGA |
| S8 | 8 | TGTCGTGACGTGGATTCCGAAATCGGCAGGCGAAATGATTGCCC TTCAC |
| S9 | 9 | TCCACTATTAAAGACCAGCTGTTTCACCAGTGAGACAACAGCAT CCTGT |
| S10 | 10 | AAGCGGTAATAGCCTGTTCCA |
| S13 | 13 | GAATCGGACAAGAGTTATAAATCAAAAGCCACGCTCCCTGAG |
| S11-TEGChol | 14 | CGCCTGGGGTTTGCCCCAGCAAAATCCC/3CholTEG/ |
| S12-TEGChol | 15 | GTTTGGACCAACGCGGGCGCCAGGGTGGTTTTTCTCATTAAT/3 CholTEG/ |
| 6HB nanopores | SEQ ID NO | Oligo Sequence |
| S1-A | 1 | AAATCCACGTTCTTTAATAGTGGACTCTTGTTCCAAACTGGAAC AAAA |
| S2-A | 2 | AAAGGCTATTCTTTTGATTTATAAGGGATTTTGCCGATTTCGGA AAAA |
| S3-A | 3 | AAAACAGGATTTTCGCCTGCTGGGGCAAACCAGCGTGGACCGCT TAAA |
| S4-A | 4 | AAACAACTCTCTCAGGGCCAGGCGGTGAAGGGCAATCAGCTGTT GAAA |
| S5-A | 5 | AAATCTCACTGGTGAAAAGAAAAACCACCCTGGCGCCCAATACG CAAA |
| S6-A | 6 | AAATCCCCGCGCGTTGGCCGATTCATTAATGCAGCTGGCACGAC AAAA |
| S7 | 7 | AGAGTTGGCGTATTGCGGGGA |
| S8 | 8 | TGTCGTGACGTGGATTCCGAAATCGGCAGGCGAAATGATTGCCC TTCAC |
| S9 | 9 | TCCACTATTAAAGACCAGCTGTTTCACCAGTGAGACAACAGCAT CCTGT |
| S10 | 10 | AAGCGGTAATAGCCTGTTCCA |
| S11 | 11 | CGCCTGGGGTTTGCCCCAGCAAAATCCC |
| S12 | 12 | GTTTGGACCAACGCGGGCGCCAGGGTGGTTTTTCTCATTAAT |
| S13 | 13 | GAATCGGACAAGAGTTATAAATCAAAAGCCACGCTCCCTGAG |
| Fluorescent 6H-2C nanopores | SEQ ID NO | Oligo Sequence |
| S1-A-5/-Atto488 | 16 | /5ATTO488N/AAATCCACGTTCTTTAATAGTGGACTCTTGTTC CAAACTGGAACAAAA |
| S2-A-5'-Atto488 | 17 | /5ATTO488N/AAAGGCTATTCTTTTGATTTATAAGGGATTTTG CCGATTTCGGAAAAA |

TABLE 2-continued

| | | Nanopore oligonucleotide sequences |
|---|---|---|
| S3-A-5'-Atto488 | 18 | /5ATTO488N/AAAACAGGATTTTCGCCTGCTGGGGCAAACCAGCGTGGACCGCTTAAA |
| S4-A-5' Atto488 | 19 | /5ATTO488N/AAACAACTCTCTCAGGGCCAGGCGGTGAAGGGCAATCAGCTGTTGAAA |
| S5-A-5' Atto488 | 20 | /5ATTO488N/AAATCTCACTGGTGAAAAGAAAAACCACCCTGGCGCCCAATACGCAAA |
| S6-A-5'-Atto488 | 21 | /5ATTO488N/AAATCCCCGCGCGTTGGCCGATTCATTAATGCAGCTGGCACGACAAAA |
| S7 | 7 | AGAGTTGGCGTATTGCGGGGA |
| S8 | 8 | TGTCGTGACGTGGATTCCGAAATCGGCAGGCGAAATGATTGCCCTTCAC |
| S9 | 9 | TCCACTATTAAAGACCAGCTGTTTCACCAGTGAGACAACAGCATCCTGT |
| S10 | 10 | AAGCGGTAATAGCCTGTTCCA |
| S13 | 13 | GAATCGGACAAGAGTTATAAATCAAAAGCCACGCTCCCTGAG |
| S11-TEGChol | 14 | CGCCTGGGGTTTGCCCCAGCAAAATCCC/3CholTEG/ |
| S12-TEGChol | 15 | GTTTGGACCAACGCGGGCGCCAGGGTGGTTTTTCTCATTAAT/3CholTEG/ |

| 6HB-2C-2B nanopores | SEQ ID NO | Oligo Sequence |
|---|---|---|
| 5'Bn-S1-A | 22 | /5Biosg/TCCACGTTCTTTAATAGTGGACTCTTGTTCCAAACTGGAACAAAA |
| S2-A | 2 | AAAGGCTATTCTTTTGATTTATAAGGGATTTTGCCGATTTCGGAAAAA |
| S3-A | 3 | AAAACAGGATTTTCGCCTGCTGGGGCAAACCAGCGTGGACCGCTTAAA |
| 5'Bn-S4-A | 23 | /5Biosg/CAACTCTCTCAGGGCCAGGCGGTGAAGGGCAATCAGCTGTTGAAA |
| S5-A | 5 | AAATCTCACTGGTGAAAAGAAAAACCACCCTGGCGCCCAATACGCAAA |
| S6-A | 6 | AAATCCCCGCGCGTTGGCCGATTCATTAATGCAGCTGGCACGACAAAA |
| S7 | 7 | AGAGTTGGCGTATTGCGGGGA |
| S8 | 8 | TGTCGTGACGTGGATTCCGAAATCGGCAGGCGAAATGATTGCCCTTCAC |
| S9 | 9 | TCCACTATTAAAGACCAGCTGTTTCACCAGTGAGACAACAGCATCCTGT |
| S10 | 10 | AAGCGGTAATAGCCTGTTCCA |
| S13 | 13 | GAATCGGACAAGAGTTATAAATCAAAAGCCACGCTCCCTGAG |
| S11-TEGChol | 14 | CGCCTGGGGTTTGCCCCAGCAAAATCCC/3CholTEG/ |
| S12-TEGChol | 15 | GTTTGGACCAACGCGGGCGCCAGGGTGGTTTTTCTCATTAAT/3CholTEG/ |

| Fluorescent 6HB-2C-2B nanopores | SEQ ID NO | Oligo Sequence |
|---|---|---|
| 5'Bn-S1-A-Atto488 | 24 | /5ATTO488N/5Biosg/TCCACGTTCTTTAATAGTGGACTCTTGTTCCAAACTGGAACAAAA |
| S2-A-5'-Atto488 | 17 | /5ATTO488N/AAAGGCTATTCTTTTGATTTATAAGGGATTTTGCCGATTTCGGAAAAA |
| S3-A-5'-Atto488 | 18 | /5ATTO488N/AAAACAGGATTTTCGCCTGCTGGGGCAAACCAGCGTGGACCGCTTAAA |
| 5'Bn-S4-A-Atto488 | 25 | /5ATTO488N/5Biosg/CAACTCTCTCAGGGCCAGGCGGTGAAGGGCAATCAGCTGTTGAAA |
| S5-A-5' Atto488 | 20 | /5ATTO488N/AAATCTCACTGGTGAAAAGAAAAACCACCCTGGCGCCCAATACGCAAA |
| S6-A-5'-Atto488 | 21 | /5ATTO488N/AAATCCCCGCGCGTTGGCCGATTCATTAATGCAGCTGGCACGACAAAA |
| S7 | 7 | AGAGTTGGCGTATTGCGGGGA |
| S8 | 8 | TGTCGTGACGTGGATTCCGAAATCGGCAGGCGAAATGATTGCCCTTCAC |
| S9 | 9 | TCCACTATTAAAGACCAGCTGTTTCACCAGTGAGACAACAGCATCCTGT |
| S10 | 10 | AAGCGGTAATAGCCTGTTCCA |
| S13 | 13 | GAATCGGACAAGAGTTATAAATCAAAAGCCACGCTCCCTGAG |
| S11-TEGChol | 14 | CGCCTGGGGTTTGCCCCAGCAAAATCCC/3CholTEG/ |
| S12-TEGChol | 15 | GTTTGGACCAACGCGGGCGCCAGGGTGGTTTTTCTCATTAAT/3CholTEG/ |

TABLE 2-continued

| Nanopore oligonucleotide sequences | | |
|---|---|---|
| 6HB-2C-2AP nanopores | SEQ ID NO Oligo Sequence | |
| 5'AP-S1-A | 26 | GGCGATTCGTGATCTCTGCTCTCGGTTTCGCGTTCGTTCGTCCA CGTTCTTTAATAGTGGACTCTTGTTCCAAACTGGAACAAAA |
| S2-A | 2 | AAAGGCTATTCTTTTGATTTATAAGGGATTTTGCCGATTTCGGA AAAA |
| S3-A | 3 | AAAACAGGATTTTCGCCTGCTGGGGCAAACCAGCGTGGACCGCT TAAA |
| 5'AP-S4-A | 27 | GGCGATTCGTGATCTCTGCTCTCGGTTTCGCGTTCGTTCGCAAC TCTCTCAGGGCCAGGCGGTGAAGGGCAATCAGCTGTTGAAA |
| S5-A | 5 | AAATCTCACTGGTGAAAAGAAAAACCACCCTGGCGCCCAATACG CAAA |
| S6-A | 6 | AAATCCCCGCGCGTTGGCCGATTCATTAATGCAGCTGGCACGAC AAAA |
| S7 | 7 | AGAGTTGGCGTATTGCGGGGA |
| S8 | 8 | TGTCGTGACGTGGATTCCGAAATCGGCAGGCGAAATGATTGCCC TTCAC |
| S9 | 9 | TCCACTATTAAAGACCAGCTGTTTCACCAGTGAGACAACAGCAT CCTGT |
| S10 | 10 | AAGCGGTAATAGCCTGTTCCA |
| S13 | 13 | GAATCGGACAAGAGTTATAAATCAAAAGCCACGCTCCCTGAG |
| S11-TEGChol | 14 | CGCCTGGGGTTTGCCCCAGCAAAATCCC/3CholTEG/ |
| S12-TEGChol | 15 | GTTTGGACCAACGCGGGCGCCAGGGTGGTTTTTCTCATTAAT/3 CholTEG/ |

| Fluorescent 6HB-2C-2AP nanopores | SEQ ID NO Oligo Sequence | |
|---|---|---|
| 5'-AP-S1-A-Atto488 | 28 | /5ATTO488N/AAAGGCGATTCGTGATCTCTGCTCTCGGTTTCG CGTTCGTTCGTCCACGTTCTTTAATAGTGGACTCTTGTTCCAAA CTGGAACAAAA |
| S2-A-5'-Atto488 | 17 | /5ATTO488N/AAAGGCTATTCTTTTGATTTATAAGGGATTTTG CCGATTTCGGAAAAA |
| S3-A-5'-Atto488 | 18 | /5ATTO488N/AAAACAGGATTTTCGCCTGCTGGGGCAAACCAG CGTGGACCGCTTAAA |
| 5'-AP-S4-A-Atto488 | 29 | /5ATTO488N/AAAGGCGATTCGTGATCTCTGCTCTCGGTTTCG CGTTCGTTCGCAACTCTCTCAGGGCCAGGCGGTGAAGGGCAATC AGCTGTTGAAA |
| S5-A-5'-Atto488 | 20 | /5ATTO488N/AAATCTCACTGGTGAAAAGAAAAACCACCCTGG CGCCCAATACGCAAA |
| S6-A-5'-Atto488 | 21 | /5ATTO488N/AAATCCCCGCGCGTTGGCCGATTCATTAATGCA GCTGGCACGACAAAA |
| S7 | 7 | AGAGTTGGCGTATTGCGGGGA |
| S8 | 8 | TGTCGTGACGTGGATTCCGAAATCGGCAGGCGAAATGATTGCCC TTCAC |
| S9 | 9 | TCCACTATTAAAGACCAGCTGTTTCACCAGTGAGACAACAGCAT CCTGT |
| S10 | 10 | AAGCGGTAATAGCCTGTTCCA |
| S13 | 13 | GAATCGGACAAGAGTTATAAATCAAAAGCCACGCTCCCTGAG |
| S11-TEGChol | 14 | CGCCTGGGGTTTGCCCCAGCAAAATCCC/3CholTEG/ |
| S12-TEGChol | 15 | GTTTGGACCAACGCGGGCGCCAGGGTGGTTTTTCTCATTAAT/3 CholTEG/ |

The self-assembled structures were then characterized to confirm the correct and successful formation of DNA nanopores. Since the structures were formed from equimolar ratios of ssDNA strands, purification was not necessary. The concentration of the resulting double stranded DNA nanostructures was analyzed with a spectrophotometer using UV absorbance spectra. Native gel electrophoresis was performed to verify the completeness of the folded structure and to verify the migration of the control nanopores without any cholesterol vs. migration of 6HB-1C, 6HB-2C, and 6HB-3C nanopores (FIG. 14A). The 6HB-2C nanopores yielded a predominate band, which migrated with a larger apparent molecular mass than control nanopore without any cholesterol anchors (FIG. 14A, lanes 3 and 5 respectively). DLS established the monomeric nature of the DNA nanopores, as only a single peak (volume-based size distribution) with an average hydrodynamic radius of 9.73 nm was observed (left side curve in FIG. 14C). Intensity based size-correlograms (FIG. 14D) and polydispersity index values (Table 3) for the 6HB and 6HB-3C nanopores showed the presence of multiple-size distributions, possibly comprising higher-order aggregates as unpurified samples were used for the experiments. For biotin modified nanopores, 6HB-2B and 6HB-2C-2B, gel electrophoresis showed the accessibility of the biotin tags as slower migration patterns and dimer/quadrate aggregation patterns were observed in presence of excess streptavidin protein (1:20 concentration ratios; FIG. 14B, lanes 6 and 8). No such migration pattern changes were observed in non-biotinylated nanopores, showing they were appropriate as controls (FIG. 14B, lane 7).

TABLE 3

| Polydispersity Index values for dynamic light scattering data | | |
|---|---|---|
| Name | 6HB | 6HB-3C |
| Z-Average (nm) | 138.8 | 1097 |
| Polydispersity Index (PI) | 0.8249 | 0.7364 |
| Peak One Width by Number (nm) | 2.636 | 12.25 |
| Peak One Mean by Number (nm) | 9.755 | 60.48 |
| Peak Two Width by Number (nm) | — | 165.3 |
| Peak Two Mean by Number (nm) | — | 683.2 |
| Intercept | 0.7152 | 0.5497 |
| In Range (%) | 90.4 | 81.02 |
| Fit Error | 0.03045 | 0.00771 |

Regarding Table 3, the intensity based Polydispersity Index (PI) and hydrodynamic Z-average size (cumulants mean) values for 6HB and 6HB-3C nanopores were averaged over 5 scans as observed on Zetasizer instrument (Malvern). The presence of aggregates can heavily skew calculations due to large scattering effects. However, a small percentage of aggregates was expected, so number based mean values were used and contrasted against the intensity-based calculations with the intent to provide a more relevant estimate of the nanopore population distribution.

Example 7: Kinetics of DNA Nanopore to Membrane Self-Insertion

To better understand the dynamics of DNA nanopore insertion into the SLB, a model was created to analyze the insertion process of the DNA nanopore in the lipid bilayer based on Langmuir's equation and absorption/desorption kinetics. In this model, DNA nanopores in solution (n) and lipid bilayer sites where the nanopores can be absorbed (l) as being initially separate (Eq. 14 left side). Upon insertion of the DNA nanopore into the lipid bilayer, the DNA nanopore and the lipid bilayer sites are conjoined as nl (Eq. 14 right side).

$$n + l \xrightleftharpoons[k_d]{k_a} nl \tag{14}$$

Figure 11A:
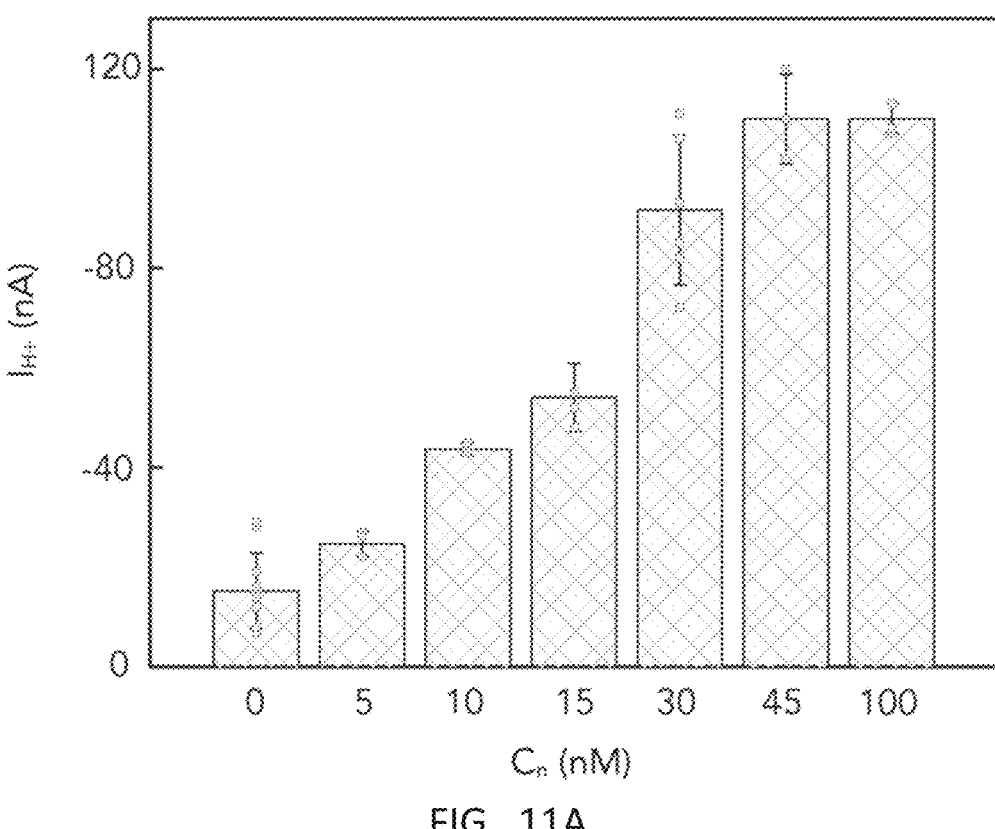
FIG. 11A to FIG. 11D show an illustration of DNA nanopore characteristics.
Figure 11B:
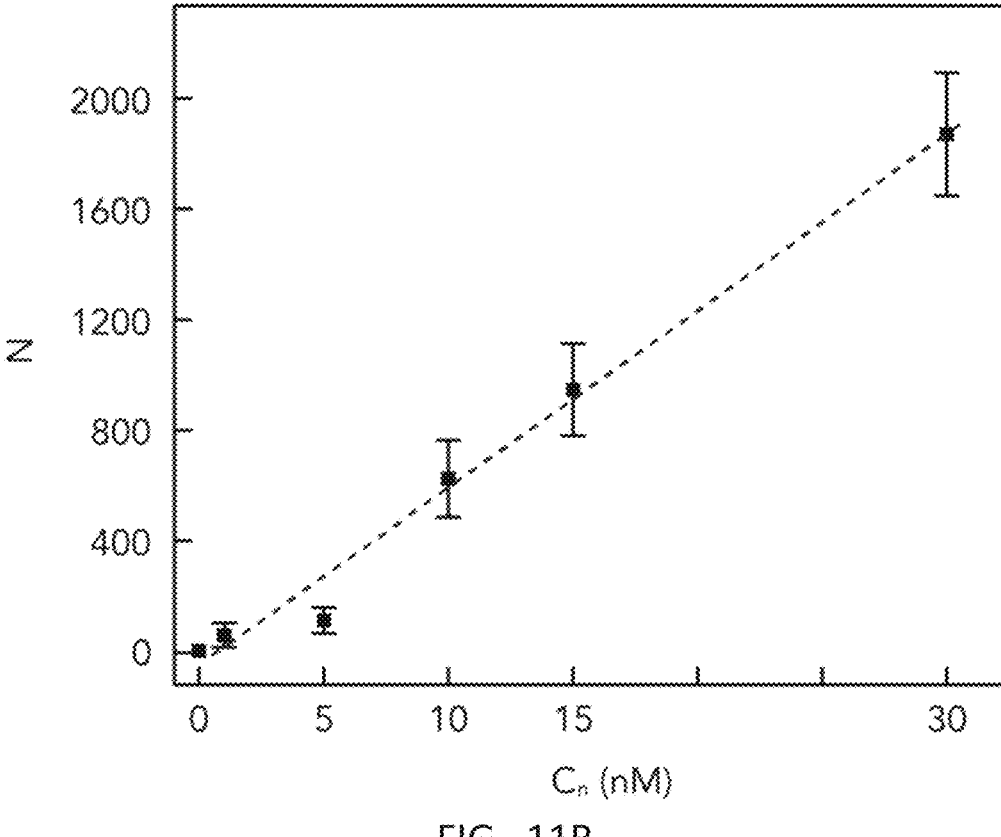
Figure 11C:
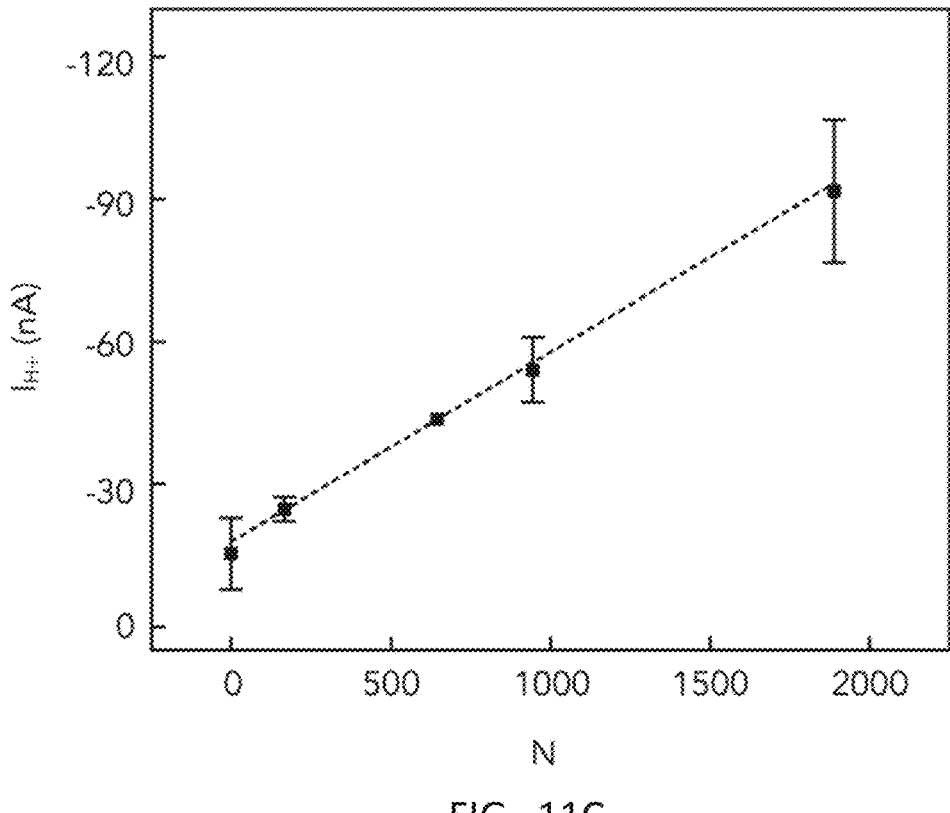
Figure 11D:
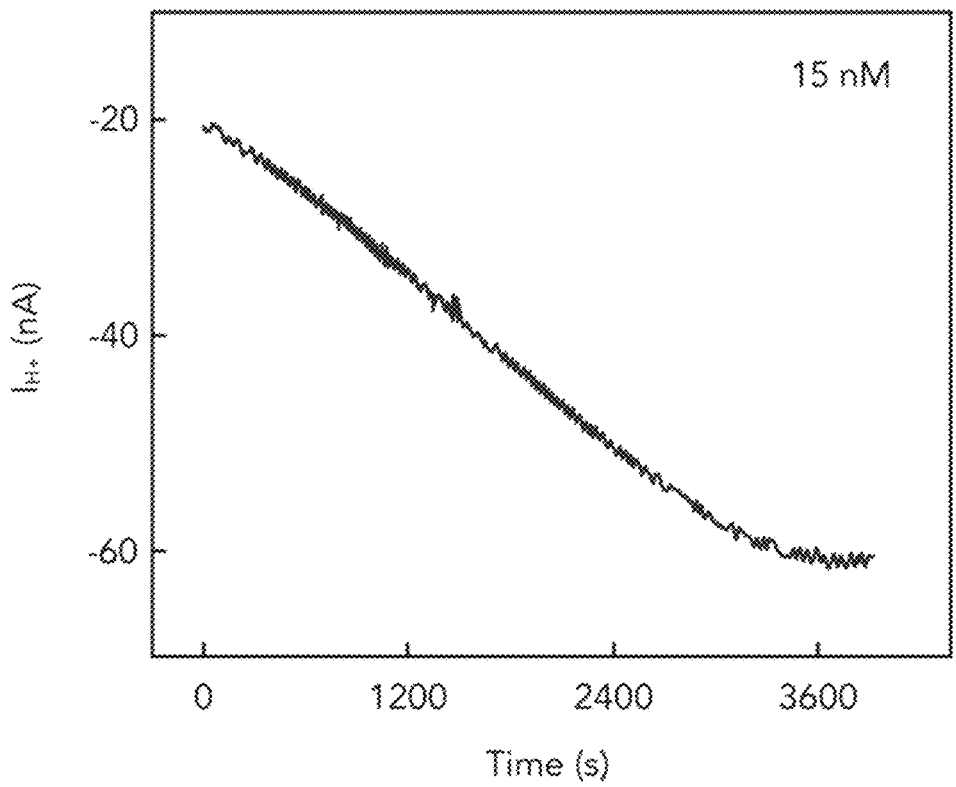

The rate constant $k_a$ ($M^{-1}$ $s^{-1}$) describes the absorption reaction of the DNA nanopore into the lipid bilayer and the rate constant $k_{off}$ ($s^{-1}$) describes the desorption reaction. From this model, it is expected that more DNA nanopores in solution (n) corresponds to a higher number of DNA nanopores inserted into the lipid bilayer (nl), resulting in an increase in $I_{H+}$ as a function of DNA nanopore concentration ($C_n$) (FIG. 11A). Given the large number of DNA nanopores compared to the absorption area of the lipid bilayer, $C_n$ was assumed to be constant throughout the absorption process. $k_a$ and $k_{off}$ were needed to fully understand absorption and desorption kinetics, so the differential form of the Langmuir equation was utilized:

$$\frac{dC_{nl}}{dt} = k_a C_n C_u - k_d C_{nl} \tag{15}$$

where $C_n$ and $C_{nl}$ represent the DNA nanopore concentrations in solution and lipid bilayers, respectively, and $C_u$ represents the unoccupied site concentration in the SLB. Since $C_u$ is an unknown that we are not able to derive experimentally, Eq. 15 was written as:

$$\frac{dC_{nl}}{dt} = k_a C_n (C_{max} - C_{nl}) - k_d C_{nl} \tag{16}$$

Where $C_{max} = C_u + C_{nl}$ and $C_{max}$ is the maximum value of $C_{nl}$. We derive $C_{nl}$ by counting the number of inserted DNA nanopores (N=$C_{nl}V_l$A, where $V_l$=the volume of lipids, A=Avogadro's number) as a function of $C_n$ at equilibrium using fluorescent microscopy on fluorescently tagged nanopores (FIG. 11B, FIG. 19). $C_{max}$ was not measurable using fluorescent microscopy for $C_n$>30 nM due to dense packing of inserted DNA nanopores, which prevented accurate counting. In FIG. 11A, $I_{H+}$ increased with increasing $C_n$ for $C_n$<45 nM. $I_{H+}$ plateaued even when $C_n$ was increased to 100 nM. Thus, for $C_n$>45 nM, $C_{nl}$ was assumed to equal $C_{max}$. To calculate $C_{max}$ from $I_{H+}$, DNA nanopores were modeled as resistors in parallel:

$$\frac{R_m}{N} = \frac{V_{H+}}{I_{H+}} \tag{17}$$

and from Eq. 17 and the slope of FIG. 11C, $R_m$ was calculated to be $1\times10^{10}\Omega$ and $G_m=1/R_m=100$ pS, the resistance and conductivity of each individual nanopore. These values were consistent with the conductivity of artificial and natural membrane channels. Using the calculated value of $R_m$, $N_{max}$ yielded 2350 nanopores per device and a $C_{max}$ of 2 nM. $C_{nl}/d_t$ was experimentally observed by recording $I_{H+}$ as a function of time introducing the DNA nanopores in the solution for t=0 (FIG. 11D). We can thus assume $C_{nl}=0$ and Eq. 16 simplified to:

$$k_a = \frac{dC_{nl}}{dt}/(C_n C_{max}) \tag{18}$$

Using N=$C_{nl}V_l$A and Eq. 16, $dC_{nl}/d_t$ was expressed as:

$$\frac{dC_{nl}}{dt} = \left|\frac{dI_{H+}}{d_t}\right| \cdot \frac{R_m}{V_{H+}} \frac{1}{V_l \times A} \tag{19}$$

Combing Eqs. 18 and 19, $k_a$ was expressed as:

$$k_a = \left|\frac{dI_{H+}}{d_t}\right| \cdot \frac{R_m}{V_{H+}} \frac{1}{C_n C_{max}} \frac{dC_{nl}}{dt} \tag{7 20}$$

From the slope of FIG. 11D at t=0, $k_a$ was calculated to be $8.5\times 10^3$ $M^{-1}$ $s^{-1}$.

The time t when the system reached dynamic equilibrium and $dC_{nl}/dt=0$ yielded:

$$k_a C_n(C_{max} - C_{nl,e}) = k_{off} C_{nl,e} \tag{8 21}$$

where $C_{nl,e}$ was the adsorbate concentration in bilayers at equilibrium. $C_{nl,e}$ was derived from $I_{H+}$ and $k_{off}$ calculated as $1.9\times10^{-4}$ $s^{-1}$. The apparent dissociation constant was calculated to be $k_D=k_d/k_a=22$ nM. The apparent dissociation constant indicated a high affinity of the 6HB-2C to the SLBs, one that is higher than the affinity of most protein-ligand interactions (i.e., 100 µM-100 nM).

Example 7: Simulation

Molecular dynamics (MD) simulations were performed with NAMD software using periodic boundary conditions.

The 6HB DNA nanopore design was generated with caD-NAno and converted into all atom structures. TEG-chol extensions were bound to the 3' ends of designed staple strands by using amenable "patches" provided by NAMD. TEG-chol conjugated 6HB DNA nanopores were inserted into pre-equilibrated DOPC lipid bilayer membranes using the open source macromolecular mechanics and dynamics software and with graphical user interface, CHARMM-GUI. CHARMM 36 and CGenFF force fields were used to define the TEG-chol conjugated DNA nanostructure in 0.15 KCl electrolyte and removing overlapping lipid and water molecules. For water molecules and ions, the TIP3P force field was used. After generating the initial system, the energy of lipid molecules (50,000 steps) was minimized by keeping the TEG-chol conjugated DNA nanostructure fixed. The energy of the system was minimized while keeping the TEG-chol conjugated DNA nanopore harmonically restrained (harmonic constraint energy function exponent=2) for another 50,000 steps. All the harmonic constraints were then released and the system was equilibrated for 3 ns prior to MD production runs. The whole system was then simulated for 64 ns at 295 K with a 2 fs timestep, and coordinates were saved every 4 fs. During simulations, the VDW cutoff value was taken to be 12 Å. Electrostatic interactions were computed using the Particle Mesh Ewald (PME) method, and the SHAKE bond geometry constraint algorithm was applied to keep H bonds rigid.

Example 8: Statistical & Reproducibility

Current measurements were conducted at least three times independently, and the results described herein are representative of these repeated experiments. The statistical analysis was performed on Origin and Microsoft Excel. The sample size for all experiments was not predetermined but was kept consistent across all trials. No data were excluded from the analysis. Experiments were not randomized.

Imaging was conducted at least three times, independently, and the results presented herein are representative of these repeated experiments. Each image was analyzed using Image J, and statistical distribution was performed using the Gaussian fitting function on Origin software. The sample size for all experiments was not predetermined but was kept consistent across all trials. No data were excluded from the analysis. The experiments were not randomized.

For the dynamic light scattering experiments, each independent sample was measured five times in the Zetasizer instrument (Malvern), and the software presented the average results of all the trials for each sample. No statistical method was used to predetermine sample size or the number of experimental repeats, but such parameters were kept consistent across different samples. Randomization was not used and no data was excluded from the analysis.

It should be understood that the subject matter defined in the appended claims is not necessarily limited to the specific implementations described above. The specific implementations described above are disclosed as examples only.

What is claimed is:

1. A device for sensing one or more targets in a sample, comprising a bioprotonic conducting material forming a planar array of protodes on a non-conducting substrate, wherein each protode in the planar array of protodes is electrically isolated and individually addressable;

a plurality of DNA origami tethered DNA nanopores immobilized to the planar array of protodes, wherein the outer surface of each of the plurality of DNA origami tethered DNA nanopores comprises one or more hydrophobic moieties;

an insulating membrane, defining a space inferior to the membrane and a space superior to the membrane, wherein each of the DNA origami tethered DNA nanopores spans the membrane and provides an ionic pathway between the bioprotonic conducting material inferior to the membrane and bulk solution;

a power supply in electrical contact with each protode to provide an electric potential difference across the membrane; and a detector, configured to independently acquire and resolve signals in real-time from each protode in the planar array of protodes, to detect changes in electrical signal through the DNA origami tethered DNA nanopore over time as each DNA origami tethered DNA nanopore interacts with the one or more targets, wherein the changes in electrical signal can comprise changes in signal magnitude, signal duration, or frequency of signal changes, and wherein signals from individual protodes are independently resolved to discriminate one or more targets in the sample.

2. The device of claim 1, wherein the plurality of DNA origami tethered DNA nanopores comprise one or more target binding moieties, one or more target binding linkers, or combinations thereof.

3. The device of claim 2, wherein the one or more target binding moieties comprise aptamers that interact weakly with a determinant on the one or more targets, wherein such weak interactions yield transient signal profiles distinguishable by the detector to enable multiplexed identification of targets.

4. The device of claim 3, wherein the aptamers comprise DNA, RNA, XNA, peptides, or combinations thereof.

5. The device of claim 2, wherein the one or more target binding linkers comprise staple strands for hybridization to complementary sequences attached to the one or more target binding moieties or dibenzocyclooctyne (DBCO), amine or thiol moieties suitable for coupling to complementary azide, ester or maleimide moieties, respectively, attached to one or more target binding moieties, or combinations thereof.

6. The device of claim 1, wherein the DNA nanopore is comprised of a DNA duplex, two DNA duplexes, or between about 3 and 20 helical bundles of DNA, or about 3 and 16 helical bundles of DNA, or about 4 and 16 helical bundles, or about 6 and 16 helical bundles, or about 6 and 12 helical bundles of DNA.

7. The device of claim 1, wherein the one or more hydrophobic moieties on the outer surface of the DNA nanopore comprise ethyl phosphonothioate, cholesterol, porphyrin, or combinations thereof.

8. The device of claim 1, wherein the DNA nanopores comprise one or more nucleic acids comprising DNA, RNA, LNA, PNA, BNA, other non-natural nucleic acid, or a combination thereof.

9. The device of claim 1, wherein the DNA nanopores comprise one or more non-natural nucleic acids.

10. The device of claim 1, wherein each protode comprises one or more DNA nanopores.

11. The device of claim 1, wherein each protode comprises one DNA nanopore.

12. The device of claim 1, wherein each protode in the planar array of protodes comprises one DNA nanopore, each DNA nanopore functionalized with a different target-binding moiety, such that the device detects the binding of a plurality of different targets in the sample across a plurality of protodes based on differences in signal profiles.

13. The device of claim 1, wherein each protode in the planar array of protodes comprises a plurality of DNA nanopores functionalized with a plurality of target-binding moieties, such that the device detects the binding of a plurality of different targets in the sample across one or more protodes based on differences in signal profiles.

* * * * *

SEQUENCE LISTING

```
Sequence total quantity: 29
SEQ ID NO: 1            moltype = DNA   length = 48
FEATURE                 Location/Qualifiers
source                  1..48
                        mol_type = other DNA
                        organism = synthetic construct
SEQUENCE: 1
aaatccacgt tctttaatag tggactcttg ttccaaactg gaacaaaa          48

SEQ ID NO: 2            moltype = DNA   length = 48
FEATURE                 Location/Qualifiers
source                  1..48
                        mol_type = other DNA
                        organism = synthetic construct
SEQUENCE: 2
aaaggctatt cttttgattt ataagggatt ttgccgattt cggaaaaa          48

SEQ ID NO: 3            moltype = DNA   length = 48
FEATURE                 Location/Qualifiers
source                  1..48
                        mol_type = other DNA
                        organism = synthetic construct
SEQUENCE: 3
aaaacaggat tttcgcctgc tggggcaaac cagcgtggac cgcttaaa          48

SEQ ID NO: 4            moltype = DNA   length = 48
FEATURE                 Location/Qualifiers
source                  1..48
                        mol_type = other DNA
                        organism = synthetic construct
SEQUENCE: 4
aaacaactct ctcagggcca ggcggtgaag ggcaatcagc tgttgaaa          48

SEQ ID NO: 5            moltype = DNA   length = 48
FEATURE                 Location/Qualifiers
source                  1..48
                        mol_type = other DNA
                        organism = synthetic construct
SEQUENCE: 5
```

-continued

```
aaatctcact ggtgaaaaga aaaaccaccc tggcgcccaa tacgcaaa              48

SEQ ID NO: 6          moltype = DNA   length = 48
FEATURE               Location/Qualifiers
source                1..48
                      mol_type = other DNA
                      organism = synthetic construct
SEQUENCE: 6
aaatccccgc gcgttggccg attcattaat gcagctggca cgacaaaa              48

SEQ ID NO: 7          moltype = DNA   length = 21
FEATURE               Location/Qualifiers
source                1..21
                      mol_type = other DNA
                      organism = synthetic construct
SEQUENCE: 7
agagttggcg tattgcgggg a                                           21

SEQ ID NO: 8          moltype = DNA   length = 49
FEATURE               Location/Qualifiers
source                1..49
                      mol_type = other DNA
                      organism = synthetic construct
SEQUENCE: 8
tgtcgtgacg tggattccga aatcggcagg cgaaatgatt gcccttcac            49

SEQ ID NO: 9          moltype = DNA   length = 49
FEATURE               Location/Qualifiers
source                1..49
                      mol_type = other DNA
                      organism = synthetic construct
SEQUENCE: 9
tccactatta aagaccagct gtttcaccag tgagacaaca gcatcctgt            49

SEQ ID NO: 10         moltype = DNA   length = 21
FEATURE               Location/Qualifiers
source                1..21
                      mol_type = other DNA
                      organism = synthetic construct
SEQUENCE: 10
aagcggtaat agcctgttcc a                                           21

SEQ ID NO: 11         moltype = DNA   length = 28
FEATURE               Location/Qualifiers
source                1..28
                      mol_type = other DNA
                      organism = synthetic construct
SEQUENCE: 11
cgcctggggt ttgccccagc aaaatccc                                    28

SEQ ID NO: 12         moltype = DNA   length = 42
FEATURE               Location/Qualifiers
source                1..42
                      mol_type = other DNA
                      organism = synthetic construct
SEQUENCE: 12
gtttggacca acgcgggcgc cagggtggtt tttctcatta at                   42

SEQ ID NO: 13         moltype = DNA   length = 42
FEATURE               Location/Qualifiers
source                1..42
                      mol_type = other DNA
                      organism = synthetic construct
SEQUENCE: 13
gaatcggaca agagttataa atcaaaagcc acgctccctg ag                   42

SEQ ID NO: 14         moltype = DNA   length = 28
FEATURE               Location/Qualifiers
source                1..28
                      mol_type = other DNA
                      organism = synthetic construct
misc_binding          28
                      bound_moiety = Triethyleneglycol (TEG)-Cholesterol
SEQUENCE: 14
cgcctggggt ttgccccagc aaaatccc                                    28

SEQ ID NO: 15         moltype = DNA   length = 42
FEATURE               Location/Qualifiers
source                1..42
```

```
                              mol_type = other DNA
                              organism = synthetic construct
misc_binding                  42
                              bound_moiety = Triethyleneglycol (TEG)-Cholesterol
SEQUENCE: 15
gtttggacca acgcgggcgc cagggtggtt tttctcatta at                       42

SEQ ID NO: 16       moltype = DNA  length = 48
FEATURE             Location/Qualifiers
source              1..48
                    mol_type = other DNA
                    organism = synthetic construct
misc_binding        1
                    bound_moiety = ATTO 488 fluorescent label
SEQUENCE: 16
aaatccacgt tctttaatag tggactcttg ttccaaactg gaacaaaa             48

SEQ ID NO: 17       moltype = DNA  length = 48
FEATURE             Location/Qualifiers
source              1..48
                    mol_type = other DNA
                    organism = synthetic construct
misc_binding        1
                    bound_moiety = ATTO 488 fluorescent label
SEQUENCE: 17
aaaggctatt cttttgattt ataagggatt ttgccgattt cggaaaaa             48

SEQ ID NO: 18       moltype = DNA  length = 48
FEATURE             Location/Qualifiers
source              1..48
                    mol_type = other DNA
                    organism = synthetic construct
misc_binding        1
                    bound_moiety = ATTO 488 fluorescent label
SEQUENCE: 18
aaaacaggat tttcgcctgc tggggcaaac cagcgtggac cgcttaaa             48

SEQ ID NO: 19       moltype = DNA  length = 48
FEATURE             Location/Qualifiers
source              1..48
                    mol_type = other DNA
                    organism = synthetic construct
misc_binding        1
                    bound_moiety = ATTO 488 fluorescent label
SEQUENCE: 19
aaacaactct ctcagggcca ggcggtgaag ggcaatcagc tgttgaaa            48

SEQ ID NO: 20       moltype = DNA  length = 48
FEATURE             Location/Qualifiers
source              1..48
                    mol_type = other DNA
                    organism = synthetic construct
misc_binding        1
                    bound_moiety = ATTO 488 fluorescent label
SEQUENCE: 20
aaatctcact ggtgaaaaga aaaaccaccc tggcgcccaa tacgcaaa            48

SEQ ID NO: 21       moltype = DNA  length = 48
FEATURE             Location/Qualifiers
source              1..48
                    mol_type = other DNA
                    organism = synthetic construct
misc_binding        1
                    bound_moiety = ATTO 488 fluorescent label
SEQUENCE: 21
aaatccccgc gcgttggccg attcattaat gcagctggca cgacaaaa            48

SEQ ID NO: 22       moltype = DNA  length = 45
FEATURE             Location/Qualifiers
source              1..45
                    mol_type = other DNA
                    organism = synthetic construct
misc_binding        1
                    bound_moiety = 5'-biotin
SEQUENCE: 22
tccacgttct ttaatagtgg actcttgttc caaactggaa caaaa                45

SEQ ID NO: 23       moltype = DNA  length = 45
FEATURE             Location/Qualifiers
```

-continued

```
source                    1..45
                          mol_type = other DNA
                          organism = synthetic construct
misc_binding              1
                          bound_moiety = 5'-Biotin
SEQUENCE: 23
caactctctc agggccaggc ggtgaagggc aatcagctgt tgaaa                    45

SEQ ID NO: 24             moltype = DNA   length = 45
FEATURE                   Location/Qualifiers
source                    1..45
                          mol_type = other DNA
                          organism = synthetic construct
misc_binding              1
                          bound_moiety = ATTO 488 fluorescent label-Biotin
SEQUENCE: 24
tccacgttct ttaatagtgg actcttgttc caaactggaa caaaa                    45

SEQ ID NO: 25             moltype = DNA   length = 45
FEATURE                   Location/Qualifiers
source                    1..45
                          mol_type = other DNA
                          organism = synthetic construct
misc_binding              1
                          bound_moiety = ATTO 488 fluorescent label-Biotin
SEQUENCE: 25
caactctctc agggccaggc ggtgaagggc aatcagctgt tgaaa                    45

SEQ ID NO: 26             moltype = DNA   length = 85
FEATURE                   Location/Qualifiers
source                    1..85
                          mol_type = other DNA
                          organism = synthetic construct
SEQUENCE: 26
ggcgattcgt gatctctgct ctcggtttcg cgttcgttcg tccacgttct ttaatagtgg   60
actcttgttc caaactggaa caaaa                                          85

SEQ ID NO: 27             moltype = DNA   length = 85
FEATURE                   Location/Qualifiers
source                    1..85
                          mol_type = other DNA
                          organism = synthetic construct
SEQUENCE: 27
ggcgattcgt gatctctgct ctcggtttcg cgttcgttcg caactctctc agggccaggc   60
ggtgaagggc aatcagctgt tgaaa                                          85

SEQ ID NO: 28             moltype = DNA   length = 88
FEATURE                   Location/Qualifiers
source                    1..88
                          mol_type = other DNA
                          organism = synthetic construct
misc_binding              1
                          bound_moiety = ATTO 488 fluorescent label
SEQUENCE: 28
aaaggcgatt cgtgatctct gctctcggtt tcgcgttcgt cgtccacgt tctttaatag   60
tggactcttg ttccaaactg gaacaaaa                                       88

SEQ ID NO: 29             moltype = DNA   length = 88
FEATURE                   Location/Qualifiers
source                    1..88
                          mol_type = other DNA
                          organism = synthetic construct
misc_binding              1
                          bound_moiety = ATTO 488 fluorescent label
SEQUENCE: 29
aaaggcgatt cgtgatctct gctctcggtt tcgcgttcgt cgcaactct ctcagggcca   60
ggcggtgaag gcaatcagc tgttgaaa                                        88
```